United States Patent
Marroquin Belaunzaran et al.

(10) Patent No.: US 11,484,572 B2
(45) Date of Patent: Nov. 1, 2022

(54) USE OF HLA-B27 HOMODIMERS FOR CANCER TREATMENT

(71) Applicants: UNIVERSITAT ZURICH, Zurich (CH); UNIVERSITAT BASEL, Basel (CH)

(72) Inventors: Osiris Marroquin Belaunzaran, Zurich (CH); Christoph Renner, Zurich (CH); Ulf Petrausch, Zurich (CH)

(73) Assignees: UNIVERSITÄT BASEL, Basel (CH); UNIVERSITÄT ZURICH, Zurich (CH)

( * ) Notice: Subject to any disclaimer, the term of this patent is extended or adjusted under 35 U.S.C. 154(b) by 464 days.

(21) Appl. No.: 15/668,705

(22) Filed: Aug. 4, 2017

(65) Prior Publication Data
US 2018/0028606 A1    Feb. 1, 2018

Related U.S. Application Data

(63) Continuation-in-part of application No. PCT/EP2016/052317, filed on Feb. 3, 2016.

(30) Foreign Application Priority Data

Feb. 4, 2015  (EP) .................... 15153863

(51) Int. Cl.
| | | |
|---|---|---|
| A61K 38/17 | (2006.01) | |
| A61K 48/00 | (2006.01) | |
| A61K 39/00 | (2006.01) | |
| A61K 39/395 | (2006.01) | |
| C07K 16/28 | (2006.01) | |
| A61K 45/06 | (2006.01) | |
| C07K 14/74 | (2006.01) | |
| C07K 16/00 | (2006.01) | |

(52) U.S. Cl.
CPC ........ *A61K 38/1774* (2013.01); *A61K 38/177* (2013.01); *A61K 39/0011* (2013.01); *A61K 39/395* (2013.01); *A61K 39/3955* (2013.01); *A61K 45/06* (2013.01); *A61K 48/00* (2013.01); *C07K 14/70539* (2013.01); *C07K 16/00* (2013.01); *C07K 16/2803* (2013.01); *C07K 16/2818* (2013.01); *C07K 16/2827* (2013.01); *C07K 2317/524* (2013.01); *C07K 2317/526* (2013.01); *C07K 2319/00* (2013.01); *C07K 2319/03* (2013.01); *C07K 2319/30* (2013.01)

(58) Field of Classification Search
CPC .............. A61K 38/1774; A61K 38/177; A61K 39/0011; A61K 39/395; A61K 39/3955; A61K 45/06; A61K 48/00; A61K 38/00; C07K 14/70539; C07K 16/00; C07K 16/2803; C07K 16/2818; C07K 16/2827; C07K 2317/524; C07K 2317/526; C07K 2319/00; C07K 2319/03; C07K 2319/30; C07K 14/7056; A61P 35/00; C12N 7/00; C12N 15/85; C12N 2710/10021; C12N 2710/16021; C12N 2740/15021; C12N 2750/14121

See application file for complete search history.

(56) References Cited

U.S. PATENT DOCUMENTS

2013/0078253 A1* 3/2013 Fang .................... C07K 16/18
                                                424/139.1
2013/0259876 A1* 10/2013 Murphy ............. C07K 16/2833
                                                424/173.1

FOREIGN PATENT DOCUMENTS

| JP | 2008-110975 | 5/2008 |
| WO | 99/58557 | 11/1999 |
| WO | 2007/011044 | 1/2007 |

OTHER PUBLICATIONS

Dolan et al. Cancer Control. 21(3): 231-237, Jul. 2014.*
Yu et al.Targeted Delivery of an Antigenic Peptide to the Endoplasmic Reticulum: Application for Development of a Peptide Therapy for Ankylosing Spondylitis. PLOS ONE 8 (10): 1-14, published Oct. 14, 2013.*
R. Tarazona et al.: "HLA-B2702 (77-83/83-77) Peptide Binds to—Tubulin on Human NK Cells and Blocks Their Cytotoxic Capacity", The Journal of Immunology, vol. 165, No. 12, Dec. 15, 2000, pp. 6776-6782.
Levy F et. al.: "Co-Expression of the Human HLA-B27 Class I Antigen and the E3/19K Protein of Adenovirus-2 In Insect Cells Using a Baculovirus Vector", International Immunology, Oxford Univeristy Press, GB, vol. 2, No. 10, Jan. 1, 1990, pp. 995-1002.
Santos Susana G et al.: "Induction of HLA-B27 heavy chain homodimer formation after activation in dendritic cells", Arthritis Research Therapy, vol. 10, No. 4, R100, Jan. 1, 2008, pp. 1-7.
Guillermo Mazzolini et al.: "Immunotherapy and immunoescape in colorectal cancer", World Journal of Gastroenterology, vol. 13, No. 44, Nov. 1, 2007, pp. 5822-5831.

* cited by examiner

*Primary Examiner* — Alana Harris Dent
(74) *Attorney, Agent, or Firm* — JMB Davis Ben-David

(57) ABSTRACT

The invention relates to a HLA-B27 Fc open conformer or a HLA-B27 Fc fusion protein for use in the treatment or prevention of cancer. The Fc open conformer comprises or consists of a first and a second monomer, and each monomer comprises a HLA-B27 chain. The Fc fusion protein further comprises a protein stabilizing polypeptide sequence and optionally an amino acid linker. Further aspects of the invention provide combination medicaments comprising the HLA-B27 Fc open conformer and immune checkpoint inhibitors.

12 Claims, 8 Drawing Sheets
Specification includes a Sequence Listing.

A

B

C

USE OF HLA-B27 HOMODIMERS FOR CANCER TREATMENT

CROSS REFERENCE TO RELATED APPLICATIONS

This is a Continuation-in-Part of International Patent Application No. PCT/EP2016/052317 filed Feb. 3, 2016, and which in turn claims the benefit of European Patent Application No. 15153863.4 filed Feb. 4, 2015. The contents of the foregoing applications are incorporated by reference herein in their entirety.

FIELD

The present invention relates to the use of HLA-B27 open conformers, for use in the prophylaxis or therapy of cancer.

BACKGROUND

Human leukocyte antigens (HLA) belong to the classical major histocompatibility complex (MHC) protein family. The HLA complex helps the immune system distinguish the body's own proteins from proteins made by foreign invaders such as viruses and bacteria. Humans have three main MHC class I genes, known as HLA-A, HLA-B, and HLA-C. HLA genes have many possible variations, allowing each person's immune system to react to a wide range of foreign invaders. Some HLA genes have hundreds of identified versions (alleles), each of which is given a particular number (such as HLA-B27). Closely related alleles are categorized together; for example, at least 40 very similar alleles are subtypes of HLA-B27. These subtypes are designated as HLA-B*2701 to HLA-B*2743.

Classical MHC-I molecules (designated HLA-I in humans) are trimeric structures comprising a membrane-bound heavy chain with three extracellular domains (a1, a2 and a3) that associates non-covalently with β2-microglobulin (β2m) and a small peptide. HLA I heavy chains may exist in a form not associated to β2-microglobulin or peptide. These forms are referred to as open conformers.

As all other HLA molecules, HLA-B27's principle function is to present cell-derived peptides to $CD8^+$ cytotoxic T lymphocytes (CTLs), as part of the adaptive immune response. Under normal physiological conditions, HLA-B27 molecules form heterotrimeric complexes that consist of B27 heavy chains, β2-microglobulin and peptides, which are derived from self-proteins, viruses or bacteria. In this respect, HLA-B27 resembles all other class I HLA alleles. However, HLA-B27 may also be present in cells as free-heavy chains lacking β2m-microglobulin and peptide, also referred to as HLA-B27 open conformers. Furthermore, HLA-B27 open conformer biochemical properties may also induce formation of β2m-free heavy chain homodimers through a disulphide bond formation of cysteine at position 67 (Cys 67) and position 164 (Cys 164) (Antoniou et al., JBC, 2003, 279, 8895-8902). B27 open conformers formation is not altered by the presence of peptide, therefore B27 open conformers molecules may exist bound to peptide, or without it.

B27 open conformers have been associated with the development of spondyloarthritis (SpA) in +HLA-B27 patients. Possession of HLA-B27 is strongly associated with development of spondyloarthritides, a group of related diseases including ankylosing spondylitis (AS), psoriatic arthritis, enteropathic arthritis in patients with inflammatory bowel disease (IBD), reactive arthritis after specific gastrointestinal and urogenital infections and juvenile SpA, the most recognized being AS.

The demonstration of cell surface expression of B27 open conformers led to the proposal that immunoregulatory leucocyte receptors might specifically interact with B27 open conformers. How the interaction of B27 open conformers with immunoregulatory receptors leads to AS remains undetermined.

A variety of immunoregulatory receptors can recognize B27 open conformers (in addition to the T-cell receptor (TCR)). These include the killer immunoglobulin-like receptors (KIRs) and leucocyte immunoglobulin-like receptors (LILRs), which are expressed on many types of leucocytes, including NK cells, NKT cells, monocytes, macrophages, DCs and T cells.

Cancer is a group of diseases characterized by abnormal cells of the body undergoing uncontrolled and destructive growth. Cancer cells can spread around the body and metastasize to form tumors; this growth pattern is called malignant.

SUMMARY

The present invention provides HLA-B27 open conformers for use in a treatment of cancer.

According to an aspect of the invention an isolated HLA-B27 protein homodimer (open conformer protein) is provided for use in the treatment or prevention of cancer. In certain embodiments, the HLA-B27 open conformer homodimer comprises two identical HLA-B27 polypeptide chains. In certain embodiments, the HLA-B27 protein homodimer comprises two different HLA-B27 polypeptide chains.

According to a second aspect of the invention an HLA-B27 open conformer monomer (i.e., the HLA-B27 unattached to a second HLA-B27 heavy chain polypeptide, and not bound by β2-microglobulin) is provided for use in the treatment or prevention of cancer. In certain embodiments of this aspect, the HLA-B27 monomer additionally comprises a peptide epitope fragment.

According to a third aspect of the invention, a nucleic acid molecule encoding a HLA-B27 open conformer monomer, or a fusion protein monomer according to the above aspects of the invention is provided for use in the treatment or the therapy of cancer. Expression of the fusion protein in vivo from the nucleic acid molecule will, after dimerization, lead to the fusion protein polypeptide of the invention. The concept of expressing pharmaceutically active polypeptides from nucleic acids encoding them in the patient's body is well known and may confer significant benefits to the patient.

DETAILED DESCRIPTION

Terms and Definitions

Figure 1:
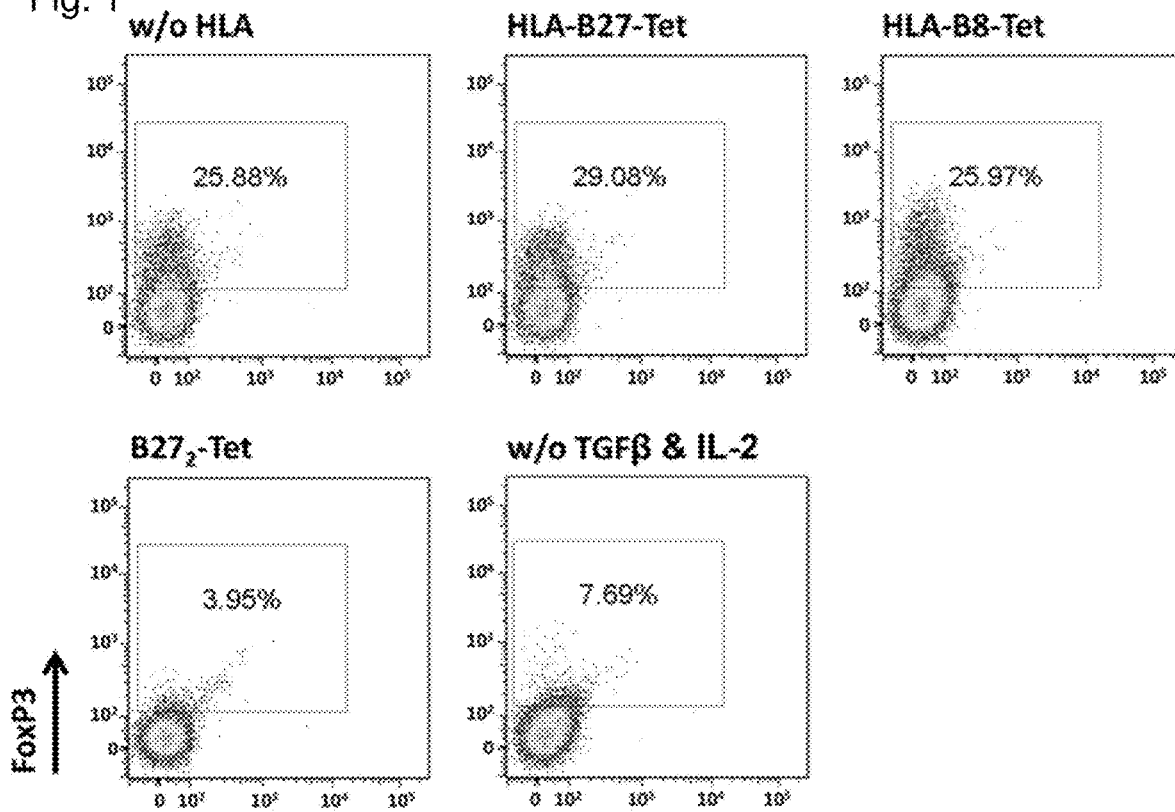
FIG. 1 shows that $B27_2$-Tet blocks $CD4^+$ T cell conversion into iTreg. Incubation of $B27_2$-Tet with naïve $CD4^+$ T cells blocks the conversion to iTregs (FoxP3). Control tetramers demonstrate the specific influence of $B27_2$-Tet on iTreg induction.
Figure 1:
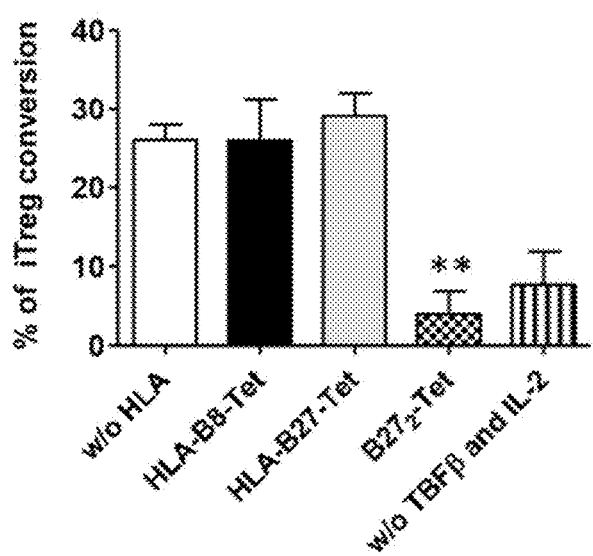
Figure 2A:
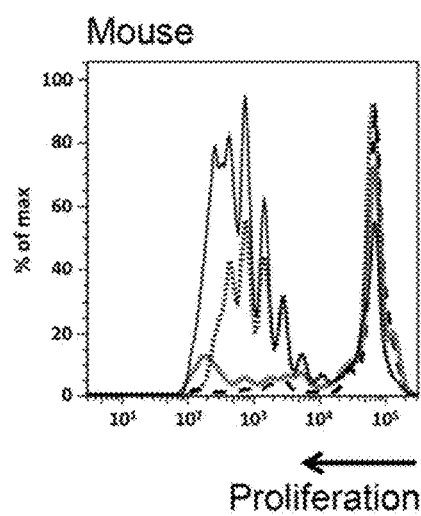
FIG. 2 shows that $B27_2$-Tet impairs the suppression of murine and human Tregs in a dose dependent matter. A) $B27_2$-Tet (2 μg/200 μL) blocks the suppression of mouse iTregs and allows the proliferation of $CD8^+$T cells. Control HLA-B27 and BSA do not alter the suppression function of iTregs. B) $B27_2$-Tet (2 μg/200 μL) block the suppression of human nTregs and allow the proliferation of human $CD8^+$T cells. Control HLA-B27-Tet and HLA-B8-Tet heterotrimers and BSA-Tet do not alter the suppression function of Tregs. C) % of iTreg suppression of murine CD8⁺T cells at different concentrations of B27$_2$-Tet (μg/200 μL). D) % of nTreg suppression of human CD8⁺T cells at different concentrations of B27$_2$-Tet (μg/200 μL).
Figure 2B:
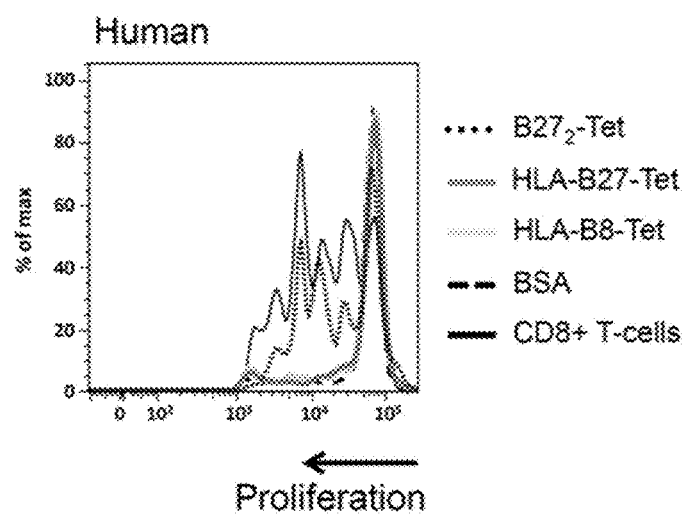
Figure 2C:
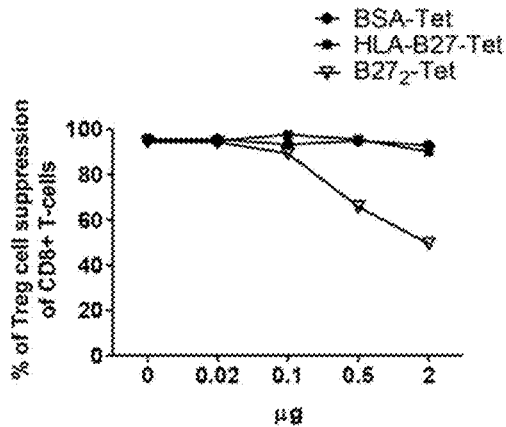
Figure 2D:
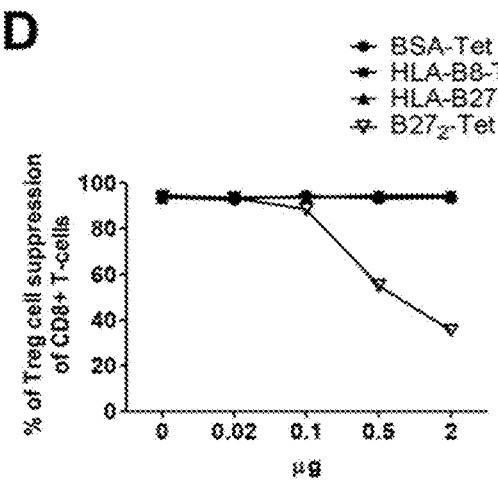

Amino acid sequences are given from amino to carboxyl terminus. Capital letters for sequence positions refer to L-amino acids in the one-letter code (Stryer, Biochemistry, 3$^{rd}$ ed. p. 21).

In the context of the present specifications the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Unless otherwise stated, sequence identity values provided herein refer to the value obtained using the BLAST suite of programs using default parameters (Altschul et al., J. Mol. Biol. 215:403-410 (1990)). Software for performing BLAST analyses is publicly available, e.g., through the National Center for Biotechnology-Information (http://blast.ncbi.nlm.nih.gov/). One example for comparison of amino acid sequences is the BLASTP algorithm that uses default settings such as: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear In the context of the present specification, the term major histocompatibility complex (MHC) is used in its meaning known in the art of cell biology and biochemistry; it refers to a cell surface molecule that displays a specific fraction (peptide), also referred to as an epitope, of a protein. There a two major classes of MHC molecules: class I and class II.

MHC class I heavy chain molecules usually (i.e. when not in open conformer form) occur as an alpha chain linked to a unit of the non-MHC molecule β2-microglobulin. The alpha chain comprises, in direction from the N-terminus to the C-terminus, a signal peptide, three extracellular domains (α1-3, with α1 being at the N terminus), a transmembrane region and a C-terminal cytoplasmic tail. The peptide being displayed or presented is held by the peptide-binding groove, in the central region of the α1/α2 domains.

In the context of the present specification, the term β2-microglobulin domain is used in its meaning known in the art of cell biology and biochemistry; it refers to a non-MHC molecule that is part of the MHC class I heterodimer molecule. In other words, it constitutes the β chain of the MHC class I heterodimer.

In the context of the present specification, the term human leukocyte antigen (HLA) is used in its meaning known in the art of cell biology and biochemistry; it refers to gene loci encoding the human MHC class I proteins. The three major MHC class I genes in HLA are HLA-A, HLA-B and HLA-C and all of these genes have a varying number of alleles, for example HLA-B has 3590 known alleles. Closely related alleles are combined in subgroups of a certain allele. For example the allele HLA-B27 has more than 160 closely related alleles that are, according to the WHO Nomenclature Committee for Factors of the HLA System, labelled HLA-B*27:01:00 to HLA-B*27:99:00. The full or partial sequence of all known HLA genes and their respective alleles are available to the person skilled in the art in specialist databases such as IMGT/HLA (http://www.ebi.ac.uk/ipd/imgt/hla/).

In the context of the present specification, the term antibody is used in its meaning known in the art of cell biology and immunology; it refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

In the context of the present specification, the term fragment crystallizable (Fc) region is used in its meaning known in the art of cell biology and immunology; it refers to a fraction of an antibody comprising two identical heavy chain fragments comprised of a $C_H2$ and a $C_H3$ domain, covalently linked by disulfide bonds.

In the context of the present specification, the term dimer refers to a unit consisting of two subunits.

In the context of the present specification, the term homodimer refers to a dimer comprised of two subunits that are either identical or are highly similar members of the same class of subunits. One example for a homodimer would be a dimer consisting of two subunits independently selected from the list of HLA-B27 alleles. In certain embodiments, homodimers consist of two identical HLA-B27 alleles.

In the context of the present specification, the term amino acid linker refers to a polypeptide of variable length that is used to connect two polypeptides in order to generate a single chain polypeptide. Exemplary embodiments of linkers useful for practicing the invention specified herein are oligopeptide chains consisting of 1, 2, 3, 4, 5, 10, 20, 30, 40 or 50 amino acids. A non-limiting example of an amino acid linker is the polypeptide GGGGSGGGGS (SEQ ID NO 173) that links an HLA-B27 polypeptide with an Fc domain.

In the context of the present specification, the term checkpoint inhibitory agent or checkpoint inhibitory antibody is meant to encompass an agent, particularly a (non-agonist) antibody (or antibody-like molecule) capable of disrupting the signal cascade leading to T cell inhibition after T cell activation as part of what is known in the art the immune checkpoint mechanism. Non-limiting examples of a checkpoint inhibitory agent or checkpoint inhibitory antibody include antibodies to CTLA-4 (Uniprot P16410), PD-1 (Uniprot 015116), PD-L1 (Uniprot Q9NZQ7), B7H3 (CD276; Uniprot Q5ZPR3), Tim-3, Gal9, VISTA, or Lag3.

In the context of the present specification, the term checkpoint agonist agent or checkpoint agonist antibody is meant to encompass an agent, particularly but not limited to an antibody (or antibody-like molecule) capable of engaging the signal cascade leading to T cell activation as part of what is known in the art the immune checkpoint mechanism. Non-limiting examples of receptors known to stimulate T cell activation include CD122 and CD137 (4-1BB; Uniprot 007011). The term checkpoint agonist agent or checkpoint agonist antibody encompasses agonist antibodies to CD137 (4-1BB), CD134 (OX40), CD357 (GITR), CD278 (ICOS), CD27, CD28.

In the context of the present specification, the term (immune) checkpoint modulatory agent encompasses checkpoint inhibitory agents, checkpoint inhibitory antibodies checkpoint agonist agents and checkpoint agonist antibodies.

The present invention provides HLA-B27 open conformers for use in a treatment of cancer.

According to an aspect of the invention an isolated HLA-B27 protein homodimer (open conformer protein) is provided for use in the treatment or prevention of cancer.

In certain embodiments, the HLA-B27 open conformer homodimer comprises two identical HLA-B27 polypeptide chains. In certain embodiments, the HLA-B27 protein homodimer comprises two different HLA-B27 polypeptide chains.

According to an alternative of this first aspect of the invention, an HLA-B27 open conformer fusion protein homodimer is provided for use in the treatment or prevention of cancer. The fusion protein homodimer comprises or consists of two monomers, and each monomer independently of any other monomer comprises an HLA-B27 chain, and a polypeptide domain known to metabolically stabilize a polypeptide in vivo. One example of such stabilizing domain is an Fc (fragment crystallizable) domain of an immunoglobulin. The HLA-B27 chain and the stabilizing domain may optionally be joined by an amino acid linker. An open conformer fusion protein comprising the HLA-B27 chain and an immunoglobulin Fc fragment is henceforth termed HLA-B27 Fc open conformer or $B27_2$-Fc herein.

In certain embodiments the Fc domain is present in the fusion protein for increasing solubility, stability, avidity, half-life, and from a technological point of view, cost-effective production and purification in mammalian systems (protein A or G purification).

In certain embodiments the HLA-B27 open conformer homodimers are produced without Fc region and coupled to a biotinylation recognition sequence, leading to its biotinylation during synthesis in culture. The resulting product comprises a biotin moiety. In certain embodiments, a plurality of the HLA-B27 fusion protein homodimers are coupled to a substrate such as—but not limited to—streptavidin coated beads. This multimerization increases the stability of the HLA-B27 open conformers for in vitro tests. In certain embodiments four HLA-B27 open conformer homodimers are assembled into a tetramer by binding to streptavidin coated beads (B27$_2$-Tet).

In certain embodiments the HLA-B27 open conformer homodimer additionally comprises a peptide epitope fragment.

According to a second aspect of the invention an HLA-B27 open conformer monomer (i.e., the HLA-B27 unattached to a second HLA-B27 heavy chain polypeptide, and not bound by β2-microglobulin) is provided for use in the treatment or prevention of cancer. In certain embodiments of this aspect, the HLA-B27 monomer additionally comprises a peptide epitope fragment.

This aspect can be summarized in the following items:

Item 1: An isolated single HLA-B27 heavy chain polypeptide monomer essentially free of associated β2-microglobulin for use in the treatment or prevention of cancer.

Item 2: The isolated single HLA-B27 heavy chain polypeptide monomer for use in the treatment or prevention of cancer according to item 1, wherein the monomer additionally comprises a peptide epitope fragment.

Item 3: The isolated single HLA-B27 heavy chain polypeptide monomer for use in the treatment or prevention of cancer according to items 1 or 2, wherein the HLA-B27 chain only consists of the HLA-B27 alpha 1, 2 and 3 domains.

Item 4: The isolated single HLA-B27 heavy chain polypeptide monomer for use in the treatment or prevention of cancer according to any one of the preceding items, wherein the HLA-B27 chain comprises the transmembrane domain and does not comprise the intracellular domain (cytoplasmic tail).

Item 5: The isolated single HLA-B27 heavy chain polypeptide monomer for use in the treatment or prevention of cancer according to any one of the preceding items, wherein the HLA-B27 chain has ≥70%, ≥80%, ≥85%, ≥90%, ≥92%, ≥93%, ≥94%, ≥95%, ≥96%, ≥97% or ≥98%, or 100%, sequence identity compared to any one of the sequences identified by SEQ ID NO consecutively numbered SEQ ID NO 006 to SEQ ID NO 172.

Item 6: A combination medicament comprising
  a. an isolated single HLA-B27 heavy chain polypeptide monomer as specified in any one of items 1 to 5, and
  b. a checkpoint modulatory agent selected from a checkpoint inhibitory agent and a checkpoint agonist agent.

Item 7: The combination medicament according to item 6, wherein said checkpoint inhibitory agent is selected from an inhibitor of CTLA4 interaction with CD80 or CD86, an inhibitor of the interaction of PD-1 with its ligand PD-L1, and a ligand TIM-3, particularly an antibody against any one of CTLA4, CD80, CD86, PD-1, PD-L1 or TIM-3, more particularly a monoclonal antibody against human CTLA4 or PD-1.

In certain embodiments of any one of the aspects of the invention laid out above, the peptide epitope fragment is non-covalently attached to the polypeptide within the antigen presenting domain of the HLA-B27 peptide chain.

In certain embodiments of any one of the aspects of the invention laid out above, the HLA-B27 chain comprises only the extracellular HLA-B27 alpha 1, 2 and 3 domains. In these embodiments, the transmembrane and intracellular domains of the HLA-B27 chain are not included in order to allow for extracellular expression of the molecule in recombinant cells.

In certain embodiments of any one of the aspects of the invention laid out above, the HLA-B27 chain of the homodimer is selected from HLA-B*27:05, HLA-B*27:02, HLA-B*27:04, HLA-B*27:01, HLA-B*27:03, HLA-B*27:07, HLA-B*27:08, HLA-B*27:10, HLA-B*27:13, HLA-B*27:14, HLA-B*27:15, HLA-B*27:19, HLA-B*27:23, HLA-B*27:24, HLA-B*27:25 or HLA-B*27:49.

In certain embodiments of any one of the aspects of the invention laid out above, the HLA-B27 chain comprises only the HLA-B27 alpha 1, 2 and 3 domains, but not the transmembrane and intracellular domain of a sequence selected from the HLA-B*27:05, HLA-B*27:02, HLA-B*27:04, HLA-B*27:01, HLA-B*27:03, HLA-B*27:07, HLA-B*27:08, HLA-B*27:10, HLA-B*27:13, HLA-B*27:14, HLA-B*27:15, HLA-B*27:19, HLA-B*27:23, HLA-B*27:24, HLA-B*27:25 or HLA-B*27:49.

HLA-B*27:05 is the most widely distributed disease-associated allele. However, other common disease-associated subtypes include, but are not limited to, HLA-B*27:02 (Mediterranean populations) and HLA-B*27:04 (Chinese and other Asian populations), and further HLA-B*27:01, HLA-B*27:03, HLA-B*27:07, HLA-B*27:08, HLA-B*27:10, HLA-B*27:13, HLA-B*27:14, HLA-B*27:15, HLA-B*27:19, HLA-B*27:23, HLA-B*27:24, HLA-B*27:25 and HLA-B*27:49 are contemplated for use with the present invention. These types are also known to be disease associated, as at least one or more spondyloarthritis patients possessing these subtypes have been observed.

In certain embodiments of any one of the aspects of the invention laid out above, the HLA-B27 chain has ≥70%, ≥80%, ≥85%, ≥90%, ≥92%, ≥93%, ≥94%, ≥95%, ≥96%, ≥97% or ≥98%, or 100% sequence identity compared to any one of SEQ ID NOs 006 to 172.

In certain embodiments, the HLA-B27 open conformer homodimer or HLA-B27 fusion protein homodimer consists of two subunits independently selected from the above HLA-B27 alleles. In certain embodiments, homodimers consist of two identical HLA-B27 alleles.

In certain embodiments the HLA-B27 fusion protein homodimer comprises an Fc domain. In certain particular embodiments the Fc domain comprises heavy chain constant regions $C_H2$ and $C_H3$ from immunoglobulin type G (IgG), type A (IgA), type D (IgD), type E (IgE) or type M (IgM).

In certain embodiments the HLA-B27 fusion protein homodimer comprises an amino acid linker joining a stabilizing domain, particularly an Fc domain, to the HLA polypeptide. In certain particular embodiments, the amino acid linker comprises 1 to 50 amino acids, particularly 5 to 40 amino acids, more particularly 10 to 30 amino acids, even more particularly 15 to 25 amino acids that link the HLA-B27 chain to the Fc domain as one single polypeptide chain.

According to a third aspect of the invention, a nucleic acid molecule encoding a HLA-B27 open conformer monomer, or a fusion protein monomer according to the above aspects of the invention is provided for use in the treatment or the therapy of cancer. Expression of the fusion protein in vivo from the nucleic acid molecule will, after dimerization, lead to the fusion protein polypeptide of the invention. The concept of expressing pharmaceutically active polypeptides from nucleic acids encoding them in the patient's body is well known and may confer significant benefits to the patient.

In certain embodiments, the nucleic acid molecule encodes a HLA-B27 fusion protein monomer comprising a peptide epitope fragment. In certain embodiments, the nucleic acid molecule encodes a HLA-B27 fusion protein monomer that comprises only the extracellular HLA-B27 alpha 1, 2 and 3 domains. In certain embodiments, the nucleic acid molecule encodes a HLA-B27 fusion protein monomer that comprises only the extracellular HLA-B27 alpha 1, 2 and 3 domains, and a peptide epitope fragment.

In certain embodiments, the nucleic acid molecule encodes a HLA-B27 fusion protein monomer that comprises an amino acid linker and/or an Fc (fragment crystallizable) domain, and is used in the treatment or the therapy of cancer.

According to a fourth aspect of the invention a recombinant expression vector comprising the nucleic acid molecule according to the third aspect of the invention is provided for use in the treatment or the therapy of cancer.

In certain embodiments the recombinant expression vector is a plasmid comprising a promoter that is operable in a mammalian cell, particularly in a human cell. The promoter is operably linked to the nucleic acid molecule of the invention.

According to another aspect of the invention a virus comprising the nucleic acid molecule according to the third aspect of the invention is provided for use in the treatment or the therapy of cancer. The nucleic acid molecule is under control of a promoter sequence operable in a mammalian cell, particularly in a human cell. In certain embodiments, the virus is an adenovirus, adeno-associated virus, a herpes virus or a lentivirus.

According to yet another aspect of the invention an in vitro genetically modified host cell comprising the nucleic acid molecule according to the third aspect of the invention is provided.

Another aspect of the invention provides for the use of the HLA-B27 open conformer homodimer or fusion protein homodimer according to the first and second aspect of the invention in the manufacture of a medicament for the treatment or prevention of cancer.

According to yet another aspect, the invention provides a method of treatment for cancer, comprising administering an HLA-B27 open conformer according to the first and second aspect of the invention to a patient in need thereof.

According to another aspect of the invention, a combination medicament is provided, wherein the combination medicament comprises:
 a HLA-B27 open conformer homodimer or a fusion protein according to any one of the above aspects or embodiments of the invention, and
 an immune checkpoint modulatory agent selected from an immune checkpoint inhibitory agent selected from an inhibitor of cytotoxic T-lymphocyte-associated protein 4 (CTLA4; also known as CD152) interaction with CD80 or CD86, an inhibitor of the interaction of programmed cell death protein 1 (PD-1; also known as CD279) with its ligand PD-L1, and a ligand of T cell immunoglobulin and mucin domain-containing 3 (TIM-3), and an immune checkpoint agonist agent.

In certain embodiments, the immune checkpoint inhibitory agent is an inhibitor of interaction of CTLA4 with CD80 or CD86.

In certain embodiments, the immune checkpoint inhibitory agent is ipilimumab (Yervoy; CAS No. 477202-00-9).

In certain embodiments, the HLA-B27 open conformer homodimer or the fusion protein HLA-B27 homodimer is provided as parenteral dosage form, particularly confectioned for injection.

In certain embodiments, the immune checkpoint modulatory agent is provided as parenteral dosage form, particularly confectioned for injection. In certain embodiments, both the HLA-B27 homodimer and the immune checkpoint modulatory agent are present in the same administration form.

In yet another aspect, the invention relates to a method for producing recombinant HLA heavy chain polypeptides. This method is summarized in the following items:

Item A: A method for producing, by methods of recombinant biotechnology, a human HLA heavy chain polypeptide, wherein said method comprises the following steps:
 a. Expression step:
  i. a HLA-encoding nucleic acid sequence encoding at least the alpha 1 chain, the alpha 2 chain and the alpha 3 chain of a HLA heavy chain under control of a promoter sequence operable in a cell, particularly a eukaryotic cell, more particularly a mammalian cell, and
  ii. a β2-microglobulin encoding nucleic acid sequence encoding the human HLA beta 2 microglobulin (UniProt P61769) under control of a promoter sequence operable in said cell (the same cell as in item 1. a.) are co-expressed in a mammalian cell ("production cell line");
 b. Purification step: the resulting HLA-heavy-chain/β2-microglobulin complex is purified from the mammalian cell (the production cell line);
 c. Dissociation step: the purified HLA-heavy-chain/β2-microglobulin complex is dissociated under suitable conditions and the HLA heavy chain polypeptides are separated from the β2-microglobulin polypeptides;
 d. Refolding step: the separated HLA heavy chain polypeptides are incubated under conditions leading to refolding (of their native tertiary protein structure found in physiologically active HLA open conformer molecules).

Item B: The method for producing a human HLA heavy chain polypeptide according to item A, wherein the HLA-encoding nucleic acid sequence comprises, from N to C terminus of the encoded polypeptide, the alpha 1 chain, the alpha 2 chain, the alpha 3 chain and a stabilizing sequence.

Item C: The method for producing a human HLA heavy chain polypeptide according to item B, wherein the stabilizing sequence is selected from bovine serum albumin and an immunoglobulin constant fragment (Fc), particularly an immunoglobulin G constant fragment, more particularly an IgG4 Fc.

Item D: The method for producing a human HLA heavy chain polypeptide according to any of the preceding items, wherein the HLA-encoding nucleic acid sequence and the β2-microglobulin encoding nucleic acid sequence are present on the same nucleic acid vector molecule (particularly, a DNA expression plasmid).

Item E: The method for producing a human HLA heavy chain polypeptide according to any of the preceding items A to C, wherein the HLA-encoding nucleic acid sequence and the β2-microglobulin encoding nucleic acid sequence are present on different nucleic acid vector molecules (particularly, different DNA expression plasmids).

Item F: The method of item E, wherein the nucleic acid vector comprising the HLA-encoding nucleic acid sequence is present in approximately 1- to 5-fold excess, particularly 1.5 to 5-fold excess with respect to the nucleic acid vector comprising the β2-microglobulin encoding nucleic acid sequence, particularly in approximately 3-fold excess.

Item G: The method of any of the preceding items, wherein the HLA-encoding nucleic acid sequence comprises an immunoglobulin Fc fragment as a stabilizing sequence and the purification step is effected by adsorbing the recombinant HLA heavy chain polypeptides to a surface linked to protein A.

Item H: The method of any of the preceding items, wherein the dissociation step is effected by treatment under acidic conditions, particularly at approximately pH 2, and dialysis under reductive conditions.

Item I: The method of any of the preceding items, wherein the refolding step is effected by treatment under neutral conditions.

Wherever alternatives for single separable features such as, for example, an allele or coding sequence are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

Examples

The inventors surprisingly found that HLA-B27 open conformers, particularly when present as fusion proteins comprising an Fc immunoglobulin fragment, could be useful in cancer therapy. $B27_2$-Fc molecules may be used alone or in combinations with other cancer therapeutics.

In Vitro Tests

Figure 3:
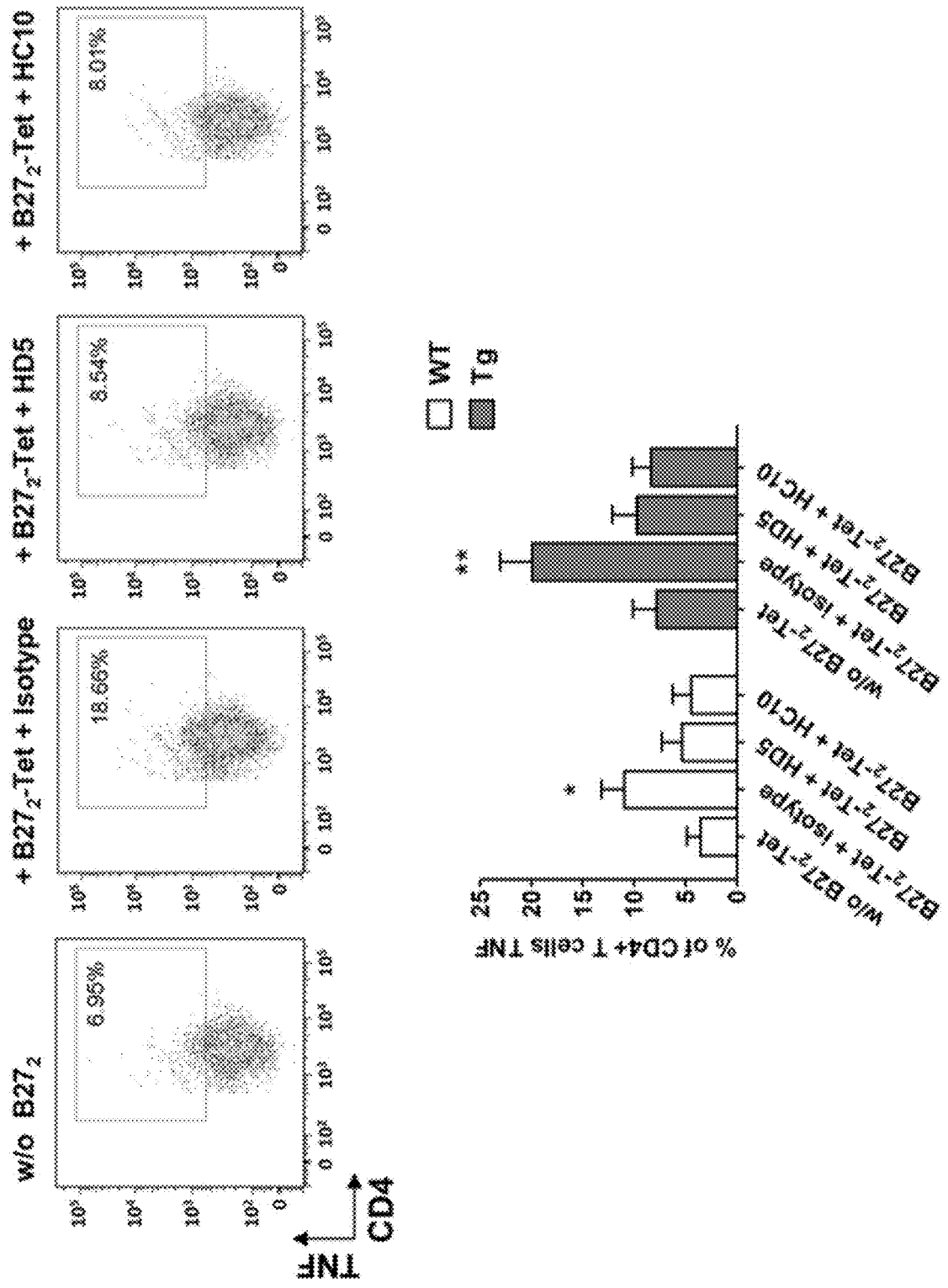
FIG. 3 shows B27$_2$ modulates activation of CD4⁺ T cells. HLA-B27 Tg and WT CD4⁺ T cells from rat produce TNF after incubation with B27$_2$_Tet. Pre-incubation of antibodies HD5 or HC10 that block B27$_2$ inhibited the interaction to CD4⁺ T cells and the production of TNF, demonstrating that B27$_2$-Tet is able to alone activate CD4⁺ T cells to produce cytokines.

The $B27_2$-Tet molecule is able to modulate immune responses in both human and rodents through influencing Tregs suppression, and activating T cells in vitro (FIG. 1-3)

$B27_2$-Tet Blocks Conversion of Murine CD4$^+$ T Cells into iTregs

The influence of HLA molecules with naïve CD4$^+$ T cells for iTreg conversion was analysed. 0.5 μg/mL of $B27_2$-, HLA-B27-, and HLA-B8-tetramers were incubated with naïve CD4$^+$ T cells in optimal culture conditions for iTreg conversion. $B27_2$-Tet demonstrated to down modulate the induction of FoxP3 (FIG. 1).

$B27_2$-Tet Impairs the Suppression of Murine and Human CD8$^+$ T Cells by Tregs The suppressive function of murine and human Tregs using violet-labelled naïve CD8$^+$ T cells as responder cells was determined (FIG. 2). Tregs were co-cultured with HLA- and BSA-tetramers and proliferation of CD8$^+$ T cells was measured after 96 h. CD8$^+$ T cells alone showed strong proliferation and, as expected, Treg cells suppressed the proliferation of CD8$^+$ T cells when incubated with control tetramers (HLA-B27, HLA-B8 and BSA). Strikingly, the suppressive function of Tregs was greatly impaired in the presence of $B27_2$ tetramers indicated by a strong proliferation of CD8$^+$ T cells in both mice (FIG. 2A), and human (FIG. 2B) suppression assays. The effect of $B27_2$-Tet was dose dependent in both mice (FIG. 2C) and human (FIG. 2D).

Figure 4A:
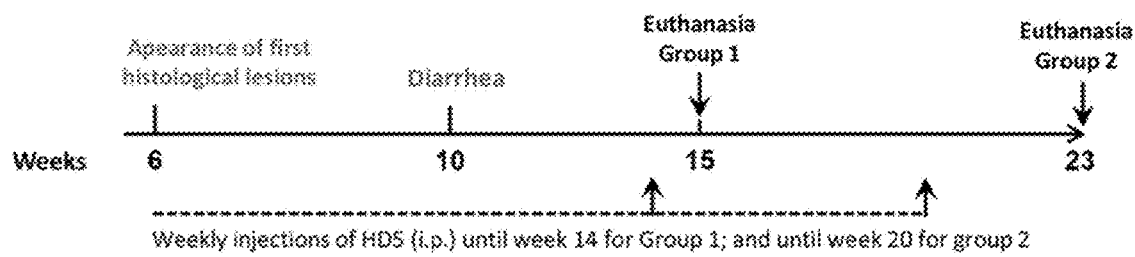
FIGS. 4A-4C shows reduced expansion of pro-inflammatory CD4⁺ T cells from spleen and MLN in treated rats with HD5 (anti-B27$_2$ antibody). 4A. Time points of the in vivo study with HLA-B27 rats and HD5 injections. Rats were administered intraperitoneally (i.p.) with 10 mg/kg of HD5 antibody per rat, every week during a period of 12-15 weeks. 4B-4C. in vitro stimulated cells obtained from Tg-HD5, Tg-ctrl and WT-littermates were assessed by ICS for the presence of pro-inflammatory cells expressing TNF (4B) and IL-17 (4C). MLN and spleens cells were obtained at week 15 (n=5) and at week 23 (n=5). Results are plotted as the percentage of CD4⁺ T cells gated positive for TNF, IL-17 and IFN-γ. Values are expressed as mean±SEM. $*p<0.05$, $p<0.01$, $*p<0.005$ as determined by one-way ANOVA followed by Bonferroni post-hoc analysis.
Figure 4B:
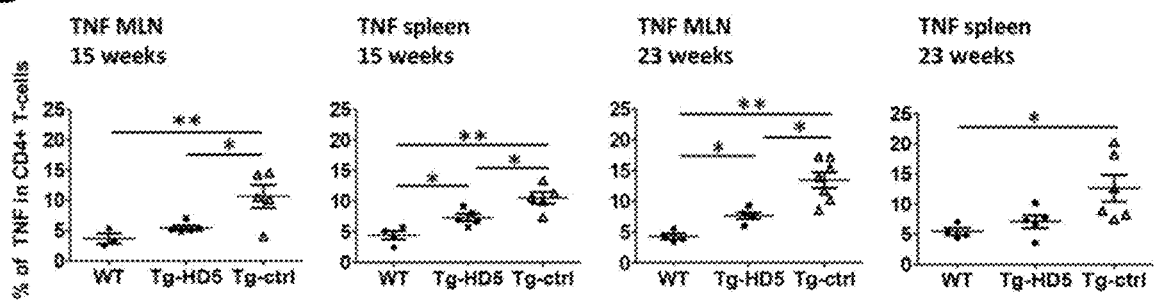
Figure 4C:
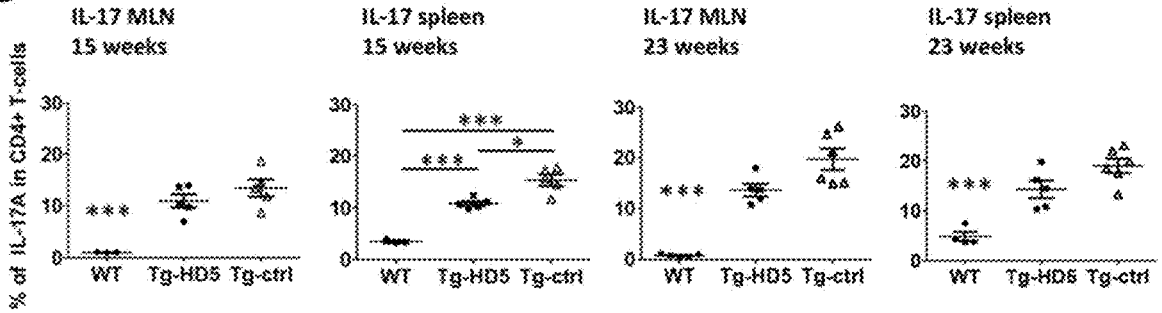

Antibodies Against B27 Open Conformers Homodimers Reduce the Expansion of Effector CD4$^+$ T Cells, and Demonstrate the Immunomodulating Effect of B27 Open Conformers Homodimers in Transgenic +HLA-B27 Rats To demonstrate the involvement of B27 open conformer homodimers in disease in vivo a specific antibody against B27 open conformer homodimers (HD5) was generated. As an in vivo model we used the HLA-B27 rat model of SpA that progresses to disease resembling human SpA pathology with elevated number of pro-inflammatory lymphocytes (Th1, Th17, TNF$^+$ CD4$^+$ T cells). Ex vivo data from HLA-B27 rats lymphocytes demonstrated that the sole presence of $B27_2$-Tet was capable of inducing expression of pro-inflammatory cytokines from CD4$^+$ T cells (FIG. 3). Furthermore in vivo results generated by injecting anti-B27 open conformer homodimers antibodies (HD5) (FIG. 4A-C) demonstrated that by blocking B27 open conformer homodimers molecules in vivo, immune responses were modulated and the expansion of TNF CD4$^+$ T cells (FIG. 4B) and Th17 cells (FIG. 4C) in different organs was significantly decreased.

To demonstrate the proof of concept of $B27_2$-Fc as a therapeutic molecule in cancer, experiments using a validated pre-clinical syngeneic murine colon carcinoma model were conducted.

Production of B27 Open Conformers as a Human Fc Fusion Protein in CHO Cells

Figure 5A:
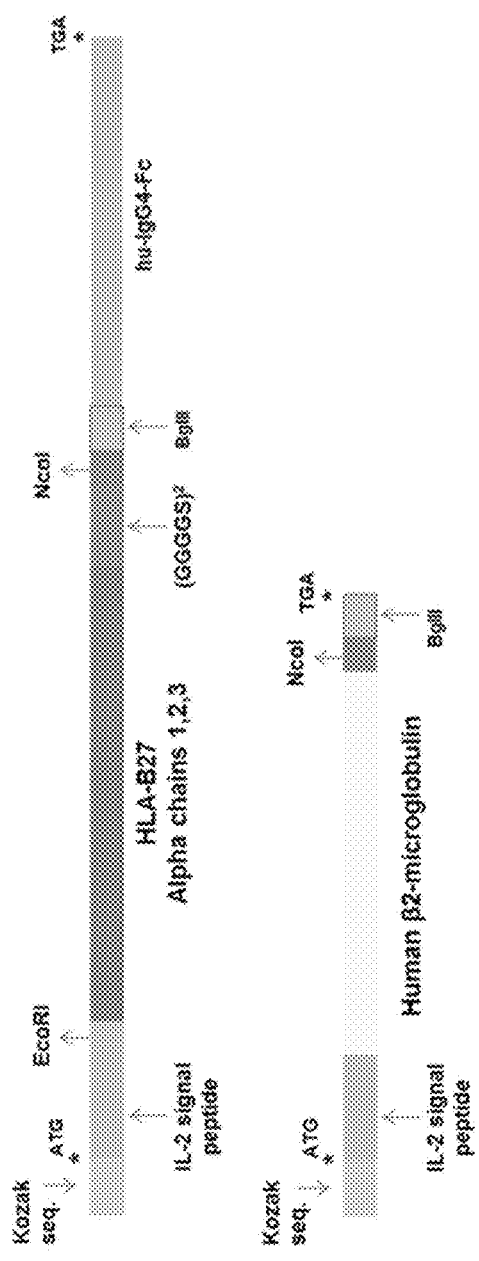
FIGS. 5A-5B show schematic representation of B27$_2$-Fc and β2m DNA cassettes and expression of B27$_2$-Fc molecules from CHO cells. 5A. B27$_2$-β2m-Fc complex was produced by inserting the alpha 1, 2 and 3 domains of HLA-B27 into a human IgG4-Fc vector cassette, together with a human-β2m vector, necessary for extracellular production of the B27$_2$-β2m-Fc protein 5B. Transfections in Chinese hamster ovary cells (CHO) cells were performed using both the B27$_2$-Fc-vector+β2m-vector at a ratio of 1:3. Supernatants were collected and B27$_2$-Fc-β2m purified using standard antibody purification protocols.
Figure 5B:
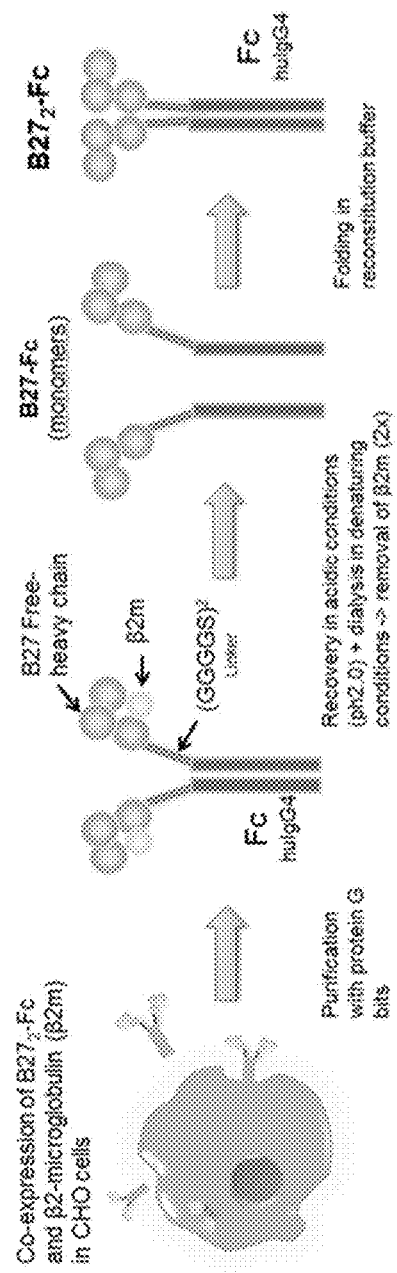
Figure 6A:
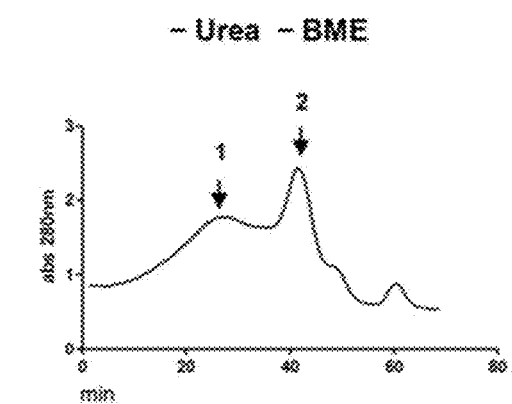
FIGS. 6A-6D show the separation of β2m from the B27$_2$-β2m-Fc complex and purification and refolding of B27$_2$-Fc by SEC or dialysis. 6A) Chromatography histogram plot and western blot analysis of B27$_2$-β2m-Fc oligomers and B27$_2$-β2m-Fc products purified from Superdex 200 prep grade columns by SEC, show that non-denaturing conditions do not separate β2m from complex and B27$_2$-β2m-Fc oligomers are formed. 6B) Chromatography histogram plot and western blot of B27$_2$-β2m-Fc molecules in Urea-Tris-BME denaturing buffer show the dissociation of B27-Fc-free heavy chains from β2m using Sephacryl S-100 HR columns by SEC. 6C) Dialysis of B27$_2$-β2m-Fc molecules in Urea-Tris-BME buffer dissociate B27-Fc-free heavy chains from β2m using 30 KDa (5) or 50 KDa (6) dialyzing membranes. 6D) Re-folding of B27-Fc-free heavy chains into B27$_2$-Fc molecules is performed by the dilution method in refolding buffer and detected by HC10 (monoclonal antibody against HLA free-heavy chains). BME=β-mercaptoethanol. Approximate KDa size of B27$_2$-Fc=125 KDa; B27-Fc free-heavy chains=62.5 KDa.
Figure 6B:
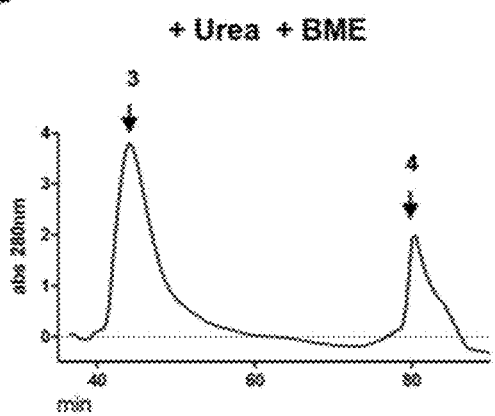
Figure 6C:
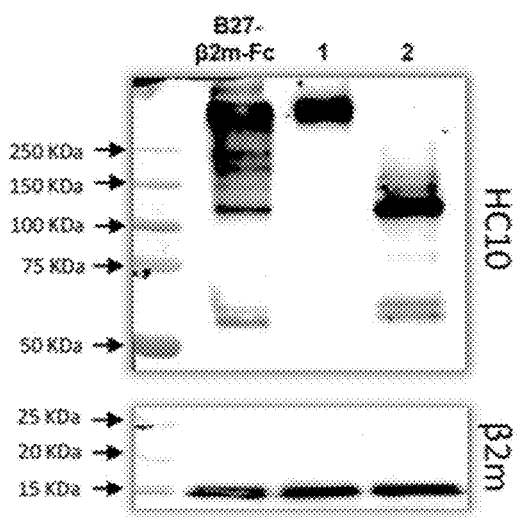
Figure 6D:
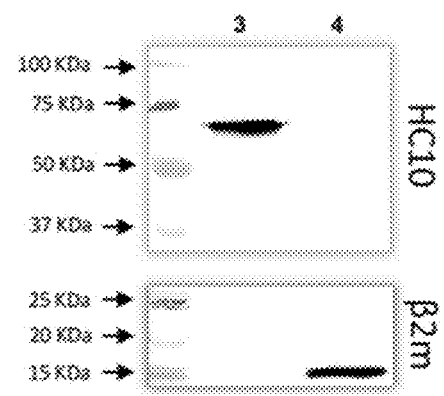

A valid strategy, from a therapeutic point of view, is to produce HLA-B27 open conformer molecules in stable format (Fc fusion), to increase solubility, stability, avidity, half-life, and from a technological point of view, cost-effective production and purification in mammalian systems. $B27_2$-β2m-Fc complex was successfully produced by inserting the alpha 1, 2 and 3 domains of HLA-B27 into a human IgG4-Fc vector cassette (FIG. 5A), together with a human-β2m vector, necessary for extracellular production of the $B27_2$-β2m-Fc protein (FIG. 5A,B). Transfections in Chinese hamster ovary cells (CHO) cells were performed using both the B27-Fc-vector+β2m-vector at a ratio of 1:3. Supernatants were collected and $B27_2$-β2m-Fc purified using standard antibody purification protocols (Recombinant Protein Purification Handbook, principles and methods. 2009. GE Healthcare, 18-1142-75) (FIG. 5B). Separation of β2m from B27-Fc free-heavy chains was performed using denaturing conditions by SEC or dialysis methods (FIG. 6). Refolding of $B27_2$-Fc was assessed using the dilution method in refolding buffer and analysed by western blot (FIG. 6D).

Toxicity Study of $B27_2$-Fc

Toxicity studies were performed in 6 weeks old C57BL/6 wild type mice. Doses of $B27_2$-Fc at 0, 0.1 mg/kg, 1 mg/kg, 10 mg/kg were injected i.p. into mice twice a week for three weeks. General health conditions showed no changes (paralysis, stress, anxiety, listlessness, signs of infection, abdominal breathing, hunched back or ruffled fur, weight and stool), when comparing PBS group with treated groups. Lymphocytes populations remain constant between groups, naïve and effector CD4$^+$ T cells, CD8$^+$ T cells, NK, B cells and monocytes displayed no change in numbers between groups. Based on this data we pursued to test 10 mg/kg of $B27_2$-Fc for in vivo tests in syngeneic cancer mouse models.

Figures 7A, 7B, 7C, 7D, 7E:
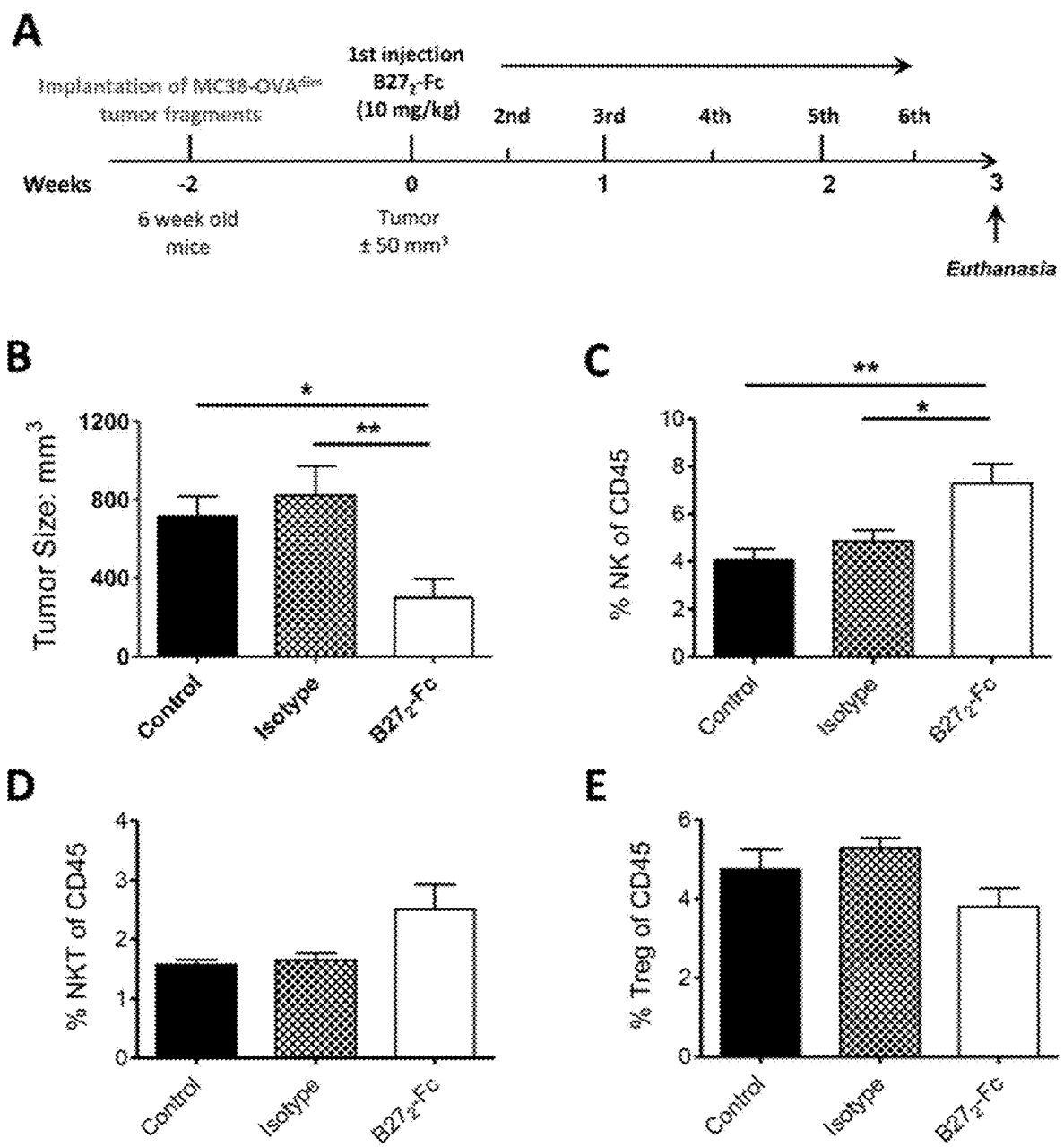
FIGS. 7A-7E show B27$_2$-Fc injections reduce the size of tumors in the MC38 colon carcinoma mouse model. 7A) Experimental design of injection time points of colon carcinoma cells (MC38-OVA$^{dim}$) and injection of B27$_2$-Fc. 7B) Tumor size of mice after euthanasia showing significant reduction of tumors in B27$_2$-Fc treated mice compared to controls. 7C) % of NK cells infiltrating the tumor was significantly higher in B27$_2$-Fc treated mice. 7D) % of NKT cells infiltrating the tumor, no significant change was observed. 7E) % of Treg cells infiltrating the tumor, no significant change was observed, but a tendency of reduced amount of Tregs is observed in B27$_2$-Fc mice when compared to isotype. Results are plotted from two identical experiments at different time points. Values are expressed as mean±SEM. $*p<0.05$, $**p<0.01$ as determined by one-way ANOVA followed by Bonferroni post-hoc analysis.

Pre-Clinical Tests of $B27_2$-Fc Monotherapy in a Syngeneic Colon Carcinoma Mouse Model Injections of the $B27_2$-Fc molecule (10 mg/kg) were performed in a therapeutic scenario (FIG. 7A). Following established protocols MC38-OVA$^{dim}$ fragment tumours were subcutaneously injected in the flank of syngeneic mice. Once the tumour reached 100 mm3 (between 1-2 weeks after injection of tumours) $B27_2$-Fc was injected i.p. twice a week for a period of three weeks (FIG. 7A) and tumours were sized and analysed for infiltration of lymphocytes (FIGS. 7B-E).

Results demonstrated that B27$_2$-Fc was capable of reducing significantly the tumor development in MC38-OVA$^{dim}$ mice when compared to controls (FIG. 7B). A mechanistic effect of B27$_2$-Fc mode of action was observed by a significant infiltration of NK cells into tumors compared to controls (FIG. 7C), pointing out to a mechanism were NK cells are key players in the modulation of tumor growth. A decreased trend on the number of Tregs was observed when compared to isotype, but was not significant (p<0.1) (FIG. 7E). Results are plotted from two separate experiments.

Figure 8A:
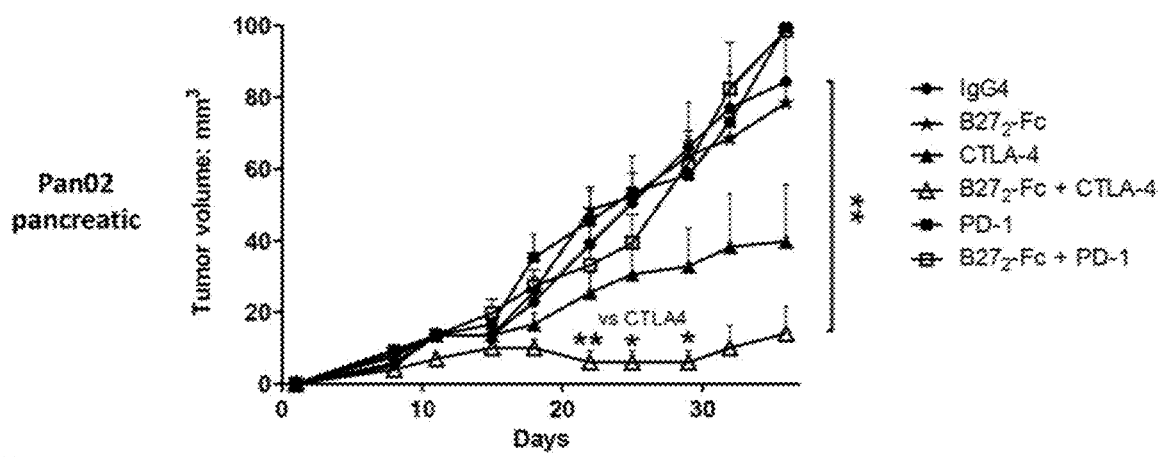
FIGS. 8A-8C. Show the combination of B27$_2$-Fc with CTLA4 or PD-1 antibodies using syngeneic models of: Pan02 murine pancreatic model, EMT6 murine breast model, and EG.7 murine lymphoma model. 8A) Mean average tumor volume in Pan02 mice (n=6). 8B) Mean average tumor volume in EMT6 (n=6) mice. 8C) Mean average tumor volume in EG.7 mice plotted from two separate experiments. The experimental design of injection time points of cells and injection of substances was as follows: isotype (10 mg/Kg) Q3Dx7; B27$_2$-Fc (10 mg/Kg); anti-CTLA4 Q3Dx3 (1st injection 200 μg, 2$^{nd}$ and 3$^{rd}$ injection 100 μg); PD-1 biwk×3 (100 μg); B27$_2$-Fc+CTLA4 (Q3Dx7 and Q3Dx3, respectively), and B27$_2$-Fc+PD-1 (Q3Dx7 and biwk×3, respectively). Tumor volumes are expressed as mean±SEM and analysed by two-way ANOVA followed by Bonferroni post-hoc analysis, $*p<0.05$, $**p<0.01$. Q=days between injections; Dx=number of injections, biwk=twice a week.
Figure 8B:
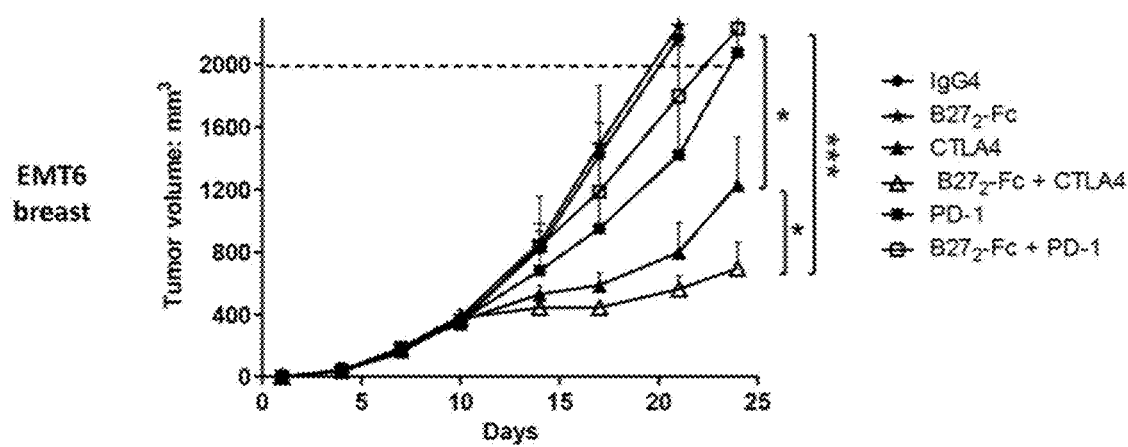
Figure 8C:
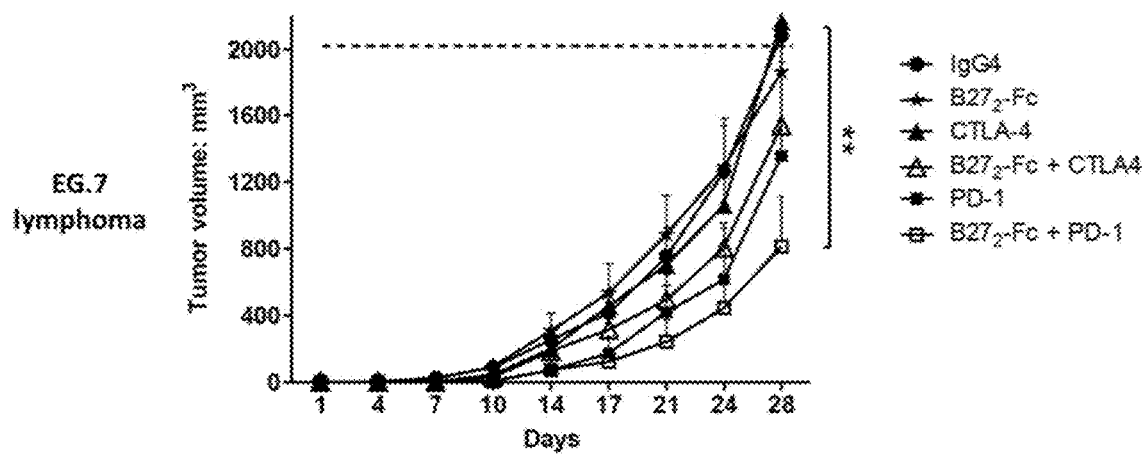

Pre-Clinical Combination Therapy Tests of B27$_2$-Fc with CTLA4 and PD-1 Antibodies in Syngeneic Cancer Mouse Models Following established protocols Pan02 1×10$^6$ cells, EMT6 1×10$^6$ cells and EG.7 1×10$^6$ cells were subcutaneously injected in the flank of syngeneic mice groups respectively. Mice were distributed according to their tumor volume (Pan02 and EMT6) or weight (EG.7). B27$_2$-Fc was injected i.p. seven times every 3$^{rd}$ day (Q3Dx7), CTLA4 was injected 3 times at selected intervals (Q3Dx7) (FIG. 8), and PD-1 injected 6 times twice a week (biwkx3) (FIG. 8).

Results demonstrated that the combination with CTLA4 antibodies together with B27$_2$-Fc was capable of enhancing the therapeutic effects of the CTLA4 antibodies and reducing significantly the tumour development in Pan02 pancreas and EMT6 breast cancer models when compared to CTLA4 monotherapy and isotype control groups. Results in combination approaches with PD-1 antibodies showed that B27$_2$-Fc enhanced the therapeutic effects of PD-1 antibodies in the EG.7 lymphoma model when compared to isotype or vehicle (p<0.01), but not to PD-1 monotherapy. PD-1 monotherapy was not significantly different when compared to isotype or vehicle.

CONCLUSION

The proof of principle for using B27$_2$-Fc molecules to fight cancer was demonstrated in pre-clinical experiments in different syngeneic cancer mouse models, either as monotherapy or combo therapy with CTLA4 or PD-1 antibodies.

Toxicity studies demonstrated that B27$_2$-Fc therapy did not induced any signs of toxicity, and during in vivo experiments the survival of mice was not compromised in the treated groups at any time point of the therapy.

In the MC38-OVA$^{dim}$ we found that infiltration of NK cells into the tumour microenvironment was elevated in B27$_2$-Fc treated mice. This data points to a mechanism were NK cells are actively participating in anti-tumour responses through activation of B27$_2$. Henceforth B27$_2$-Fc will be developed and further tested as a novel class of drug in the management of cancer therapeutics.

B27$_2$-Fc emerges as a novel class of immunomodulating drug. In vitro and in vivo data points to a mechanism were B27$_2$-Fc molecules act as a switch-on mechanism for the activation of anti-tumor immunity, most likely by altering mechanisms related to immune checkpoints, or break of tolerance of DC, NK and/or T cells.

Without wishing to be bound by theory, the inventors hypothesize that the interaction of B27 open conformers with DCs, T cells and NK cells results in altered cell signalling to promote the survival/expansion of cells that participate in and exacerbate the immune response.

Materials and Methods

Animals and Cell Lines

FoxP3 (eGFP) reporter mice (B6.Cg-Foxp3$^{tm2Tch}$/J) were obtained from The Jackson Laboratories for iTreg assay and bred at University Hospital Zurich animal facilities. HLA-B27/hβ2m transgenic (33-3 line) (Tg), and wild-type (WT) Fischer F344 male rats were obtained from Taconic (Germantown, N.Y.) and bred at the University Hospital Zurich animal facilities. Wild-type C57Bl/6 mice were bred and maintained at the University Hospital Basel animal facilities. MC38-OVA$^{dim}$ is a mouse derived colon carcinoma tumor cell line.

In Vivo Treatments

HLA-B27/hβ2m transgenic (33-3 line) (Tg), and wild-type (WT) Fischer F344 male rats were divided into three groups and randomly assigned to treatment with HD5 mAb (anti-B27$_2$) or anti-Her2neu (control antibody) accordingly: a. WT-littermates (n=8), b. Tg-HD5 (n=10), c. Tg-ctrl (anti-Her2neu) control group (n=10). Each Tg rat received a weekly intraperitoneal (i.p.) injection of HD5 or anti-Her2neu (ctrl) (10 mg/kg) up to the age of 15 weeks or 23 weeks. WT-littermates received no treatment.

Toxicity studies were performed in 6 weeks old C57BL/6 mice. Doses of B27$_2$-Fc 0, 0.1 mg/kg, 1 mg/kg, 10 and 20 mg/kg were injected i.p. into mice twice a week for a period of three weeks. MC38-OVA$^{dim}$ tumour fragments were injected subcutaneously into the right flanks of syngeneic female C57BL/6 mice at week 6. Once the tumour reached ±50 mm$^3$ animals were distributed according to their individual tumour volume size and divided into groups displaying no statistical differences between them. In the Pan02 pancreatic cancer mouse model, 1×10$^6$ Pan02 cells were injected in the flank of syngeneic female C57BL/6 mice, and animals were distributed according to their tumour volume±10 mm$^3$ and divided into groups displaying no statistically differences between them. In the EMT6 breast cancer mouse model, 5×10$^6$ EMT6 cells were injected in the flank of syngeneic female BALB/c mice, and animals were distributed according to their tumour volume±40 mm$^3$ and divided into groups displaying no statistically differences between them. In the EG.7 lymphoma mouse model, 1×10$^6$ EG.7 cells were injected in the flank of syngeneic female C57BL/6 mice, and animals were distributed according to their body weight and divided into groups displaying no statistically differences between them. Tumour diameters were measured using a caliper, and volume was calculated according to the formula, $D/2×d^2$ where D and d are the longest and shortest diameter of the tumour in mm, respectively.

The Experimental design of injection time points of cells and injection of substances was established as follows: vehicle (PBS 200 µL); isotype (10 mg/Kg) Q3Dx7; B27$_2$-Fc (10 mg/Kg); anti-CTLA4 Q3Dx3 (1st injection 200 µg, 2$^{nd}$ and 3$^{rd}$ injection 100 µg); PD-1 biwkx3 (100 µg); B27$_2$-Fc+CTLA4 (Q3Dx7 and Q3Dx3, respectively), and B27$_2$-Fc+PD-1 (Q3Dx7 and biwkx3, respectively). Tumours were sized and analysed for infiltration of lymphocytes by flow cytometry analysis in the MC38-OVA$^{dim}$ model.

Animal experiments were performed according to Swiss federal and cantonal laws on animal protection.

Antibodies

Lymphocytes mouse populations were stained with: CD4 (FITC-BD Bioscience), FoxP3+(efluor 450—eBioscience), CD3 (PE-Cy7—eBioscience), CD45 (PerCP—eBioscience), CD3 (PE—eBioscience), Granzyme B (Alexa 647, GB11; Biol), NK1.1 (BV421—eBioscience), CD11 b (FITC—eBioscience), CD11c (FITC—eBioscience), and Ter119 (FITC—eBioscience).

Lymphocyte rat populations were stained with: CD3 (APC-Cy7—BD-Pharmingen), CD4 (PE-Cy7—BD-Pharmingen), IL-17A (eBio17B7-APC, eBioscience), TNF (PE—Biolegend), Lymphocyte human populations were stained with: CD4 (PE—Biolegend), FoxP3 (eFluor 450—eBioscience), CD3 (APC-Cy7—Biolegend).

HC10 mAb (IgG2a) binding to β2m-free heavy chains of HLA-B and -C alleles and to $B27_2$ was a gift from Dr. Hidde Ploegh (MIT, MA). HD5 mAb (in-house) antibody against B27 open conformer homodimers. Mouse IgG1 κ Isotype control (Biolegend). Anti-Her2neu mAb (Trastuzumab, Roche). Anti-β2-microglobulin antibody (Abcam) to detect human β2m by western blot.

Flow Cytometry of Leukocytes

Intracellular cytokine staining (ICS) for detection of FoxP3+ Treg cells was performed using 1% paraformaldehyde, permeabilized with 0.1% saponin in FACS buffer, and stained with primary antibodies (FoxP3, CD4 and CD3).

Intracellular cytokine staining (ICS) for stimulating leukocytes was performed with Phorbol myristate acetate (PMA) and ionomycin (both at 0.5 μg/mL), in the presence of GolgiPlug™ (BD bioscience) for 5 hours.

Flow cytometry analysis was performed using a FACS canto II (BD Bioscience) and data were analysed using FlowJo version 7.6.4.

Production of HLA-Complexes for In Vitro Tests

HLA-B*2705 open conformer homodimer and heterotrimer complexes were refolded by limiting dilution with or without β2m in the presence of influenza nucleoprotein NP383-391 peptide epitope SRYWAIRTR (SEQ ID NO 174) or EBV EBNA3C epitope RRIYDLIEL (SEQ ID NO 175). Control HLA-B8 heterotrimeric complex was refolded with hCMVpp65 (TPRTGGGAM; SEQ ID NO 176). Streptavidin or Streptavidin-PE (Life technologies) was used to build HLA-tetramers. Biotinylated BSA (Sigma) was used in control tetramers and in combinations with HLA complexes.

Generation of Tregs

To induce expression of Foxp3 in murine $CD4^+$ T cells, we harvested spleen cells from F344FoxP3$^{EGFP}$ mice. Splenocytes were sorted to obtain $CD4^+$ T naive cells. Cells were then cultured for 96 h at $10^5$ cells/200 μL/well in 96-well plates with coated 5 μg/mL anti-CD3mAb (eBioscience), soluble 2 μg/mL anti-CD28 mAb (Biolegend), 10 μg/mL of TGF-β1 (R&D systems) and 100 IU/mL of IL-2 (R&D systems).

To expand human nTregs, we first isolated PBMCs from a blood buffy coat by ficoll extraction. Then we isolated $CD4^+$ $CD25^+$ cells using the Regulatory T cell Dynabeads kit (Invitrogen), and further expanded them using the Human Treg Expander kit (Invitrogen) following instructions from the manual. Cells were cultured in complete RPMI for 8 days with the addition of 500 IU of IL-2 every second day.

iTreg Induction in the Presence of $B27_2$ Tetramers

Murine naive $CD4^+$ T cells in optimal culture conditions for iTreg conversion were incubated in the presence of 0.5 μg of $B27_2$-Tet, HLA-B27-Tet and HLA-B8-Tet for 72 h. iTreg conversion was measured by flow cytometry.

Suppression Assay $CD4^+$ or $CD8^+$ T-effector cells were purified PBMCs from either mouse or human (Mouse Naïve $CD4^+$ T Cell Isolation Kit—Easy Sep; Dynabeads® FlowComp™ Mouse CD8— life technologies; Dynabeads® CD8 human—Life Technologies) and labelled with 10 μM cell trace violet proliferation stain (Molecular Probes). Tregs ($2.5 \times 10^4$) cells and T-effector cells ($2.5 \times 10^4$) were cultured in 96 wells U-bottomed plates with coated CD3 (eBioscience) (3 μg/mL) and soluble CD28 (eBioscience) (1 μg/mL) antibody for 96 hrs. Proliferation of T-effector cells was measured using a FACS canto II and data were analysed using proliferation analysis software from FlowJo version 7.6.4.

Production, Purification and Re-Folding of $B27_2$-Fc

Recombinant production of $B27_2$-β2m-Fc was achieved by inserting the alpha 1, 2 and 3 domains of HLA-B27 into a human IgG4-Fc vector (InvivoGen), and the human β2-microglobulin (β2m) in a separate vector. Production of recombinant $B27_2$-β2m-Fc was performed by co-transfection of B27-Fc-vector and β2m-vector into Chinese hamster ovary (CHO) cells. Production of $B27_2$-β2m-Fc was outsourced to Evitria AG.

Purification of $B27_2$-β2m-Fc was performed using conventional protocols for antibody purification. Production of $B27_2$-Fc was performed with the addition of a denaturing step to remove β2m from the $B27_2$-β2m-Fc complex.

Briefly, the capture step of $B27_2$-β2m-Fc was performed after running supernatants (5 mL/min) through protein-G columns (Amersham Pharmacia). Intermediate purification steps were performed by eluting the $B27_2$-β2m-Fc from protein G-columns using elution buffer (100 mM glycine, pH 2.0), and recovering fractions in 8M Urea, 100 mM Tris-HCl pH 8.0, and 5 mM β-mercaptoethanol (BME). The $1^{st}$ Polishing step was to separate B27-Fc free-heavy chains fractions from β2m by either size exclusion chromatography (SEC) using superdex 200 prep grade or Sephacryl S-100 HR (GE Lifescience) with an AKTA system (GE Lifescience), or by dialysis with membranes of 30 KDa or 50 KDa pore size (Millipore). The recovered B27 free-heavy chains from both protocols were re-folded by the dilution method after pulsation of the B27 free-heavy chains at 3 times with intervals of 8 hours each in 100 times volume of refolding buffer (50 mM Tris-HCl pH8.5, 500 mM L-Arginine, 1 mM EDTA, 0.15 mM NaCl, 1% Sucrose, 0.01% polysorbate-80, 1 mM GSH, and 0.1 mM GSSH). The $2^{nd}$ Polishing step by SEC was performed to remove further impurities and to buffer exchange newly recovered fractions of $B27_2$-Fc molecules into dilution buffer (Tris 50 mM pH8.0, NaCl 150 mM, 1% Sucrose, and 0.01% polysorbate-80). Purified solutions of $B27_2$-Fc were filter sterilized using 0.2 am membranes (Millipore).

Fractions $B27_2$-β2m-Fc complexes and $B27_2$-Fc were analysed by SDS polyacrylamide gel electrophoresis (SDS-PAGE) and western blot using HC10 (specific for HLA-free-heavy chains) antibodies. β2m western blots were performed in denaturing conditions (10 mM DTT).

Checkpoint inhibitor antibodies CTLA4 clone 9H10 (tested in EG.7 and EMT6 syngeneic models), CTLA4 clone 9D9 (tested in Pan02 syngeneic model), and PD-1 clone RMP1-14 were obtained from Bio X Cell Co.

Full and Partial Sequences of HLA-B27 Alleles

Functional domains of the full length HLA-B27 alpha chain from N-terminus to C-terminus are: Signal peptide, alpha 1, alpha 2, alpha 3 (alpha domains 1-3 are underlined; alpha 2 is set in bold), transmembrane domain and cytoplasmic tail.

For example SEQ ID NO. 8 comprises:

a signal domain

SEQ ID NO. 1.
MRVTAPRTLLLLLWGAVALTETWA, an alpha 1 domain

SEQ ID NO. 2.
GSHSMRYFHTSVSRPGRGEPRFITVGYVDDTLEVREDSDAASPREEPRA

PWIEQEGPEYWDRETQICKAKAQTDRENLRIALRYYNQSEA, an alpha 2 domain

SEQ ID NO. 3.
GSHTLQNMYGCDVGPDGRLLRGYHQDAYDKDYIALNEDLSSWTAADTA
AQITQRKWEAARVAEQLRAYLEGECVEWLRRYLENGKETLQRA, an alpha 3 domain SEQ ID NO. 4.
DPPKTHVTHHPISDHEATLRCWALGFYPAEITLTWQRDGEDQTQDTELV
ETRPAGDRTFQKWAAVVVPSGEEQRYTCHVQHEGLPKPLTLRWEPSSQS
TVPIV, and a transmembrane domain and a cytoplasmic tail

SEQ ID NO. 5.
GIVAGLAVLAVVVIGAVVAAVMCRRKSSGGKGGSYSQAACSDSAQGSDVSLTA.

>HLA-B2705 280 aa

SEQ ID NO. 6.
GSHSMRYFHTSVSRPGRGEPRFITVGYVDDTLFVRFDSDAASPREEPRAPWIEQEGPEYWDRETQICKAKAQTDR
EDLRTLLRYYNQSEAGSHTLQNMYGCDVGPDGRLLRGYHQDAYDGKDYIALNEDLSSWTAADTAAQITQRKWEAA
RVAEQLRAYLEGECVEWLRRYLENGKETLQRADPPKTHVTHHPISDHEATLRCWALGFYPAEITLTWQRDGEDQT
QDTELVETRPAGDRTFQKWAAVVVPSGEEQRYTCHVQHEGLPKPLTLRWEPSSQS

>HLA:HLA00220 B*27:01 181 aa

SEQ ID NO. 7.
SHSMRYFHTSVSRPGRGEPRFITVGYVDDTLFVRFDSDAASPREEPRAPWIEQEGPEYWDRETQICKAKAQTYRE
NLRTALRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA00221 B*27:02:01 362 aa

SEQ ID NO. 8.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRENLRIALRYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA06955 B*27:02:02 181 aa

SEQ ID NO. 9.
SHSMRYFHTSVSRPGRGEPRFITVGYVDDTLFVRFDSDAASPREEPRAPWIEQEGPEYWDRETQICKAKAQTDRE
NLRIALRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA00222 B*27:03 362 aa

SEQ ID NO. 10.
MRVTAPRTLLLLLWGAVALTETWAGSHSMRYFHTSVSRPGRGEPRFITVGYVDDTLFVRFDSDAASPREEPRAPW
IEQEGPEHWDRETQICKAKAQTDREDLRTLLRYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA00223 B*27:04:01 362 aa

SEQ ID NO. 11.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRESLRTLLRYYNQSEAGSHTLQNMYGCDVGPDGRLLRGYHQDAYDGKDYIAL
NEDLSSWTAADTAAQITQRKWEAAREAEQLRAYLEGECVEWLRRYLENGKETLQRADPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

-continued

>HLA:HLA02246 B*27:04:02 181 aa
SEQ ID NO. 12.
SHSMRYFHTSVSRPGRGEPRFITVGYVDDTLFVRFDSDAASPREEPRAPWIEQEGPEYWDRETQICKAKAQTDRE
SLRTLLRYYNQSEA**GSHTLQNMYGCDVGPDGRLLRGYHQDAYDGKDYIALNEDLSSWTAADTAAQITQRKWEAAR
EAEQLRAYLEGECVEWLRRYLENGKETLQRA**

>HLA:HLA03987 B*27:04:03 181 aa
SEQ ID NO. 13.
SHSMRYFHTSVSRPGRGEPRFITVGYVDDTLFVRFDSDAASPREEPRAPWIEQEGPEYWDRETQICKAKAQTDRE
SLRTLLRYYNQSEA**GSHTLQNMYGCDVGPDGRLLRGYHQDAYDGKDYIALNEDLSSWTAADTAAQITQRKWEAAR
EAEQLRAYLEGECVEWLRRYLENGKETLQRA**

>HLA:HLA10469 B*27:04:04 337 aa
SEQ ID NO. 14.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRESLRTLLRYYNQSEA**GSHTLQNMYGCDVGPDGRLLRGYHQDAYDGKDYIAL
NEDLSSWTAADTAAQITQRKWEAAREAEQLRAYLEGECVEWLRRYLENGKETLQRA**DPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA00225 B*27:05:02 362 aa
SEQ ID NO. 15.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA00226 B*27:05:03 181 aa
SEQ ID NO. 16.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA01179 B*27:05:04 206 aa
SEQ ID NO. 17.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**

>HLA:HLA01642 B*27:05:05 298 aa
SEQ ID NO. 18.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRW

>HLA:HLA01635 B*27:05:06 181 aa
SEQ ID NO. 19.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA01985 B*27:05:07 337 aa
SEQ ID NO. 20.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL

-continued

NEDLSSWTAADTAAQITQRKWEAARVAEQLRAYLEGECVEWLRRYLENGKETLQRADPPKTHVTHHPISDHEATL

RCWALGFYPAEITLTWQRDGEDQTQDTELVETRPAGDRTFQKWAAVVVPSGEEQRYTCHVQHEGLPKPLTLRWEP

SSQSTVPIVGIVAGLAVLAVVVIGAVVAAVMCRRKSS

>HLA:HLA02100 B*27:05:08 181 aa
SEQ ID NO. 21.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02218 B*27:05:09 181 aa
SEQ ID NO. 22.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02826 B*27:05:10 296 aa
SEQ ID NO. 23.

GAVALTETWAGSHSMRYFHTSVSRPGRGEPRFITVGYVDDTLFVRFDSDAASPREEPRAPWIEQEGPEYWDRETQ

ICKAKAQTDREDLRTLLRYYNQSEAGSHTLQNMYGCDVGPDGRLLRGYHQDAYDGKDYIALNEDLSSWTAADTAA

QITQRKWEAARVAEQLRAYLEGECVEWLRRYLENGKETLQRADPPKTHVTHHPISDHEATLRCWALGFYPAEITL

TWQRDGEDQTQDTELVETRPAGDRTFQKWAAVVVPSGEEQRYTCHVQHEGLPKPLTLRWEPSSQSTVPIVG

>HLA:HLA04054 B*27:05:11 181 aa
SEQ ID NO. 24.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA04197 B*27:05:12 181 aa
SEQ ID NO. 25.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA04509 B*27:05:13 181 aa
SEQ ID NO. 26.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA05400 B*27:05:14 181 aa
SEQ ID NO. 27.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA05477 B*27:05:15 181 aa
SEQ ID NO. 28.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA05925 B*27:05:16 181 aa
SEQ ID NO. 29.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA06926 B*27:05:17 181 aa
SEQ ID NO. 30.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA07634 B*27:05:18 362 aa
SEQ ID NO. 31.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA07901 B*27:05:19 181 aa
SEQ ID NO. 32.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA08661 B*27:05:20 181 aa
SEQ ID NO. 33.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA08979 B*27:05:21 181 aa
SEQ ID NO. 34.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA08980 B*27:05:22 181 aa
SEQ ID NO. 35.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA09882 B*27:05:23 325 aa
SEQ ID NO. 36.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGA

>HLA:HLA09884 B*27:05:24 181 aa
SEQ ID NO. 37.
SHSMRYFHTSVSRPGRGEPRFITVGYVDDTLFVRFDSDAASPREEPRAPWIEQEGPEYWDRETQICKAKAQTDRE
DLRTLLRYYNQSEA**GSHTLQNMYGCDVGPDGRLLRGYHQDAYDGKDYIALNEDLSSWTAADTAAQITQRKWEAAR
VAEQLRAYLEGECVEWLRRYLENGKETLQRA**

>HLA:HLA10198 B*27:05:25 298 aa
SEQ ID NO. 38.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL

-continued

NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRW

>HLA:HLA10269 B*27:05:26 273 aa
SEQ ID NO. 39.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRADPPKTHVTHHPISDHEATLRCWALGFYPAEITLTWQRDGEDQTQ
DTELVETRPAGDRTFQKWAAVVVPSGEEQRYTCHVQHEGLPKPLTLRW

>HLA:HLA11005 B*27:05:27 181 aa
SEQ ID NO. 40.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA11226 B*27:05:28 181 aa
SEQ ID NO. 41.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA00227 B*27:06 362 aa
SEQ ID NO. 42.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRESLRTLLRYYNQSEAGSHTLQNMYGCDVGPDGRLLRGYDQYAYDGKDYIAL
NEDLSSWTAADTAAQITQRKWEAAREAEQLRAYLEGECVEWLRRYLENGKETLQRADPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA00228 B*27:07:01 362 aa
SEQ ID NO. 43.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQSMYGCDVGPDGRLLRGHNQYAYDGKDYIAL
NEDLRSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA07340 B*27:07:02 273 aa
SEQ ID NO. 44.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQSMYGCDVGPDGRLLRGHNQYAYDGKDYIALNEDLRSWTAADTAAQITQRKWEAAR
VAEQLRAYLEGECVEWLRRYLENGKETLQRADPPKTHVTHHPISDHEATLRCWALGFYPAEITLTWQRDGEDQTQ
DTELVETRPAGDRTFQKWAAVVVPSGEEQRYTCHVQHEGLPKPLTLRW

>HLA:HLA08329 B*27:07:03 181 aa
SEQ ID NO. 45.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQSMYGCDVGPDGRLLRGHNQYAYDGKDYIALNEDLRSWTAADTAAQITQRKWEAAR
VAEQLRAYLEGECVEWLRRYLENGKETLQRA

>HLA:HLA09883 B*27:07:04 181 aa
SEQ ID NO. 46.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQSMYGCDVGPDGRLLRGHNQYAYDGKDYIALNEDLRSWTAADTAAQITQRKWEAAR
VAEQLRAYLEGECVEWLRRYLENGKETLQRA

-continued

>HLA:HLA00229 B*27:08 362 aa
SEQ ID NO. 47.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRESLRNLRGYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA00230 B*27:09 362 aa
SEQ ID NO. 48.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQHAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA00231 B*27:10 362 aa
SEQ ID NO. 49.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL
NEDLSSWTAADTAAQITQRKWEAAREAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA08911 B*27:100 273 aa
SEQ ID NO. 50.
SHSMRYFHTSVSRPGRGEPRFITVGYVDDTLFVRFDSDAASPREEPRAPWIEQEGPEYWDRETQICKAKAQTDRE
SLRTLLRYYNQSEAGSHTLQNMYGCDMGPDGRLLRGYHQDAYDGKDYIALNEDLSSWTAADTAAQITQRKWEAAR
EAEQLRAYLEGECVEWLRRYLENGKETLQRADPPKTHVTHHPISDHEATLRCWALGFYPGEITLTWQRDGEDQTQ
DTELVETRPAGDRTFQKWAAVVVPSGEEQRYTCHVQHEGLPKPLTLRW

>HLA:HLA09308 B*27:101 181 aa
SEQ ID NO. 51.
SHSMRYFHTSVSRPGRGEPRFITVGYVDDTLFVRFDSDAASPREEPRAPWIEQEGPEYWDRETQICKAQAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA09309 B*27:102 181 aa
SEQ ID NO. 52.
SHSMRYFHTSVSRPGRGEPRFITVGYVDDTLFVRFDSDAASPREEPRAPWIEQEGPEYWDRETQICKAKAQTDRE
NLRIALRYYNQSEAGSHTLQNMYGCDVGPDGRLLRGYNQYAYDGKDYIALNEDLRSWTAADTAAQITQRKWEAAR
VAEQLRAYLEGECVEWLRRYLENGKETLQRA

>HLA:HLA09326 B*27:103 273 aa
SEQ ID NO. 53.
SHSMRYFHTSVSRPGCGEPRFITVGYVDDTLFVRFDSDAASPREEPRAPWIEQEGPEYWDRETQICKAKAQTDRE
SLRTLLRYYNQSEAGSHTLQNMYGCDVGPDGRLLRGYHQDAYDGKDYIALNEDLSSWTAADTAAQITQRKWEAAR
EAEQLRAYLEGECVEWLRRYLENGKETLQRADPPKTHVTHHPISDHEATLRCWALGFYPGEITLTWQRDGEDQTQ
DTELVETRPAGDRTFQKWAAVVVPSGEEQRYTCHVQHEGLPKPLTLRW

>HLA:HLA09426 B*27:104 181 aa
SEQ ID NO. 54.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVAPDGRLLRGYHQDAYDGKDYIALNEDLSSWTAADTAAQITQRKWEAAR
VAEQLRAYLEGECVEWLRRYLENGKETLQRA

-continued

\>HLA:HLA09452 B\*27:105 273 aa

SEQ ID NO. 55.

SHSMRYFHTSVSRPGRGEPRFITVGYVDDTLFVRFDSDAASPREEPRAPWIEQEGPEYWDRETQICKAKAQTDRE
SLRTLLRYYNQSEA**GSHTLQNMYGCDVGPDGRLLHGYHQDAYDGKDYIALNEDLSSWTAADTAAQITQRKWEAAR
EAEQLRAYLEGECVEWLRRYLENGKETLQRA**DPPKTHVTHHPISDHEATLRCWALGFYPGEITLTWQRDGEDQTQ
DTELVETRPAGDRTFQKWAAVVVPSGEEQRYTCHVQHEGLPKPLTLRW

\>HLA:HLA09703 B\*27:106 181 aa

SEQ ID NO. 56.

SHSMRYFHTAMSRPGRGEPRFITVGYVDDTLFVRFDSDAASPREEPRAPWIEQEGPEYWDRETQICKAKAQTDRE
SLRTLLRYYNQSEA**GSHTLQNMYGCDVGPDGRLLRGYDQYAYDGKDYIALNEDLSSWTAADTAAQITQRKWEAAR
EAEQLRAYLEGECVEWLRRYLENGKETLQRA**

\>HLA:HLA10159 B\*27:107 181 aa

SEQ ID NO. 57.

SHSMRYFHTSVSRPGRGEPRFITVGYVDDTLFVRFDSDAASPREEPRAPWIEQEGPEYWDRETQICKAKAQTDRE
SLRTLLRYYNQSEA**GSHTLQNMYGCDLGPDGRLLRGYDQSAYDGKDYIALNEDLSSWTAADTAAQITQRKWEAAR
EAEQLRAYLEGECVEWLRRYLENGKETLQRA**

\>HLA:HLA10402 B\*27:108 181 aa

SEQ ID NO. 58.

SHSMRYFHTSVSRPGRGEPRFITVGYVDDTLFVRFDSDAASPREEPRAPWIEQEGPEYWDRETQICKAKAQTDRE
SLRTLLRYYNQSEA**GSHTLQNMYGCDVGPDGRLLRGYHQDAYDGKDYIALNEDLSSWTAADTAAQITQRKWEAAR
EAEQRRAYLEGECVEWLRRYLENGKETLQRA**

\>HLA:HLA10468 B\*27:109 337 aa

SEQ ID NO. 59.

MRVTAPRTLLLLLWGAVALTETWAGSHSMRYFHTSVSRPGRGEPRFITVGYVDDTLFVRFDSDAASPREEPRAPW
IEQEGPEYWDRETRICKAKAQTDRESLRTLLRYYNQSEA**GSHTLQNMYGCDVGPDGRLLRGYHQDAYDGKDYIAL
NEDLSSWTAADTAAQITQRKWEAAREAEQLRAYLEGECVEWLRRYLENGKETLQRA**DPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

\>HLA:HLA00232 B\*27:11 362 aa

SEQ ID NO. 60.

MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRESLRTLLRYYNQSEA**GSHTLQSMYGCDVGPDGRLLRGHNQYAYDGKDYIAL
NEDLRSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

\>HLA:HLA10470 B\*27:110 337 aa

SEQ ID NO. 61.

MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRENLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

\>HLA:HLA10698 B\*27:111 337 aa

SEQ ID NO. 62.

MRVTAPRTLLLLLWGAVALTETWAGSHSMRYFHTSVSRPGCGEPRFITVGYVDDTLFVRFDSDAASPREEPRAPW
IEQEGPEHWDRETQICKAKAQTDREDLRTLLRYYNQSEA**GSHTLQNMYGCDVGPDGRLLRGYHQDAYDGKDYIAL
NEDLSSWTAADTAAQITQRKWEAARVAEQLRAYLEGECVEWLRRYLENGKETLQRA**DPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

-continued

>HLA:HLA10699 B*27:112 337 aa
SEQ ID NO. 63.
MRVTAPRTLLLLLWGAVALTETWAVSHSMRYFHTSVSRPGRGEPRFITVGYVDDTLFVRFDSDAASPREEPRAPW
IEQEGPEYWDRETQICKAKAQTDRESLRTLLRYYNQSEAGSHTLQNMYGCDVGPDGRLLRGYHQDAYDGKDYIAL
NEDLSSWTAADTAAQITQRKWEAAREAEQLRAYLEGECVEWLRRYLENGKETLQRADPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA10700 B*27:113 337 aa
SEQ ID NO. 64.
MRVTAPRTLLLLLWGAVALTETWAGSHSMGYFHTSVSRPGRGEPRFITVGYVDDTLFVRFDSDAASPREEPRAPW
IEQEGPEYWDRETQICKAKAQTDRESLRTLLRYYNQSEAGSHTLQNMYGCDVGPDGRLLRGYHQDAYDGKDYIAL
NEDLSSWTAADTAAQITQRKWEAAREAEQLRAYLEGECVEWLRRYLENGKETLQRADPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA10701 B*27:114 337 aa
SEQ ID NO. 65.
MRVTAPRTLLLLLWGAVALTETWAGSHSMRYFHTSVSRPGRGEPRFITVGYVDDTLFVRFDSDAASPREEPRGPW
IEQEGPEYWDRETQICKAKAQTDRESLRTLLRYYNQSEAGSHTLQNMYGCDVGPDGRLLRGYHQDAYDGKDYIAL
NEDLSSWTAADTAAQITQRKWEAAREAEQLRAYLEGECVEWLRRYLENGKETLQRADPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA10702 B*27:115 337 aa
SEQ ID NO. 66.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDRESLRTLLRYYNQSEAGSHTLQNMYGCDVGPDGRLLRGYHQDAYDGKDYIAL
NEDLSSWTAADTAAQITQRKWEAAREAEQWRAYLEGECVEWLRRYLENGKETLQRADPPKTHVTHHPISDHEATL
RCWALGFYPGEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA10703 B*27:116 337 aa
SEQ ID NO. 67.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLHYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA10705 B*27:117 337 aa
SEQ ID NO. 68.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL
NKDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA10906 B*27:118 181 aa
SEQ ID NO. 69.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLKNGKETLQRA

-continued

>HLA:HLA11002 B*27:119 181 aa

SEQ ID NO. 70.
SHSMRYFHTSVSRPGRGEPRFITVGYVDDTLFVRFDSDAASPREEPRAPWIEQEGPEYWDRETQICKTNTQTYRE
NLRIALRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA00233 B*27:12 341 aa

SEQ ID NO. 71.
MRVTAPRTLLLLLWGAVALTETWAGSHSMRYFHTSVSRPGRGEPRFITVGYVDDTLFVRFDSDAASPREEPRAPW
IEQEGPEYWDRETQICKTNTQTDRESLRNLRGYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKG

>HLA:HLA11003 B*27:120 181 aa

SEQ ID NO. 72.
SHSMRYFHTSVSRPGRGEPRFITVGYVDDTLFVRFDSDAASPREEPRAPWIEQEGPEYWDRETQICKAKAQTDRE
SLRTLLRYYNQSEAGSHTLQNMYGCDVGPDGRLLRGYHQDAYDGKDYIALNEDLSSWTAADTAAQITQRKWEAAR
EAEQLRAYLEGECVEWLCRYLENGKETLQRA

>HLA:HLA11004 B*27:121 181 aa

SEQ ID NO. 73.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENRKETLQRA

>HLA:HLA11006 B*27:122 181 aa

SEQ ID NO. 74.
SHSMRYFHTSVSRPGRGEPRFITVGYVDDTLFVRFDSDAASPREEPRAPWIEQEGPEYWDRETQICKAKAQTDRE
DLRTLLRYCNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA11225 B*27:123 181 aa

SEQ ID NO. 75.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDRRLLRGYHQDAYDGKDYIALNEDLSSWTAADTAAQITQRKWEAAR
VAEQLRAYLEGECVEWLRRYLENGKETLQRA

>HLA:HLA11227 B*27:124 181 aa

SEQ ID NO. 76.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWSAADTAAQITQRKWEAAR
VAEQLRAYLEGECVEWLRRYLENGKETLQRA

>HLA:HLA11200 B*27:125 337 aa

SEQ ID NO. 77.
MRVTAPRTLLLLLWGAVALTETWaGSHSMRYFHTSVSRPGRGEPRFITVGYVDDTLFVRFDSDAASPREEPRAPW
IEQEGPEYWDRETQICKAKAQTDRESLRTLLRYYNQSEAGSHTLQRMYGCDVGPDGRLLRGHNQYAYDGKDYIAL
NEDLRSWTAADTAAQISQRKLEAARVAEQLRAYLEGECVEWLRRYLENGKDKLERADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSS

>HLA:HLA11648 B*27:126 181 aa

SEQ ID NO. 78.
SHSMRYFHTSVSRPGRGEPRFITVGYVDDTLFVRFDSDAASPREEPRAPWIEQEGPEYWDRETQICKAKAQTDRE
NLRIALRYYNQSEAGSHTLQNMYGCDVGPDGRLLRGYHQDAYDGKDYIALNEDLSSWTAADTAAQITQRKWEAAR
VVEQLRAYLEGECVEWLRRYLENGKETLQRA

-continued

>HLA:HLA11649 B*27:127 181 aa
SEQ ID NO. 79.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHIIQRMYGCDVGPDGRLLRGYDQDAYDGKDYIALNEDLSSWTAADTAAQITQRKWEAAR
VAEQDRAYLEGLCVESLRRYLENGKETLQRA

>HLA:HLA11729 B*27:128 206 aa
SEQ ID NO. 80.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL
NEDLSSWTAADTAAQITQRKWEAARVAEQLRAYLEGECVEWLRRYLENGKDTLQRA

>HLA:HLA11818 B*27:129 181 aa
SEQ ID NO. 81.
SHSMRYFHTSVSRPGRGEPRFITVGYVDDTLFVRFDSDAASPREEPRAPWIEQEGPEYWDRETQICKANTQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA00234 B*27:13 362 aa
SEQ ID NO. 82.
MRVTEPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA12037 B*27:130 181 aa
SEQ ID NO. 83.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTWQTMYGCDVGPDGRLLRGHNQYAYDGKDYIALNEDLRSWTAADTAAQITQRKWEAAR
VAEQLRAYLEGECVEWLRRYLENGKETLQRA

>HLA:HLA12072 B*27:131 362 aa
SEQ ID NO. 84.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTYRESLRTLLRYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA00235 B*27:14 206 aa
SEQ ID NO. 85.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTWQTMYGCDLGPDGRLLRGYHQDAYDGKDYIAL
NEDLSSWTAADTAAQITQRKWEAARVAEQLRAYLEGECVEWLRRYLENGKETLQRA

>HLA:HLA00236 B*27:15 181 aa
SEQ ID NO. 86.
SHSMRYFHTSVSRPGRGEPRFITVGYVDDTLFVRFDSDAASPREEPRAPWIEQEGPEYWDRETQICKAKAQTDRE
SLRTLLRYYNQSEAGSHTLQNMYGCDVGPDGRLLRGYHQDAYDGKDYIALNEDLSSWTAADTAAQITQRKWEAAR
EAEQLRAYLEGTCVEWLRRYLENGKETLQRA

>HLA:HLA01056 B*27:16 181 aa
SEQ ID NO. 87.
SHSMRYFHTSVSRPGRGEPRFITVGYVDDTLFVRFDSDAASPREEPRAPWIEQEGPEYWDRETQICKTNTQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

\>HLA:HLA01130 B*27:17 362 aa

SEQ ID NO. 88.

MRVTAPRTLLLLLWGAVALTETW<u>AGSHSMRYFHTSVSRPGRGEPRFITVGYVDDTLFVRFDSDAASPREEPRAPW IEQEGPEFWDRETQICKAKAQTDREDLRTLLRYYNQSEAGSHTLQNMYGCDVGPDGRLLRGYHQDAYDGKDYIAL NEDLSSWTAADTAAQITQRKWEAARVAEQLRAYLEGECVEWLRRYLENGKETLQRADPPKTHVTHHPISDHEATL RCWALGFYPAEITLTWQRDGEDQTQDTELVETRPAGDRTFQKWAAVVVPSGEEQRYTCHVQHEGLPKPLTLRWEP SSQSTVPIV</u>GIVAGLAVLAVVVIGAVVAAVMCRRKSSGGKGGSYSQAACSDSAQGSDVSLTA

\>HLA:HLA01143 B*27:18 206 aa

SEQ ID NO. 89.

MRVTAPRTLLLLLWGAVALTETWv<u>AGSHSMRYFHTSVSRPGRGEPRFITVGYVDDTLFVRFDSDAASPREEPRAPW IEQEGPEYWDRETQISKTNTQTYRESLRNLRGYYNQSEAGSHTLQNMYGCDVGPDGRLLRGYHQDAYDGKDYIAL NEDLSSWTAADTAAQITQRKWEAAREAEQLRAYLEGECVEWLRRYLENGKETLQRA</u>

\>HLA:HLA01147 B*27:19 181 aa

SEQ ID NO. 90.

<u>SHSMRYFHTSVSRPGRGEPRFITVGYVDDTLFVRFDSDAASPREEPRAPWIEQEGPEYWDRETQICKAKAQTDRE DLRTLLRYYNQSEAGSHIIQRMYGCDVGPDGRLLRGYHQDAYDGKDYIALNEDLSSWTAADTAAQITQRKWEAAR VAEQLRAYLEGECVEWLRRYLENGKETLQRA</u>

\>HLA:HLA01173 B*27:20 273 aa

SEQ ID NO. 91.

<u>SHSMRYFHTSVSRPGRGEPRFITVGYVDDTLFVRFDSDAASPREEPRAPWIEQEGPEYWDRETQICKAKAQTDRE SLRTLLRYYNQSEAGSHTLQNMYGCDVGPDGRLLRGHNQYAYDGKDYIALNEDLRSWTAADTAAQITQRKWEAAR EAEQLRAYLEGECVEWLRRYLENGKETLQRADPPKTHVTHHPISDHEATLRCWALGFYPGEITLTWQRDGEDQTQ DTELVETRPAGDRTFQKWAAVVVPSGEEQRYTCHVQHEGLPKPLTLRW</u>

\>HLA:HLA01277 B*27:21 181 aa

SEQ ID NO. 92.

<u>SHSMRYFHTSVSRPGRGEPRFITVGYVDDTLFVRFDSDAASPREEPRAPWIEQEGPEYWDRETQICKAKAQTDRE SLRTLLRYYNQSEAGSHTLQRMYGCDVGPDGRLLRGYDQYAYDGKDYIALNEDLSSWTAADTAAQITQRKWEAAR EAEQLRAYLEGECVEWLRRYLENGKETLQRA</u>

\>HLA:HLA01348 B*27:23 181 aa

SEQ ID NO. 93.

<u>SHSMRYFHTSVSRPGRGEPRFITVGYVDDTLFVRFDSDAASPREEPRAPWIEQEGPEYWDRNTQIFKTNTQTYRE SLRTLLRYYNQSEAGSHTLQNMYGCDVGPDGRLLRGYHQDAYDGKDYIALNEDLSSWTAADTAAQITQRKWEAAR VAEQLRAYLEGECVEWLRRYLENGKETLQRA</u>

\>HLA:HLA01504 B*27:24 362 aa

SEQ ID NO. 94.

MRVTAPRTLLLLLWGAVALTETW<u>AGSHSMRYFHTSVSRPGRGEPRFITVGYVDDTLFVRFDSDAASPREEPRAPW IEQEGPEYWDRETQICKAKAQTDRESLRTLLRYYNQSEAGSHTLQSMYGCDVGPDGRLLRGHNQYAYDGKDYIAL NEDLRSWTAADTAAQISQRKWEAAREAEQLRAYLEGECVEWLRRYLENGKETLQRADPPKTHVTHHPISDHEATL RCWALGFYPGEITLTWQRDGEDQTQDTELVETRPAGDRTFQKWAAVVVPSGEEQRYTCHVQHEGLPKPLTLRWEP SSQSTVPIV</u>GIVAGLAVLAVVVIGAVVAAVMCRRKSSGGKGGSYSQAACSDSAQGSDVSLTA

\>HLA:HLA01529 B*27:25 362 aa

SEQ ID NO. 95.

MRVTAPRTLLLLLWGAVALTETW<u>AGSHSMRYFHTSVSRPGRGEPRFITVGYVDDTLFVRFDSDAASPREEPRAPW IEQEGPEYWDRETQICKAKAQTDRESLRTLLRYYNQSEAGSHTLQNMYGCDVGPDGRLLRGYHQDAYDGKDYIAL NEDLSSWTAADTAAQITQRKWEAAREAEQWRAYLEGLCVEWLRRYLENGKETLQRADPPKTHVTHHPISDHEATL RCWALGFYPGEITLTWQRDGEDQTQDTELVETRPAGDRTFQKWAAVVVPSGEEQRYTCHVQHEGLPKPLTLRWEP SSQSTVPIV</u>GIVAGLAVLAVVVIGAVVAAVMCRRKSSGGKGGSYSQAACSDSAQGSDVSLTA

-continued

```
>HLA:HLA01952 B*27:26 181 aa
                                                           SEQ ID NO. 96.
SHSMRYFHTSVSRPGRGEPRFITVGYVDDTLFVRFDSDAASPREEPRAPWIEQEGPEYWDRETQICKAQAQTDRE

SLRNLRGYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02023 B*27:27 181 aa
                                                           SEQ ID NO. 97.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGHNQYAYDGKDYIALNEDLSSWTAADTAAQITQRKWEAAR

VAEQLRAYLEGECVEWLRRYLENGKETLQRA

>HLA:HLA02118 B*27:28 181 aa
                                                           SEQ ID NO. 98.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGTCVEWLRRHLENGKETLQRA

>HLA:HLA02171 B*27:29 181 aa
                                                           SEQ ID NO. 99.
SHSMRYFHTSVSRPGRGEPRFITVGYVDDTLFVRFDSDAASPREEPRAPWIEQEGPEYWDRETQISKTNTQTYRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02238 B*27:30 181 aa
                                                           SEQ ID NO. 100.
SHSMRYFHTSVSRPGRGEPRFITVGYVDDTLFVRFDSDAASPREEPRAPWIEQEGPEYWDRETQICKAKAQTDRE

NLRIALRYYNQSEAGSHIIQRMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02301 B*27:31 181 aa
                                                           SEQ ID NO. 101.
SHSMRYFHTSVSRPGRGEPRFITVGYVDDTLFVRFDSDAASPREEPRAPWIEQEGPEYWDRETQICKAQAQTDRE

SLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02370 B*27:32 362 aa
                                                           SEQ ID NO. 102.
MRVTAPRTLLLLLWGAVALTETWAGSHSMRYFHTSVSRPGRGEPRFITVGYVDDTLFVRFDSDAASPREEPRAPW

IEQEGPEYWDRETQICKAKAQTDREDLRTLLRYYNQSEAGSHTLQSMYGCDVGPDGRLLRGYHQDAYDGKDYIAL

NEDLSSWTAADTAAQITQRKWEAARVAEQLRAYLEGECVEWLRRYLENGKETLQRADPPKTHVTHHPISDHEATL

RCWALGFYPAEITLTWQRDGEDQTQDTELVETRPAGDRTFQKWAAVVVPSGEEQRYTCHVQHEGLPKPLTLRWEP

SSQSTVPIVGIVAGLAVLAVVVIGAVVAAVMCRRKSSGGKGGSYSQAACSDSAQGSDVSLTA

>HLA:HLA02437 B*27:33 181 aa
                                                           SEQ ID NO. 103.
SHSMRYFHTSVSRPGRGEPRFITVGYVDDTLFVRFDSDAASPREEPRAPWIEQEGPEYWDRETQICKAKAQTDRE

SLRNLRGYYNQSEAGSHTLQSMYGCDVGPDGRLLRGHNQYAYDGKDYIALNEDLRSWTAADTAAQITQRKWEAAR

VAEQLRAYLEGECVEWLRRYLENGKETLQRA

>HLA:HLA02473 B*27:34 181 aa
                                                           SEQ ID NO. 104.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQSMYGCDVGPDGRLLRGHDQYAYDGKDYIALNEDLRSWTAADTAAQITQRKWEAAR

VAEQLRAYLEGECVEWLRRYLENGKETLQRA
```

```
>HLA:HLA02499 B*27:35 337 aa
                                                         SEQ ID NO. 105.
MRVTAPRTLLLLLWGAVALTETWAGSHSMRYFHTSVSRPGRGEPRFITVGYVDDTLFVRFDSDAASPREEPRAPW

IEQEGPEYWDRETQICKAKAQTDREDLRTLLRYYNQSEAGSHTLQNMYGCDVGPDGRLLRGYNQFAYDGKDYIAL

NEDLSSWTAADTAAQITQRKWEAARVAEQLRAYLEGECVEWLRRYLENGKETLQRADPPKTHVTHHPISDHEATL

RCWALGFYPAEITLTWQRDGEDQTQDTELVETRPAGDRTFQKWAAVVVPSGEEQRYTCHVQHEGLPKPLTLRWEP

SSQSTVPIVGIVAGLAVLAVVVIGAVVAAVMCRRKSS

>HLA:HLA02513 B*27:36 302 aa
                                                         SEQ ID NO. 106.
SHSMRYFHTSVSRPGRGEPRFITVGYVDDTLFVRFDSDAASPREEPRAPWIEQEGPEYWDRETQICKAKAQTDRE

SLRTLLRYYNQSEAGSHTLQNMYGCDVGPDGRLLRGYHQDAYDGKDYIALNEDLRSWTAADTAAQISQRKLEAAR

VAEQLRAYLEGECVEWLRRYLENGKDKLERADPPKTHVTHHPISDHEATLRCWALGFYPAEITLTWQRDGEDQTQ

DTELVETRPAGDRTFQKWAAVVVPSGEEQRYTCHVQHEGLPKPLTLRWEPSSQSTVPIVGIVAGLAVLAVVVIGA

VV

>HLA:HLA02784 B*27:37 181 aa
                                                         SEQ ID NO. 107.
SHSMRYFYTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA02931 B*27:38 309 aa
                                                         SEQ ID NO. 108.
PRTLLLLLWGAVALTETWAGSHSMRYFHTSVSRPGRGEPRFITVGYVDDTLFVRFDSDAASPREEPRAPWIEQEG

PEYWDRETQICKAKAQTOREDLRTLLRYYNQSEAGSHTLQNMYGCDVGPDGRLLRGYHQDAYDGKDYIALNEDLS

SWTAADTAAQITQRKWEAARVAEQLRAYLEGLCVEWLRRYLENGKETLQRADPPKTHVTHHPISDHEATLRCWAL

GFYPAEITLTWQRDGEDQTQDTELVETRPAGDRTFQKWAAVVVPSGEEQRYTCHVQHEGLPKPLTLRWEPSSQST

VPIVGIVAG

>HLA:HLA03176 B*27:39 181 aa
                                                         SEQ ID NO. 109.
SHSMRYFHTSVSRPGRGEPRFITVGYVDDTLFVRFDSDAASPREEPRAPWIEQEGPEYWDRETQICKAKALTORE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA03200 B*27:40 181 aa
                                                         SEQ ID NO. 110.
SHSMRYFHTSVSRPGRGEPRFITVGYVDDTLFVRFDSDAASPREEPRAPWIEQEGPEYWDRETQICKAKAQTDRE

SLRNLRGYYNQSEAGSHTLQNMYGCDVGPDGRLLRGYHQDAYDGKDYIALNEDLSSWTAADTAAQITQRKWEAAR

EAEQLRAYLEGECVEWLRRYLENGKETLQRA

>HLA:HLA03276 B*27:41 181 aa
                                                         SEQ ID NO. 111.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGHDQSAYDGKDYIALNEDLSSWTAADTAAQITQRKWEAAR

VAEQLRAYLEGECVEWLRRYLENGKETLQRA

>HLA:HLA03278 B*27:42 181 aa
                                                         SEQ ID NO. 112.
SHSMRYFHTSVSRPGRGEPRFITVGYVDDTLFVRFDSDAASPREEPRAPWIEQEGPEYWDRETQICKAKAQTDRE

DLRNLRGYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA
```

-continued

>HLA:HLA03323 B*27:43 181 aa
SEQ ID NO. 113.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQSMYGCDVGSDGRLLRGHNQYAYDGKDYIALNEDLRSWTAADTAAQITQRKWEAAR
VAEQLRAYLEGECVEWLRRYLENGKETLQRA

>HLA:HLA03551 B*27:44 181 aa
SEQ ID NO. 114.
SHSMRYFHTSVSRPGRGEPRFITVGYVDDTLFVRFDSDAASPREEPRAPWIEQEGPEYWDRETQICKAKAQTYRE
SLRNLRGYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA03554 B*27:45 273 aa
SEQ ID NO. 115.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQRRAYLEGECVEWLRRYLENGKETLQRADPPKTHVTHHPISDHEATLRCWALGFYPAEITLTWQRDGEDQTQ
DTELVETRPAGDRTFQKWAAVVVPSGEEQRYTCHVQHEGLPKPLTLRN

>HLA:HLA03616 B*27:46 181 aa
SEQ ID NO. 116.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQYAYDGKDYIALNEDLSSWTAADTAAQITQRKWEAAR
VAEQLRAYLEGECVEWLRRYLENGKETLQRA

>HLA:HLA03659 B*27:47 362 aa
SEQ ID NO. 117.
MRVTAPRTLLLLLWGAVALTETWAGSHSMRYFHTSVSRPGRGEPRFITVGYVDDTLFVRFDSDAASPREEPRAPW
IEQEGPEYWDRETQICKAKAQTDREDLRTLLRYYNQSEAGSHTLQNMYGCDVGPDGRLLRGYHQDAYDGKDYIAL
NEDLSSWTAADTAAQITQRKWEAARVAEQDRAYLEGLCVESLRRYLENGKETLQRADPPKTHVTHHPISDHEVTL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVIGAVVAAVMCRRKSSGGKGGSYSQAACSDSAQGSDVSLTA

>HLA:HLA03661 B*27:48 181 aa
SEQ ID NO. 118.
SHSMRYFHTSVSRPGRGEPRFITVGYVDDTLFVRFDSDAASPREEPRAPWREQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA03677 B*27:49 181 aa
SEQ ID NO. 119.
SHSMRYFHTSVSRPGRGEPRFITVGYVDDTLFVRFDSDAASPREEPRAPWIEQEGPEYWDRETQICKAKAQTDRE
DLRTLFRYYNQSEAGSHTLQNNYGCDVGPDGRLLRGYHQDAYDGKDYIALNEDLSSWTAADTAAQITQRKWEAAR
VAEQLRAYLEGECVEWLRRYLENGKETLQRA

>HLA:HLA03712 B*27:50 181 aa
SEQ ID NO. 120.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVESLRRYLENGKETLQRA

>HLA:HLA03810 B*27:51 273 aa
SEQ ID NO. 121.
SHSMRYFHTSVSRPGRGEPRFITVGYVDDTLFVRFDSDAASPREEQRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRADPPKTHVTHHPISDHEATLRCWALGFYPAEITLTWQRDGEDQTQ
DTELVETRPAGDRTFQKWAAVVVPSGEEQRYTCHVQHEGLPKPLTLRN

>HLA:HLA03824 B*27:52 362 aa

SEQ ID NO. 122.
MRVTAPRTLLLLLWGAVALTETWAGSHSMRYFHTSVSRPGRGEPRFITVGYVDDTLFVRFDSDAASPRTEPRAPW
IEQEGPEYWDRETQICKAKAQTDREDLRTLLRYYNQSEAGSHTLQNMYGCDVGPDGRLLRGYHQDAYDGKDYIAL
NEDLSSWTAADTAAQITQRKWEAARVAEQLRAYLEGECVEWLRRYLENGKETLQRADPPKTHVTHHPISDHEATL
RCWALGFYPAEITLTWQRDGEDQTQDTELVETRPAGDRTFQKWAAVVVPSGEEQRYTCHVQHEGLPKPLTLRWEP
SSQSTVPIVGIVAGLAVLAVVVIGAVVAAVMCRRKSSGGKGGSYSQAACSDSAQGSDVSLTA

>HLA:HLA03952 B*27:53 181 aa

SEQ ID NO. 123.
SHSMRYFHTSVSRPGRGEPRFITVGYVDDTLFVRFDSDAASPREEPRAPWIEQEGPEYWDRETQICKAKAQTDRE
DLRIALRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA03955 B*27:54 181 aa

SEQ ID NO. 124.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDRRLLRGYHQDAYDGKDYIALNEDLSSWTAADTAAQITQRKWEAAR
EAEQLRAYLEGECVEWLRRYLENGKETLQRA

>HLA:HLA04048 B*27:55 181 aa

SEQ ID NO. 125.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTVAQITQRKWEAAR
VAEQLRAYLEGECVEWLRRYLENGKETLQRA

>HLA:HLA04053 B*27:56 181 aa

SEQ ID NO. 126.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAAGTAAQITQRKWEAAR
VAEQLRAYLEGECVEWLRRYLENGKETLQRA

>HLA:HLA04089 B*27:57 181 aa

SEQ ID NO. 127.
SHSMRYFHTSVSRPGRGEPRFITVGYVDDTLFVRFDSDAASPREEPRARWIEQEGPEYWDRETQICKAKAQTDRE
NLRIALRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA04175 B*27:58 181 aa

SEQ ID NO. 128.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQCA

>HLA:HLA04164 B*27:59N 71 aa

SEQ ID NO. 129.
SHSMRYFHTSVSRPGRGEPRFITVGYVDDTLFVRFDSDAASPREEPRAPWIEQEGPEYWDRETQICKAKAX

>HLA:HLA04443 B*27:60 181 aa

SEQ ID NO. 130.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQGKWEAAR
VAEQLRAYLEGECVEWLRRYLENGKETLQRA

>HLA:HLA04449 B*27:61 181 aa

SEQ ID NO. 131.
SHSMRYFHTSVSRPGRGEPRFITVGYVDDTLFVRFDSDAASPREEPRAPWIEQEGPEYWDRETQICKAKAQTDRE
SLRTLLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

```
>HLA:HLA04564 B*27:62 181 aa
                                                             SEQ ID NO. 132.
SHSMRYFHTSVSRPGRGEPRFITVGYVDDTLFVRFDSDAASPREEPRAPWIEQEGPEYWDRETQICKAKAQTDRE

NLRIALRYYNQSEAGSHTLQNMYGCDVGPDGRLLRGYHQDAYDGKDYIALNEDLSSWTAADTAAQITQRKWEAAR

VAEQLRAYLEGTCVEWLRRHLENGKETLQRA

>HLA:HLA04715 B*27:63 181 aa
                                                             SEQ ID NO. 133.
SHSMRYFHTSVSRPGRGEPRFITVGYVDDTLFVRFDSDAASPREEPRAPWIEQEGPEYWDRETQICKAKAQTDRE

SLRTLLRYYNQSEAGSHTLQNMYGCDVGPDGRLLRGYHQDAYDGKDYIALNEDLSSWTAADTAAQITQRKWEAAR

EAEQLRAYLEGLCVEWLRRYLENGKETLQRA

>HLA:HLA04769 B*27:64N 127 aa
                                                             SEQ ID NO. 134.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNX

>HLA:HLA04771 B*27:65N 53 aa
                                                             SEQ ID NO. 135.
SHSMRYFHTSVSRPGRGEPRFITVGYVDDTLFVRFDSDAASPREEPRAPWIEX

>HLA:HLA05267 B*27:66N 213 aa
                                                             SEQ ID NO. 136.
MRVTAPRTLLLLLWGAVALTETWAGSHSMRYFHTSVSRPGRGEPRFITVGYVDDTLFVRFDSDAASPREEPRAPW

IEQEGPEYWDRETQICKAKAQTDRESLRTLLRYYNQSEAGSHTLQNMYGCDVGPDGRLLRGYHQDAYDGKDYIAL

NEDLSSWTAADTAAQITQRKWEAAREAEQLRATWRASAWSGSADTWRTGRRRCSARTPQRHTX

>HLA:HLA05404 B*27:67 273 aa
                                                             SEQ ID NO. 137.
SHSMRYFHTSVSRPGRGEPRFITVGYVDDTLFVRFDSDAASPRMAPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRADPPKTHVTHHPISDHEATLRCWALGFYPAEITLTWQRDGEDQTQ

DTELVETRPAGDRTFQKWAAVVVPSGEEQRYTCHVQHEGLPKPLTLRW

>HLA:HLA05268 B*27:68 298 aa
                                                             SEQ ID NO. 138.
MRVTAPRTLLLLLWGAVALTETWAGSHSMRYFHTSVSRPGRGEPRFITVGYVDDTLFVRFDSDAASPREEPRAPW

IEQEGPEYWDRETQICKAKAQTDRESLRTLLRYYNQSEAGSHTLQNMYGCDVGPDGRLLRGYHQDAYDGKDYIAL

NEDLSSWTAADTAAQITQRKWEAAREAEQLRAYLEGECVEWLRRYLENGKETLQRADPPKTHVTHHPISDLEATL

RCWALGFYPGEITLTWQRDGEDQTQDTELVETRPAGDRTFQKWAAVVVPSGEEQRYTCHVQHEGLPKPLTLRW

>HLA:HLA05269 B*27:69 337 aa
                                                             SEQ ID NO. 139.
MRVTAPRTLLLLLWGAVALTETWAGSHSMRYFHTSVSRPGRGEPRFITVGYVDDTLFVRFDSDAASPREEPRAPW

IEQEGPEYWDRETQICKAKAQTDRESLRTLLRYYNQSEAGSHTLQNMYGCDVGPDGRLLRGYHQDAYDGKDYIAL

NEDLSSWTAADTAAQITQRKWEAAREAEQLRAYLEGECVEWLRRYLENGKETLQRADPPKTHVTHHPISDHEATL

RCWALGFYPGEITLTWQRDGEDQTQDTELVETRPAGDRTFQKWAAVVVPSGEEQRYTCHVQHEGLLKPLTLRWEP

SSQSTVPIVGIVAGLAVLAVVVIGAVVAAVMCRRKSS

>HLA:HLA05473 B*27:70 181 aa
                                                             SEQ ID NO. 140.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQRMYGCDVGPDGRLLRGYHQDAYDGKDYIALNEDLSSWTAADTAAQITQRKWEAAR

VAEQLRAYLEGECVEWLRRYLENGKETLQRA
```

-continued

```
>HLA:HLA05492 B*27:71 181 aa
                                                             SEQ ID NO. 141.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGTCVEWLRRYLENGKETLQRA

>HLA:HLA05504 B*27:72 181 aa
                                                             SEQ ID NO. 142.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMNGCDVGPDGRLLRGYHQDAYDGKDYIALNEDLSSWTAADTAAQITQRKWEAAR

VAEQLRAYLEGECVEWLRRYLENGKETLQRA

>HLA:HLA05517 B*27:73 181 aa
                                                             SEQ ID NO. 143.
SHSMRYFHTSVSRPGRGEPRFITVGYVDDTLFVRFDSDAASPREEPRAPWIEQEGPEYWDRETQICKAKAQTDRE

DLRTLLRYYNQSEAGSQTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA06183 B*27:74 181 aa
                                                             SEQ ID NO. 144.
SHSMRYFHTFVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA06212 B*27:75 181 aa
                                                             SEQ ID NO. 145.
SHSMRYFHTSVSRPGRGEPRFISVGYVDDTQFVRFDSDAASPREEPRAPWIEQEGPEYWDRETQICKAKAQTDRE

NLRIALRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA06230 B*27:76 181 aa
                                                             SEQ ID No. 146.
SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYNQYAYDGKDYIALNEDLSSWTAADTAAQITQRKWEAAR

VAEQLRAYLEGLCVEWLRRYLENGKETLQRA

>HLA:HLA06255 B*27:77 181 aa
                                                             SEQ ID NO. 147.
SHSMRYFHTSVSRPGRGEPRFITVGYVDDTLFVRFDSDAASPREEPRAPWIEQEGPEYWDRETQICKANTQTDRE

NLRIALRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

>HLA:HLA06256 B*27:78 181 aa
                                                             SEQ ID NO. 148.
SHSMRYFHTSVSRPGRGEPRFITVGYVDDTLFVRFDSDAASPREEPRAPWIEQEGPEYWDRETQICKAKAQTDRE

DLRELLRYYNQSEAGSHTLQNMYGCDVGPDGRLLRGYHQSAYDGKDYIALNEDLSSWTAADTAAQITQRKWEAAR

VAEQLRAYLEGECVEWLRRYLENGKETLQRA

>HLA:HLA06292 B*27:79 181 aa
                                                             SEQ ID NO. 149.
SHSMRYFHTSVSRPGRGEPRFITVGYVDDTLFVRFDSDAASPREEPRAPWIEQEGPEYWDRETQICKAKAQTDRE

SLRTLLRYYNQSEAGSHTLQNMYGCDVGPDGRLLRGYHQDAYDGKVYIALNEDLSSWTAADTAAQITQRKWEAAR

EAEQLRAYLEGECVEWLRRYLENGKETLQRA

>HLA:HLA06353 B*27:80 181 aa
                                                             SEQ ID NO. 150.
SHSMRYFHTSVSRPGRGEPRFITVGYVDDTLFVRFDSDAASPREEPRAPWIEQEGPEYWDRETQICKAKAQTDRE

DLRELLRYYNQEEAGSRTLQNMYGCDVGPDGRLLRGYHQDAYDGKDYIALNEDLSSWTAADTAAQITQRKWEAAR

VAEQLRAYLEGECVEWLRRYLENGKETLQRA
```

-continued

>HLA:HLA06940 B*27:81 181 aa
SEQ ID NO. 151.
SHSMRYFHTSVSRPGRGEPRFITVGYVDDTLFVRFDSDAASPREEPRAPWIEQEGPEYWDRETQICKAKAQTDRE
DLRELLRYYNQSEAGSHTWQTMYGCDVGPDGRLLRGYHQDAYDGKDYIALNEDLSSWTAADTAAQITQRKWEAAR
VAEQLRAYLEGECVEWLRRYLENGKETLQRA

>HLA:HLA06993 B*27:82 181 aa
SEQ ID NO. 152.
SHSMRYFHTSVSRPGRGEPRFITVGYVDDTLFVRFDSDAASPREEPRAPWIEQEGPEYWDRETQICKAKAQTDRE
DLRELLRYYNQEEAGSHTLQNMYGCDVGPDGRLLRGYHQDAYDGKDYIALNEDLSSWTAAVTAAQITQRKWEAAR
VAEQLRAYLEGECVEWLRRYLENGKETLQRA

>HLA:HLA07187 B*27:83 181 aa
SEQ ID NO. 153.
SHSMRYFHTSVSRPGRGEPRFITVGYVDDTLFVRFDSDAASPREEPRAPWIEQEGPEYWDRETQICKAKAQTDRE
NLRIALRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKDTLERA

>HLA:HLA07188 B*27:84 181 aa
SEQ ID NO. 154.
SHSMRYFHEEVERPGRGEPRFIEVGYVDDELFVRFDEDAASPREEPRAPWIEQEGPEYWDREEQICKAKAQEDRE
DLRELLRYYNQEEAGSHTLQNMYGCDVGPDGRLLRGYHQDAYDGKDYIAQNEDLSSWTAADTAAQITQRKWEAAR
VAEQLRAYLEGECVEWLRRYLENGKETLQRA

>HLA:HLA07177 B*27:85 181 aa
SEQ ID NO. 155.
SHSMRYFHTSVSRPGRGEPRFITVGYVDDTLFVRFDSDAASPREEPRAPWIEQEGPEYWDRETQICQAKAQTDRE
DLRELLRYYNQEEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA07339 B*27:86 181 aa
SEQ ID NO. 156.
SHSMRYFHTSVSRPGRGEPRFITVGYVDDTLFVRFDSDAASPREEPRAPWIEQEGPEYWDRETQICKAKAQTDRE
SLRTLLRYYNQSEAGSHTLQNMYGCDVGPDGRLLRGYHQDAYDGKDYIALNEDLSSWTAADTAAQITQRKWEAAR
EAEQLRAYLEGECVEWLRRYLENGKGTLQRA

>HLA:HLA07441 B*27:87 181 aa
SEQ ID NO. 157.
SHSMRYFHTSVSRPGRGEPRFITVGYVDDTLFVRFDSDAASPREEPWAPWIEQEGPEYWDRETQICKAKAQTDRE
DLRELLRYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA07631 B*27:88 181 aa
SEQ ID NO. 158.
SHSMRYFHTSVSRPGRGEPRFITVGYVDDTLFVRFDSDAASPREEPRAPWIEQEGPEYWDRETQICKAKAQTDRE
DLRELLRYYNQSEAGSHTLQNIYGCDVGPDGRLLRGYHQDAYDGKDYIALNEDLSSWTAADTAAQITQRKWEAAR
VAEQLRAYLEGECVEWLRRYLENGKETLQRA

>HLA:HLA07689 B*27:89 181 aa
SEQ ID NO. 159.
SHSMRYFHTSVSRPGRGEPRFITVGYVDDTLFVRFDSDAASPREEPRAPWIEQEGPEYWDRETQICKAKAQTDRE
NLRNLRGYYNQSEAGSHTLQNMYGCDVGPDGRLLRGYHQDAYDGKDYIALNEDLSSWTAADTAAQITQRKWEAAR
VAEQLRAYLEGECVEWLRRYLENGKETLQRA

>HLA:HLA07902 B*27:90:01 181 aa
SEQ ID NO. 160.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLRSWTAADTAAQITQRKWEAAR
VAEQLRAYLEGECVEWLRRYLENGKETLQRA

\>HLA:HLA08505 B*27:90:02 181 aa

SEQ ID NO. 161.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLRSWTAADTAAQITQRKWEAAR

VAEQLRAYLEGECVEWLRRYLENGKETLQRA

\>HLA:HLA11819 B*27:90:03 181 aa

SEQ ID NO. 162.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLRSWTAADTAAQITQRKWEAAR

VAEQLRAYLEGECVEWLRRYLENGKETLQRA

\>HLA:HLA07903 B*27:91 181 aa

SEQ ID NO. 163.

SHSMRYFHTSVSRPGRGEPRFITVGYVDYTLFVRFDSDAASPREEPRAPWIEQEGPEYWDRETQICKAKAQTDRE

SLRTLLRYYNQSEAGSHTLQNMYGCDVGPDGRLLRGYDQYAYDGKDYIALNEDLSSWTAADTAAQITQRKWEAAR

EAEQLRAYLEGECVEWLRRYLENGKETLQRA

\>HLA:HLA07932 B*27:92 181 aa

SEQ ID NO. 164.

SHSMRYFHTSVSRPGRGEPRFITVGYVDDTLFVRFDSDAASPREEPRAPWIEQEGPEYWDRNTQICKTNTQTYRE

DLRTLLRYYNQSEAGSHTLQNMYGCDVGPDGRLLRGYHQDAYDGKDYIALNEDLSSWTAADTAAQITQRKWEAAR

EAEQLRAYLEGECVEWLRRYLENGKETLQRA

\>HLA:HLA08327 B*27:93 181 aa

SEQ ID NO. 165.

SHSMRYFHTSVSRPGRGEPRFITVGYADDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

\>HLA:HLA08330 B*27:94N 58 aa

SEQ ID NO. 166.

SHSMRYFHTSVSRPGRGEPRFITVGYVDDTLFVRFDSDAASPREEPRAPWIEQEGPEY

\>HLA:HLA08331 B*27:95 181 aa

SEQ ID NO. 167.

SHSMRYFHTSVSRPGRGEPRFITVGYVDDTLFVRFDSDAASPREEPRAPWIEQEGPEYWDRETQICKAKAQTDRE

NLRIALRYYNQSEAGSHTLQNMYGCDVGPDGRLLRGYHQDAYDGKDYIALNEDLRSWTAADTAAQITQRKWEAAR

VAEQLRAYLEGECVEWLRRYLENGKETLQRA

\>HLA:HLA08332 B*27:96:01 181 aa

SEQ ID NO. 168.

SHSMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVRPDGRLLRGYHQDAYDGKDYIALNEDLSSWTAADTAAQITQRKWEAAR

VAEQLRAYLEGECVEWLRRYLENGKETLQRA

\>HLA:HLA10704 B*27:96:02 337 aa

SEQ ID NO. 169.

MRVTAPRTLLLLLWGAVALTETWAGSHSMRYFHTSVSRPGRGEPRFITVGYVDDTLFVRFDSDAASPREEPRAPW

IEQEGPEYWDRETQICKAKAQTDREDLRTLLRYYNQSEAGSHTLQNMYGCDVRPDGRLLRGYHQDAYDGKDYIAL

NEDLSSWTAADTAAQITQRKWEAARVAEQLRAYLEGECVEWLRRYLENGKETLQRADPPKTHVTHHPISDHEATL

RCWALGFYPAEITLTWQRDGEDQTQDTELVETRPAGDRTFQKWAAVVVPSGEEQRYTCHVQHEGLPKPLTLRWEP

SSQSTVPIVGIVAGLAVLAVVVIGAVVAAVMCRRKSS

\>HLA:HLA08472 B*27:97 181 aa

SEQ ID NO. 170.

SHCMRYFHTSVSRPGRGEPRFITVGYVDDTLFVRFDSDAASPREEPRAPWIEQEGPEYWDRETQICKAKAQTDRE

DLRTLLRYYNQSEAGSHTLQNMYGCDVGPDGRLLRGYHQDAYDGKDYIALNEDLSSWTAADTAAQITQRKWEAAR

VAEQLRAYLEGECVEWLRRYLENGKETLQRA

-continued

>HLA:HLA08504 B*27:98 181 aa
SEQ ID NO. 171.
SHSMRYFHTSVSRPGRGEPRFITVGYVDDTLFVRFDSDAASPREEPRAPWIEQEGPEYWDRETQICKAKAQTDRE
DLRTLLRYYNQSEAGSHTLQNMYGCDVGPDGRLLRGYHQDAYDGKDYIALNEDLSSWTAADTAAQITQLKWEAAR
VAEQLRAYLEGECVEWLRRYLENGKETLQRA

>HLA:HLA08662 B*27:99 181 aa
SEQ ID NO. 172.
SHSMRYFHTSVSRPGRGEPRFITVGYVDDTLFVRFDSDAASPREEPRAPWIEQEGPEYWDRETQICKARAQTDRE
DLRTLLRYYNQSEAGSHTLQNMYGCDVGPDGRLLRGYHQDAYDGKDYIALNEDLSSWAAADTAAQITQRKWEAAR
VAEQLRAYLEGECVEWLRRYLENGKETLQRA

Full and partial sequences SEQ ID No 001 to SEQ ID No 172 are provided in the accompanying sequence listing.

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_303_30_seqlist.txt, created Aug. 4, 2017, about 359 KB, which is incorporated by reference herein.

We claim:

1. A method for treatment of a cancer selected from the group consisting of colon cancer, breast cancer, pancreatic cancer and lymphoma, the method comprising: administering to a patient in need thereof a HLA-B27 fusion protein dimer, wherein the HLA-B27 fusion protein dimer comprises a first and a second monomer, and each monomer comprises independently of the other monomer:
   (i) HLA-B27 alpha 1, 2 and 3 domains of a HLA-B27 heavy chain polypeptide selected from the group consisting of amino acid sequences set forth herein as positions 25 to 309 of: SEQ ID NO: 15, SEQ ID NO: 8, SEQ ID NO: 10, SEQ ID NO: 11, SEQ ID NO: 42, SEQ ID NO: 43, SEQ ID NO: 47, SEQ ID NO: 48, and SEQ ID NO: 49,
   (ii) an Fc (fragment crystallizable) domain, and
   (iii) optionally, an amino acid linker joining the HLA-B27 chain and said Fc domain.

2. The method of claim 1, wherein the first and the second monomer are the same.

3. The method of claim 1, wherein each monomer additionally and independently comprises a peptide epitope fragment.

4. The method of claim 1, wherein the HLA-B27 chain further comprises a transmembrane domain and does not comprise an intracellular domain.

5. The method of claim 1, wherein disulphide bonds link the two monomers.

6. The method of claim 1, wherein the Fc domain comprises heavy chain constant regions $C_H2$ and $C_H3$ selected from any one of immunoglobulin type G (IgG), type A (IgA), type D (IgD), type E (IgE) or type M (IgM).

7. The method of claim 1, wherein the amino acid linker comprises 1 to 50 amino acids, linking the HLA-B27 chain to the Fc domain as one single polypeptide chain.

8. The method according to claim 1, wherein the HLA-B27 alpha 1, 2 and 3 domains is set forth herein as positions 25 to 309 of SEQ ID NO: 15.

9. The method of claim 1, further comprising administering to the patient a checkpoint modulatory agent selected from
   i. a checkpoint inhibitory agent (CPI), wherein said CPI is selected from:
      1. an inhibitor of the interaction of CTLA4 with either B7-1 (CD80) and/or B7-2 (CD86), a polypeptide ligand to CTLA-4 or to CD80 or to CD86;
      2. an inhibitor of the interaction of PD-1 with either PD-L1 and/or PD-L2; and 3. an inhibitory polypeptide ligand, an antibody, of T cell immunoglobulin and mucin domain-containing 3 (TIM-3); and
   ii. a checkpoint agonist agent, selected to bind to and activate the tumor necrosis factor receptor 4-1BB;

wherein said checkpoint modulatory agent is a polypeptide selected from an antibody and the polypeptide is selectively reactive to a checkpoint mediator selected from CTLA4, PD-1, CD80, CD86, PD-L1, PD-L2, TIM-3, 4-1 BB and 4-1BBL.

10. The method according to claim 9, wherein said checkpoint inhibitory agent is selected from an inhibitor of CTLA4 interaction with CD80 or CD86, an inhibitor of the interaction of PD-1 with its ligand PD-L1, and a ligand TIM-3.

11. The method of claim 9, wherein the cancer is pancreatic cancer or breast cancer, and wherein the checkpoint modulatory agent is an antibody that is selectively reactive to CTLA.

12. The method of claim 9, wherein the cancer is lymphoma, and wherein the checkpoint modulatory agent is an antibody that is selectively inhibits the interaction of PD-1 with either PD-L1 and/or PD-L2.

\* \* \* \* \*

```
                          SEQUENCE LISTING

<160> NUMBER OF SEQ ID NOS: 176

<210> SEQ ID NO 1
   <211> LENGTH: 24
   <212> TYPE: PRT
   <213> ORGANISM: Homo sapiens

<400> SEQUENCE: 1

Met Arg Val Thr Ala Pro Arg Thr Leu Leu Leu Leu Trp Gly Ala
   1               5                   10                  15

Val Ala Leu Thr Glu Thr Trp Ala
               20

<210> SEQ ID NO 2
   <211> LENGTH: 90
   <212> TYPE: PRT
   <213> ORGANISM: Homo sapiens

<400> SEQUENCE: 2

Gly Ser His Ser Met Arg Tyr Phe His Thr Ser Val Ser Arg Pro Gly
   1               5                   10                  15

Arg Gly Glu Pro Arg Phe Ile Thr Val Gly Tyr Val Asp Asp Thr Leu
                   20                  25                  30

Phe Val Arg Phe Asp Ser Asp Ala Ala Ser Pro Arg Glu Glu Pro Arg
               35                  40                  45

Ala Pro Trp Ile Glu Gln Glu Gly Pro Glu Tyr Trp Asp Arg Glu Thr
           50                  55                  60

Gln Ile Cys Lys Ala Lys Ala Gln Thr Asp Arg Glu Asn Leu Arg Ile
   65                  70                  75                  80

Ala Leu Arg Tyr Tyr Asn Gln Ser Glu Ala
                   85                  90

<210> SEQ ID NO 3
   <211> LENGTH: 92
   <212> TYPE: PRT
   <213> ORGANISM: Homo sapiens

<400> SEQUENCE: 3

Gly Ser His Thr Leu Gln Asn Met Tyr Gly Cys Asp Val Gly Pro Asp
```

```
                1               5                  10                 15
              Gly Arg Leu Leu Arg Gly Tyr His Gln Asp Ala Tyr Asp Gly Lys Asp
                              20                 25                 30

Tyr Ile Ala Leu Asn Glu Asp Leu Ser Ser Trp Thr Ala Ala Asp Thr
                              35                 40                 45

Ala Ala Gln Ile Thr Gln Arg Lys Trp Glu Ala Ala Arg Val Ala Glu
                              50                 55                 60

Gln Leu Arg Ala Tyr Leu Glu Gly Glu Cys Val Glu Trp Leu Arg Arg
              65                              70                 75                 80

Tyr Leu Glu Asn Gly Lys Glu Thr Leu Gln Arg Ala
                              85                 90

<210> SEQ ID NO 4
<211> LENGTH: 103
<212> TYPE: PRT
<213> ORGANISM: Homo sapiens

<400> SEQUENCE: 4

Asp Pro Pro Lys Thr His Val Thr His His Pro Ile Ser Asp His Glu
1               5                  10                 15

Ala Thr Leu Arg Cys Trp Ala Leu Gly Phe Tyr Pro Ala Glu Ile Thr
                20                 25                 30

Leu Thr Trp Gln Arg Asp Gly Glu Asp Gln Thr Gln Asp Thr Glu Leu
            35                 40                 45

Val Glu Thr Arg Pro Ala Gly Asp Arg Thr Phe Gln Lys Trp Ala Ala
        50                 55                 60

Val Val Val Pro Ser Gly Glu Glu Gln Arg Tyr Thr Cys His Val Gln
65                  70                 75                 80

His Glu Gly Leu Pro Lys Pro Leu Thr Leu Arg Trp Glu Pro Ser Ser
                85                 90                 95

Gln Ser Thr Val Pro Ile Val
                100

<210> SEQ ID NO 5
<211> LENGTH: 53
<212> TYPE: PRT
<213> ORGANISM: Homo sapiens

<400> SEQUENCE: 5

Gly Ile Val Ala Gly Leu Ala Val Leu Ala Val Val Val Ile Gly Ala
1               5                  10                 15

Val Val Ala Ala Val Met Cys Arg Arg Lys Ser Ser Gly Gly Lys Gly
                20                 25                 30

Gly Ser Tyr Ser Gln Ala Ala Cys Ser Asp Ser Ala Gln Gly Ser Asp
            35                 40                 45

Val Ser Leu Thr Ala
            50

<210> SEQ ID NO 6
<211> LENGTH: 280
<212> TYPE: PRT
<213> ORGANISM: Homo sapiens
<220> FEATURE:
<221> NAME/KEY: DOMAIN
<222> LOCATION: (1)..(90)
<223> OTHER INFORMATION: alpha 1
<220> FEATURE:
<221> NAME/KEY: DOMAIN
<222> LOCATION: (91)..(182)
<223> OTHER INFORMATION: alpha 2
```

```
<220> FEATURE:
<221> NAME/KEY: DOMAIN
<222> LOCATION: (183)..(280)
<223> OTHER INFORMATION: alpha 3

<400> SEQUENCE: 6

Gly Ser His Ser Met Arg Tyr Phe His Thr Ser Val Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Glu Thr
    50                  55                  60

Gln Ile Cys Lys Ala Lys Ala Gln Thr Asp Arg Glu Asp Leu Arg Thr
65                  70                  75                  80

Leu Leu Arg Tyr Tyr Asn Gln Ser Glu Ala Gly Ser His Thr Leu Gln
                85                  90                  95

Asn Met Tyr Gly Cys Asp Val Gly Pro Asp Gly Arg Leu Leu Arg Gly
            100                 105                 110

Tyr His Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
130                 135                 140

Arg Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser
        275                 280

<210> SEQ ID NO 7
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 7

Ser His Ser Met Arg Tyr Phe His Thr Ser Val Ser Arg Pro Gly Arg
1               5                   10                  15
```

```
Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Tyr Arg Glu Asn Leu Arg Thr Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 8
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 8

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95
```

-continued

Thr Asp Arg Glu Asn Leu Arg Ile Ala Leu Arg Tyr Tyr Asn Gln Ser
            100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 9
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 9

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

```
Ile Cys Lys Ala Lys Ala Gln Thr Asp Arg Glu Asn Leu Arg Ile Ala
 65                  70                  75                  80

Leu Arg Tyr Tyr Asn Gln Ser Glu Ala Gly Ser His Thr Leu Gln Asn
             85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 10
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: Signal peptide
<220> FEATURE:
<221> NAME/KEY: DOMAIN
<222> LOCATION: (25)..(119)
<223> OTHER INFORMATION: alpha 1
<220> FEATURE:
<221> NAME/KEY: DOMAIN
<222> LOCATION: (120)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 10

Met Arg Val Thr Ala Pro Arg Thr Leu Leu Leu Leu Leu Trp Gly Ala
  1               5                  10                  15

Val Ala Leu Thr Glu Thr Trp Ala Gly Ser His Ser Met Arg Tyr Phe
             20                  25                  30

His Thr Ser Val Ser Arg Pro Gly Arg Gly Glu Pro Arg Phe Ile Thr
             35                  40                  45

Val Gly Tyr Val Asp Asp Thr Leu Phe Val Arg Phe Asp Ser Asp Ala
         50                  55                  60

Ala Ser Pro Arg Glu Glu Pro Arg Ala Pro Trp Ile Glu Gln Glu Gly
 65                  70                  75                  80

Pro Glu His Trp Asp Arg Glu Thr Gln Ile Cys Lys Ala Lys Ala Gln
             85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
        130                 135                 140
```

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

```
<210> SEQ ID NO 11
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(119)
<223> OTHER INFORMATION: alpha 1
<220> FEATURE:
<221> NAME/KEY: DOMAIN
<222> LOCATION: (120)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 11
```

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
         50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 12
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 12

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 13
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 13

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

```
Gly Glu Cys Val Glu Trp Leu Arg Arg Tyr Leu Glu Asn Gly Lys Glu
                165                 170                 175

Thr Leu Gln Arg Ala
            180

<210> SEQ ID NO 14
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 14

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240
```

```
Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Lys Pro Leu Thr Leu Arg Trp Glu Pro Ser Ser Gln Ser
                290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 15
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 15

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
                35                  40                  45

Val Gly Tyr Val Asp Asp Thr Leu Phe Val Arg Phe Asp Ser Asp Ala
            50                  55                  60

Ala Ser Pro Arg Glu Glu Pro Arg Ala Pro Trp Ile Glu Gln Glu Gly
65              70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
                100                 105                 110

Glu Ala Gly Ser His Thr Leu Gln Asn Met Tyr Gly Cys Asp Val Gly
                115                 120                 125

Pro Asp Gly Arg Leu Leu Arg Gly Tyr His Gln Asp Ala Tyr Asp Gly
                130                 135                 140

Lys Asp Tyr Ile Ala Leu Asn Glu Asp Leu Ser Ser Trp Thr Ala Ala
145                 150                 155                 160
```

```
Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 16
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 16

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125
```

```
Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180
```

<210> SEQ ID NO 17
<211> LENGTH: 206
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2

<400> SEQUENCE: 17

```
Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala
        195                 200                 205
```

<210> SEQ ID NO 18
<211> LENGTH: 298
<212> TYPE: PRT
<213> ORGANISM: Homo sapiens
<220> FEATURE:
<221> NAME/KEY: DOMAIN
<222> LOCATION: (1)..(24)

```
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(298)
<223> OTHER INFORMATION: alpha 3

<400> SEQUENCE: 18

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Gly Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp
    290                 295

<210> SEQ ID NO 19
<211> LENGTH: 181
<212> TYPE: PRT
<213> ORGANISM: Homo sapiens
<220> FEATURE:
```

```
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 19

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 20
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 20

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
                20                  25                  30
```

```
His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
 50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
 130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 21
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 21

Ser His Ser Met Arg Tyr Phe His Thr Ser Val Ser Arg Pro Gly Arg
1               5                   10                  15
```

```
Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 22
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 22

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160
```

```
Gly Glu Cys Val Glu Trp Leu Arg Arg Tyr Leu Glu Asn Gly Lys Glu
                165                 170                 175

Thr Leu Gln Arg Ala
            180

<210> SEQ ID NO 23
<211> LENGTH: 296
<212> TYPE: PRT
<213> ORGANISM: Homo sapiens
<220> FEATURE:
<221> NAME/KEY: DOMAIN
<222> LOCATION: (1)..(10)
<223> OTHER INFORMATION: signal peptide
<220> FEATURE:
<221> NAME/KEY: DOMAIN
<222> LOCATION: (11)..(100)
<223> OTHER INFORMATION: alpha 1
<220> FEATURE:
<221> NAME/KEY: DOMAIN
<222> LOCATION: (101)..(192)
<223> OTHER INFORMATION: alpha 2
<220> FEATURE:
<221> NAME/KEY: DOMAIN
<222> LOCATION: (193)..(295)
<223> OTHER INFORMATION: alpha 3
<220> FEATURE:
<221> NAME/KEY: DOMAIN
<222> LOCATION: (296)..(296)
<223> OTHER INFORMATION: transmembrabe

<400> SEQUENCE: 23

Gly Ala Val Ala Leu Thr Glu Thr Trp Ala Gly Ser His Ser Met Arg
1               5                   10                  15

Tyr Phe His Thr Ser Val Ser Arg Pro Gly Arg Gly Glu Pro Arg Phe
                20                  25                  30

Ile Thr Val Gly Tyr Val Asp Asp Thr Leu Phe Val Arg Phe Asp Ser
            35                  40                  45

Asp Ala Ala Ser Pro Arg Glu Glu Pro Arg Ala Pro Trp Ile Glu Gln
        50                  55                  60

Glu Gly Pro Glu Tyr Trp Asp Arg Glu Thr Gln Ile Cys Lys Ala Lys
65                  70                  75                  80

Ala Gln Thr Asp Arg Glu Asp Leu Arg Thr Leu Leu Arg Tyr Tyr Asn
                85                  90                  95

Gln Ser Glu Ala Gly Ser His Thr Leu Gln Asn Met Tyr Gly Cys Asp
            100                 105                 110

Val Gly Pro Asp Gly Arg Leu Leu Arg Gly Tyr His Gln Asp Ala Tyr
        115                 120                 125

Asp Gly Lys Asp Tyr Ile Ala Leu Asn Glu Asp Leu Ser Ser Trp Thr
    130                 135                 140

Ala Ala Asp Thr Ala Ala Gln Ile Thr Gln Arg Lys Trp Glu Ala Ala
145                 150                 155                 160

Arg Val Ala Glu Gln Leu Arg Ala Tyr Leu Glu Gly Glu Cys Val Glu
                165                 170                 175

Trp Leu Arg Arg Tyr Leu Glu Asn Gly Lys Glu Thr Leu Gln Arg Ala
            180                 185                 190

Asp Pro Pro Lys Thr His Val Thr His His Pro Ile Ser Asp His Glu
        195                 200                 205

Ala Thr Leu Arg Cys Trp Ala Leu Gly Phe Tyr Pro Ala Glu Ile Thr
    210                 215                 220

Leu Thr Trp Gln Arg Asp Gly Glu Asp Gln Thr Gln Asp Thr Glu Leu
225                 230                 235                 240
```

Val Glu Thr Arg Pro Ala Gly Asp Arg Thr Phe Gln Lys Trp Ala Ala
            245                 250                 255

Val Val Val Pro Ser Gly Glu Glu Gln Arg Tyr Thr Cys His Val Gln
        260                 265                 270

His Glu Gly Leu Pro Lys Pro Leu Thr Leu Arg Trp Glu Pro Ser Ser
    275                 280                 285

Gln Ser Thr Val Pro Ile Val Gly
    290                 295

<210> SEQ ID NO 24
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 24

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 25
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 25

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 26
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 26

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140
```

```
Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 27
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 27

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 28
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 28

Ser His Ser Met Arg Tyr Phe His Thr Ser Val Ser Arg Pro Gly Arg
```

```
                1               5                   10                  15
                Gly Glu Pro Arg Phe Ile Thr Val Gly Tyr Val Asp Asp Thr Leu Phe
                            20                  25                  30

Val Arg Phe Asp Ser Asp Ala Ala Ser Pro Arg Glu Glu Pro Arg Ala
                            35                  40                  45

Pro Trp Ile Glu Gln Glu Gly Pro Glu Tyr Trp Asp Arg Glu Thr Gln
                            50                  55                  60

Ile Cys Lys Ala Lys Ala Gln Thr Asp Arg Glu Asp Leu Arg Thr Leu
                65                      70                  75                  80

Leu Arg Tyr Tyr Asn Gln Ser Glu Ala Gly Ser His Thr Leu Gln Asn
                                85                  90                  95

Met Tyr Gly Cys Asp Val Gly Pro Asp Gly Arg Leu Leu Arg Gly Tyr
                            100                 105                 110

His Gln Asp Ala Tyr Asp Gly Lys Asp Tyr Ile Ala Leu Asn Glu Asp
                            115                 120                 125

Leu Ser Ser Trp Thr Ala Ala Asp Thr Ala Ala Gln Ile Thr Gln Arg
                            130                 135                 140

Lys Trp Glu Ala Ala Arg Val Ala Glu Gln Leu Arg Ala Tyr Leu Glu
                145                     150                 155                 160

Gly Glu Cys Val Glu Trp Leu Arg Arg Tyr Leu Glu Asn Gly Lys Glu
                                165                 170                 175

Thr Leu Gln Arg Ala
                            180
```

<210> SEQ ID NO 29
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 29

```
                Ser His Ser Met Arg Tyr Phe His Thr Ser Val Ser Arg Pro Gly Arg
                1               5                   10                  15

Gly Glu Pro Arg Phe Ile Thr Val Gly Tyr Val Asp Asp Thr Leu Phe
                            20                  25                  30

Val Arg Phe Asp Ser Asp Ala Ala Ser Pro Arg Glu Glu Pro Arg Ala
                            35                  40                  45

Pro Trp Ile Glu Gln Glu Gly Pro Glu Tyr Trp Asp Arg Glu Thr Gln
                            50                  55                  60

Ile Cys Lys Ala Lys Ala Gln Thr Asp Arg Glu Asp Leu Arg Thr Leu
                65                      70                  75                  80

Leu Arg Tyr Tyr Asn Gln Ser Glu Ala Gly Ser His Thr Leu Gln Asn
                                85                  90                  95

Met Tyr Gly Cys Asp Val Gly Pro Asp Gly Arg Leu Leu Arg Gly Tyr
                            100                 105                 110

His Gln Asp Ala Tyr Asp Gly Lys Asp Tyr Ile Ala Leu Asn Glu Asp
                            115                 120                 125

Leu Ser Ser Trp Thr Ala Ala Asp Thr Ala Ala Gln Ile Thr Gln Arg
                            130                 135                 140

Lys Trp Glu Ala Ala Arg Val Ala Glu Gln Leu Arg Ala Tyr Leu Glu
```

```
                145                 150                 155                 160
Gly Glu Cys Val Glu Trp Leu Arg Arg Tyr Leu Glu Asn Gly Lys Glu
                    165                 170                 175

Thr Leu Gln Arg Ala
            180

<210> SEQ ID NO 30
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 30

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                    165                 170                 175

Thr Leu Gln Arg Ala
            180

<210> SEQ ID NO 31
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
```

```
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 31

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360
```

```
<210> SEQ ID NO 32
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 32
```

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

```
<210> SEQ ID NO 33
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 33
```

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

```
Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 34
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 34

Ser His Ser Met Arg Tyr Phe His Thr Ser Val Ser Arg Pro Gly Arg
  1               5                  10                  15

Gly Glu Pro Arg Phe Ile Thr Val Gly Tyr Val Asp Asp Thr Leu Phe
             20                  25                  30

Val Arg Phe Asp Ser Asp Ala Ala Ser Pro Arg Glu Glu Pro Arg Ala
         35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 35
<211> LENGTH: 181
```

```
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 35

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 36
<211> LENGTH: 325
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(325)
<223> OTHER INFORMATION: transmembrane and cytoplasmic tail

<400> SEQUENCE: 36

Met Arg Val Thr Ala Pro Arg Thr Leu Leu Leu Leu Leu Trp Gly Ala
1               5                   10                  15
```

-continued

```
Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
 50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala
            325

<210> SEQ ID NO 37
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 37

Ser His Ser Met Arg Tyr Phe His Thr Ser Val Ser Arg Pro Gly Arg
1               5                   10                  15
```

```
Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180
```

<210> SEQ ID NO 38
<211> LENGTH: 298
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(298)
<223> OTHER INFORMATION: alpha 3

<400> SEQUENCE: 38

```
Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Leu Leu Arg Tyr Tyr Asn Gln Ser
            100                 105                 110
```

-continued

```
Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
        130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp
    290                 295
```

<210> SEQ ID NO 39
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 39

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125
```

-continued

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 40
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 40

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

-continued

```
Thr Leu Gln Arg Ala
            180

<210> SEQ ID NO 41
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 41

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65              70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 42
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
```

<223> OTHER INFORMATION: transmembrane and cytoplasmic tail

<400> SEQUENCE: 42

```
Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
            85                  90                  95

Thr Asp Arg Glu Ser Leu Arg Thr Leu Leu Arg Tyr Tyr Asn Gln Ser
        100                 105                 110

Glu Ala Gly Ser His Thr Leu Gln Asn Met Tyr Gly Cys Asp Val Gly
    115                 120                 125

Pro Asp Gly Arg Leu Leu Arg Gly Tyr Asp Gln Tyr Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
            165                 170                 175

Ala Glu Gln Leu Arg Ala Tyr Leu Glu Gly Cys Val Glu Trp Leu
        180                 185                 190

Arg Arg Tyr Leu Glu Asn Gly Lys Glu Thr Leu Gln Arg Ala Asp Pro
    195                 200                 205

Pro Lys Thr His Val Thr His His Pro Ile Ser Asp His Glu Ala Thr
210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
            325                 330                 335

Ser Gly Gly Lys Gly Gly Ser Tyr Ser Gln Ala Ala Cys Ser Asp Ser
        340                 345                 350

Ala Gln Gly Ser Asp Val Ser Leu Thr Ala
    355                 360
```

<210> SEQ ID NO 43
<211> LENGTH: 362
<212> TYPE: PRT
<213> ORGANISM: Homo sapiens
<220> FEATURE:

```
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 43

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
            85                  90                  95

Thr Asp Arg Glu Asp Leu Arg Thr Leu Leu Arg Tyr Tyr Asn Gln Ser
        100                 105                 110

Glu Ala Gly Ser His Thr Leu Gln Ser Met Tyr Gly Cys Asp Val Gly
            115                 120                 125

Pro Asp Gly Arg Leu Leu Arg Gly His Asn Gln Tyr Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Val
            165                 170                 175

Ala Glu Gln Leu Arg Ala Tyr Leu Glu Gly Glu Cys Val Glu Trp Leu
        180                 185                 190

Arg Arg Tyr Leu Glu Asn Gly Lys Glu Thr Leu Gln Arg Ala Asp Pro
    195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp Glu Pro Ser Ser Gln Ser
290                 295                 300
```

```
Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
            325                 330                 335

Ser Gly Gly Lys Gly Gly Ser Tyr Ser Gln Ala Ala Cys Ser Asp Ser
        340                 345                 350

Ala Gln Gly Ser Asp Val Ser Leu Thr Ala
        355                 360

<210> SEQ ID NO 44
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 44

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Ser
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255
```

```
Thr Cys His Val Gln His Glu Gly Leu Pro Lys Pro Leu Thr Leu Arg
            260                 265                 270

Trp

<210> SEQ ID NO 45
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 45

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Ser
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 46
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 46

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30
```

-continued

```
Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Ser
                85                  90                  95

Met Tyr Gly Cys Asp Val Gly Pro Asp Gly Arg Leu Leu Arg Gly His
               100                 105                 110

Asn Gln Tyr Ala Tyr Asp Gly Lys Asp Tyr Ile Ala Leu Asn Glu Asp
               115                 120                 125

Leu Arg Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
                180

<210> SEQ ID NO 47
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 47

Met Arg Val Thr Ala Pro Arg Thr Leu Leu Leu Leu Leu Trp Gly Ala
 1               5                  10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
                35                  40                  45

Val Gly Tyr Val Asp Asp Thr Leu Phe Val Arg Phe Asp Ser Asp Ala
 50                  55                  60

Ala Ser Pro Arg Glu Glu Pro Ala Pro Trp Ile Glu Gln Glu Gly
 65                  70                  75                  80

Pro Glu Tyr Trp Asp Arg Glu Thr Gln Ile Cys Lys Ala Lys Ala Gln
                85                  90                  95

Thr Asp Arg Glu Ser Leu Arg Asn Leu Arg Gly Tyr Tyr Asn Gln Ser
               100                 105                 110
```

```
Glu Ala Gly Ser His Thr Leu Gln Asn Met Tyr Gly Cys Asp Val Gly
            115                 120                 125

Pro Asp Gly Arg Leu Leu Arg Gly Tyr His Gln Ala Tyr Asp Gly
        130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Cys Val Glu Trp Leu
            180                 185                 190

Arg Arg Tyr Leu Glu Asn Gly Lys Glu Thr Leu Gln Arg Ala Asp Pro
                195                 200                 205

Pro Lys Thr His Val Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 48
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 48

Met Arg Val Thr Ala Pro Arg Thr Leu Leu Leu Leu Leu Trp Gly Ala
1               5                   10                  15
```

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
 50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln His Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 49
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)

```
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 49

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Val Met Cys Arg Arg Lys Ser
                325                 330                 335
```

```
Ser Gly Gly Lys Gly Gly Ser Tyr Ser Gln Ala Ala Cys Ser Asp Ser
                340             345                 350

Ala Gln Gly Ser Asp Val Ser Leu Thr Ala
        355                 360

<210> SEQ ID NO 50
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 50

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Met Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Gly Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp
```

```
<210> SEQ ID NO 51
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 51

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Gln Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 52
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 52

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60
```

Ile Cys Lys Ala Lys Ala Gln Thr Asp Arg Glu Asn Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

Asn Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 53
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 53

Ser His Ser Met Arg Tyr Phe His Thr Ser Val Ser Arg Pro Gly Cys
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro

```
                  180                 185                 190
Ile Ser Asp His Glu Ala Thr Leu Arg Cys Trp Ala Leu Gly Phe Tyr
        195                 200                 205

Pro Gly Glu Ile Thr Leu Thr Trp Gln Arg Asp Gly Glu Asp Gln Thr
        210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
                260                 265                 270

Trp

<210> SEQ ID NO 54
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 54

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Ala Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 55
<211> LENGTH: 273
<212> TYPE: PRT
<213> ORGANISM: Homo sapiens
<220> FEATURE:
<221> NAME/KEY: DOMAIN
<222> LOCATION: (1)..(89)
```

```
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 55

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu His Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Gly Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 56
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
```

-continued

```
<400> SEQUENCE: 56

Ser His Ser Met Arg Tyr Phe His Thr Ala Met Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

Asp Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 57
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 57

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Leu Gly Pro Asp Gly Arg Leu Leu Arg Gly Tyr
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
```

```
                    130                 135                 140
Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                    165                 170                 175

Thr Leu Gln Arg Ala
            180

<210> SEQ ID NO 58
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 58

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Glu Ala Glu Gln Arg Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 59
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
```

```
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 59

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Arg Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Gly Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Ala Ala Val Met Cys Arg Arg Lys Ser
                325                 330                 335

Ser

<210> SEQ ID NO 60
```

-continued

```
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 60

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65              70                  75                  80

Pro Glu Tyr Trp Asp Arg Glu Thr Gln Ile Cys Lys Ala Lys Ala Gln
            85                  90                  95

Thr Asp Arg Glu Ser Leu Arg Thr Leu Leu Arg Tyr Tyr Asn Gln Ser
        100                 105                 110

Glu Ala Gly Ser His Thr Leu Gln Ser Met Tyr Gly Cys Asp Val Gly
    115                 120                 125

Pro Asp Gly Arg Leu Leu Arg Gly His Asn Gln Tyr Ala Tyr Asp Gly
130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Val
            165                 170                 175

Ala Glu Gln Leu Arg Ala Tyr Leu Glu Gly Glu Cys Val Glu Trp Leu
        180                 185                 190

Arg Arg Tyr Leu Glu Asn Gly Lys Glu Thr Leu Gln Arg Ala Asp Pro
    195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
        260                 265                 270

Val Pro Ser Gly Glu Glu Gln Arg Tyr Thr Cys His Val Gln His Glu
    275                 280                 285
```

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 61
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 61

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asn Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

-continued

```
Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 62
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 62

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Cys Gly Glu Pro Arg Phe Ile Thr
            35                  40                  45

Val Gly Tyr Val Asp Asp Thr Leu Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu His Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110
```

```
Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
        130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 63
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 63

Met Arg Val Thr Ala Pro Arg Thr Leu Leu Leu Leu Leu Trp Gly Ala
1               5                   10                  15

Val Ala Leu Thr Glu Thr Trp Ala Val Ser His Ser Met Arg Tyr Phe
                20                  25                  30

His Thr Ser Val Ser Arg Pro Gly Arg Gly Glu Pro Arg Phe Ile Thr
```

```
                 35                  40                  45
Val Gly Tyr Val Asp Asp Thr Leu Phe Val Arg Phe Asp Ser Asp Ala
 50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 64
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
```

```
<220> FEATURE:
<221> NAME/KEY: DOMAIN
<222> LOCATION: (310)..(337)
<223> OTHER INFORMATION: transmembrane and cytoplasmic tail

<400> SEQUENCE: 64
```

| | | | | | | | | | | | | | | |
|---|---|---|---|---|---|---|---|---|---|---|---|---|---|---|
| Met | Arg | Val | Thr | Ala | Pro | Arg | Thr | Leu | Leu | Leu | Leu | Trp | Gly | Ala |
| 1 | | | | 5 | | | | | 10 | | | | | 15 |
| Val | Ala | Leu | Thr | Glu | Thr | Trp | Ala | Gly | Ser | His | Ser | Met | Gly | Tyr | Phe |
| | | | 20 | | | | | 25 | | | | | 30 | |
| His | Thr | Ser | Val | Ser | Arg | Pro | Gly | Arg | Gly | Glu | Pro | Arg | Phe | Ile | Thr |
| | | 35 | | | | | 40 | | | | | 45 | | |
| Val | Gly | Tyr | Val | Asp | Asp | Thr | Leu | Phe | Val | Arg | Phe | Asp | Ser | Asp | Ala |
| | 50 | | | | | 55 | | | | | 60 | | | | |
| Ala | Ser | Pro | Arg | Glu | Glu | Pro | Arg | Ala | Pro | Trp | Ile | Glu | Gln | Glu | Gly |
| 65 | | | | | 70 | | | | | 75 | | | | | 80 |
| Pro | Glu | Tyr | Trp | Asp | Arg | Glu | Thr | Gln | Ile | Cys | Lys | Ala | Lys | Ala | Gln |
| | | | | 85 | | | | | 90 | | | | | 95 | |
| Thr | Asp | Arg | Glu | Ser | Leu | Arg | Thr | Leu | Leu | Arg | Tyr | Tyr | Asn | Gln | Ser |
| | | | 100 | | | | | 105 | | | | | 110 | | |
| Glu | Ala | Gly | Ser | His | Thr | Leu | Gln | Asn | Met | Tyr | Gly | Cys | Asp | Val | Gly |
| | | | 115 | | | | | 120 | | | | | 125 | | |
| Pro | Asp | Gly | Arg | Leu | Leu | Arg | Gly | Tyr | His | Gln | Asp | Ala | Tyr | Asp | Gly |
| | 130 | | | | | 135 | | | | | 140 | | | | |
| Lys | Asp | Tyr | Ile | Ala | Leu | Asn | Glu | Asp | Leu | Ser | Ser | Trp | Thr | Ala | Ala |
| 145 | | | | | 150 | | | | | 155 | | | | | 160 |
| Asp | Thr | Ala | Ala | Gln | Ile | Thr | Gln | Arg | Lys | Trp | Glu | Ala | Ala | Arg | Glu |
| | | | | 165 | | | | | 170 | | | | | 175 | |
| Ala | Glu | Gln | Leu | Arg | Ala | Tyr | Leu | Glu | Gly | Glu | Cys | Val | Glu | Trp | Leu |
| | | | 180 | | | | | 185 | | | | | 190 | | |
| Arg | Arg | Tyr | Leu | Glu | Asn | Gly | Lys | Glu | Thr | Leu | Gln | Arg | Ala | Asp | Pro |
| | | | 195 | | | | | 200 | | | | | 205 | | |
| Pro | Lys | Thr | His | Val | Thr | His | His | Pro | Ile | Ser | Asp | His | Glu | Ala | Thr |
| | 210 | | | | | 215 | | | | | 220 | | | | |
| Leu | Arg | Cys | Trp | Ala | Leu | Gly | Phe | Tyr | Pro | Gly | Glu | Ile | Thr | Leu | Thr |
| 225 | | | | | 230 | | | | | 235 | | | | | 240 |
| Trp | Gln | Arg | Asp | Gly | Glu | Asp | Gln | Thr | Gln | Asp | Thr | Glu | Leu | Val | Glu |
| | | | | 245 | | | | | 250 | | | | | 255 | |
| Thr | Arg | Pro | Ala | Gly | Asp | Arg | Thr | Phe | Gln | Lys | Trp | Ala | Ala | Val | Val |
| | | | 260 | | | | | 265 | | | | | 270 | | |
| Val | Pro | Ser | Gly | Glu | Glu | Gln | Arg | Tyr | Thr | Cys | His | Val | Gln | His | Glu |
| | | | 275 | | | | | 280 | | | | | 285 | | |
| Gly | Leu | Pro | Lys | Pro | Leu | Thr | Leu | Arg | Trp | Glu | Pro | Ser | Ser | Gln | Ser |
| | 290 | | | | | 295 | | | | | 300 | | | | |
| Thr | Val | Pro | Ile | Val | Gly | Ile | Val | Ala | Gly | Leu | Ala | Val | Leu | Ala | Val |
| 305 | | | | | 310 | | | | | 315 | | | | | 320 |
| Val | Val | Ile | Gly | Ala | Val | Val | Ala | Ala | Val | Met | Cys | Arg | Arg | Lys | Ser |
| | | | | 325 | | | | | 330 | | | | | 335 | |
| Ser | | | | | | | | | | | | | | | |

```
<210> SEQ ID NO 65
<211> LENGTH: 337
<212> TYPE: PRT
<213> ORGANISM: Homo sapiens
<220> FEATURE:
<221> NAME/KEY: DOMAIN
```

```
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 65
```

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
50                  55                  60

Ala Ser Pro Arg Glu Glu Pro Arg Gly Pro Trp Ile Glu Gln Glu Gly
65                  70                  75                  80

Pro Glu Tyr Trp Asp Arg Glu Thr Gln Ile Cys Lys Ala Lys Ala Gln
            85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
            165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val

```
                305                 310                 315                 320
Val Val Ile Gly Ala Val Val Ala Ala Val Met Cys Arg Arg Lys Ser
                    325                 330                 335

Ser

<210> SEQ ID NO 66
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 66

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
    115                 120                 125

Pro Asp Gly Arg Leu Leu Arg Gly Tyr His Gln Asp Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
    195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240
```

-continued

```
Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 67
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 67

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu His Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160
```

```
Asp Thr Ala Ala Gln Ile Thr Gln Arg Lys Trp Glu Ala Arg Val
            165                 170                 175

Ala Glu Gln Leu Arg Ala Tyr Leu Glu Gly Glu Cys Val Glu Trp Leu
        180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
        260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
            325                 330                 335

Ser

<210> SEQ ID NO 68
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 68

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
```

-continued

```
                    85                  90                  95
Thr Asp Arg Glu Asp Leu Arg Thr Leu Leu Arg Tyr Tyr Asn Gln Ser
                100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
        130                 135                 140

Lys Asp Tyr Ile Ala Leu Asn Lys Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 69
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 69

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80
```

```
Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Lys Asn Gly Lys Glu
                165                 170                 175

Thr Leu Gln Arg Ala
            180

<210> SEQ ID NO 70
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 70

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Thr Asn Thr Gln Thr Tyr Arg Glu Asn Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 71
<211> LENGTH: 341
<212> TYPE: PRT
<213> ORGANISM: Homo sapiens
```

```
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(341)
<223> OTHER INFORMATION: transmembrane and cytoplasmic tail

<400> SEQUENCE: 71

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Thr Asn Thr Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300
```

```
Thr Val Pro Ile Val Gly Ile Val Ala Gly Leu Ala Val Leu Ala Val
305                 310                 315                 320

Val Val Ile Gly Ala Val Ala Ala Val Met Cys Arg Arg Lys Ser
            325                 330                 335

Ser Gly Gly Lys Gly
        340

<210> SEQ ID NO 72
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 72

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Cys Arg Tyr Leu Glu Asn Gly Lys Glu
                165                 170                 175

Thr Leu Gln Arg Ala
            180

<210> SEQ ID NO 73
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 73

Ser His Ser Met Arg Tyr Phe His Thr Ser Val Ser Arg Pro Gly Arg
```

```
                1               5                   10                  15
Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
                35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Arg Lys Glu
                165                 170                 175

Thr Leu Gln Arg Ala
            180
```

<210> SEQ ID NO 74
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 74

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
                35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Cys Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
```

```
                145                 150                 155                 160
Gly Glu Cys Val Glu Trp Leu Arg Arg Tyr Leu Glu Asn Gly Lys Glu
                    165                 170                 175

Thr Leu Gln Arg Ala
            180

<210> SEQ ID NO 75
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 75

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Arg Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                    165                 170                 175

Thr Leu Gln Arg Ala
            180

<210> SEQ ID NO 76
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 76

Ser His Ser Met Arg Tyr Phe His Thr Ser Val Ser Arg Pro Gly Arg
1               5                   10                  15
```

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Ser Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 77
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 77

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Arg Met Tyr Gly Cys Asp Val Gly
        115                 120                 125

Pro Asp Gly Arg Leu Leu Arg Gly His Asn Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Ser Gln Arg Lys Leu Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 78
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 78

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asn Leu Arg Ile Ala
65                  70                  75                  80

Leu Arg Tyr Tyr Asn Gln Ser Glu Ala Gly Ser His Thr Leu Gln Asn

```
                    85                  90                  95
Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Val Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 79
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 79

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Ile Ile Gln Arg
                85                  90                  95

Met Tyr Gly Cys Asp Val Gly Pro Asp Gly Arg Leu Leu Arg Gly Tyr
                100                 105                 110

Asp Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Asp Arg Ala Tyr Leu Glu
145                 150                 155                 160

Gly Leu Cys Val Glu Ser Leu Arg Arg Tyr Leu Glu Asn Gly Lys Glu
                165                 170                 175

Thr Leu Gln Arg Ala
            180

<210> SEQ ID NO 80
<211> LENGTH: 206
<212> TYPE: PRT
<213> ORGANISM: Homo sapiens
<220> FEATURE:
<221> NAME/KEY: DOMAIN
```

<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2

<400> SEQUENCE: 80

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65              70                  75                  80

Pro Glu Tyr Trp Asp Arg Glu Thr Gln Ile Cys Lys Ala Lys Ala Gln
            85                  90                  95

Thr Asp Arg Glu Asp Leu Arg Thr Leu Leu Arg Tyr Tyr Asn Gln Ser
        100                 105                 110

Glu Ala Gly Ser His Thr Leu Gln Asn Met Tyr Gly Cys Asp Val Gly
    115                 120                 125

Pro Asp Gly Arg Leu Leu Arg Gly Tyr His Gln Asp Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
            165                 170                 175

Ala Glu Gln Leu Arg Ala Tyr Leu Glu Gly Glu Cys Val Glu Trp Leu
        180                 185                 190

Arg Arg Tyr Leu Glu Asn Gly Lys Asp Thr Leu Gln Arg Ala
    195                 200                 205

<210> SEQ ID NO 81
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 81

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

```
Ile Cys Lys Ala Asn Thr Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 82
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 82

Met Arg Val Thr Glu Pro Arg Thr Leu Leu Leu Leu Trp Gly Ala
 1               5                  10                  15

Val Ala Leu Thr Glu Thr Trp Ala Gly Ser His Ser Met Arg Tyr Phe
                 20                  25                  30

His Thr Ser Val Ser Arg Pro Gly Arg Gly Glu Pro Arg Phe Ile Thr
             35                  40                  45

Val Gly Tyr Val Asp Asp Thr Leu Phe Val Arg Phe Asp Ser Asp Ala
     50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140
```

-continued

```
Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
            355                 360

<210> SEQ ID NO 83
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 83

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Trp Gln Thr
                85                  90                  95

Met Tyr Gly Cys Asp Val Gly Pro Asp Gly Arg Leu Leu Arg Gly His
            100                 105                 110
```

```
Asn Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 84
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 84

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Tyr Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
        130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190
```

-continued

```
Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 85
<211> LENGTH: 206
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2

<400> SEQUENCE: 85

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Trp Gln Thr Met Tyr Gly Cys Asp Leu Gly
        115                 120                 125

Pro Asp Gly Arg Leu Leu Arg Gly Tyr His Gln Asp Ala Tyr Asp Gly
```

```
                    130                 135                 140
Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala
        195                 200                 205

<210> SEQ ID NO 86
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 86

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Thr Cys Val Glu Trp Leu Arg Arg Tyr Leu Glu Asn Gly Lys Glu
                165                 170                 175

Thr Leu Gln Arg Ala
            180

<210> SEQ ID NO 87
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
```

<400> SEQUENCE: 87

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Thr Asn Thr Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 88
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 88

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
50                  55                  60

```
Ala Ser Pro Arg Glu Glu Pro Arg Ala Pro Trp Ile Glu Gln Glu Gly
 65                  70                  75                  80

Pro Glu Phe Trp Asp Arg Glu Thr Gln Ile Cys Lys Ala Lys Ala Gln
                 85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 89
<211> LENGTH: 206
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2

<400> SEQUENCE: 89

Met Arg Val Thr Ala Pro Arg Thr Leu Leu Leu Leu Leu Trp Gly Ala
1               5                   10                  15
```

```
Val Ala Leu Thr Glu Thr Trp Ala Gly Ser His Ser Met Arg Tyr Phe
             20                  25                  30

His Thr Ser Val Ser Arg Pro Gly Arg Gly Glu Pro Arg Phe Ile Thr
         35                  40                  45

Val Gly Tyr Val Asp Asp Thr Leu Phe Val Arg Phe Asp Ser Asp Ala
 50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Ser Lys Thr Asn Thr Gln
                 85                  90                  95

Thr Tyr Arg Glu Ser Leu Arg Asn Leu Arg Gly Tyr Tyr Asn Gln Ser
             100                 105                 110

Glu Ala Gly Ser His Thr Leu Gln Asn Met Tyr Gly Cys Asp Val Gly
         115                 120                 125

Pro Asp Gly Arg Leu Leu Arg Gly Tyr His Gln Asp Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala
        195                 200                 205
```

<210> SEQ ID NO 90
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 90

```
Ser His Ser Met Arg Tyr Phe His Thr Ser Val Ser Arg Pro Gly Arg
 1               5                  10                  15

Gly Glu Pro Arg Phe Ile Thr Val Gly Tyr Val Asp Asp Thr Leu Phe
             20                  25                  30

Val Arg Phe Asp Ser Asp Ala Ala Ser Pro Arg Glu Glu Pro Arg Ala
         35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Ile Ile Gln Arg
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140
```

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 91
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 91

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly His
                100                 105                 110

Asn Gln Tyr Ala Tyr Asp Gly Lys Asp Tyr Ile Ala Leu Asn Glu Asp
            115                 120                 125

Leu Arg Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
    195                 200                 205

Pro Gly Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg

Trp

<210> SEQ ID NO 92
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 92

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Arg
                85                  90                  95

Met Tyr Gly Cys Asp Val Gly Pro Asp Gly Arg Leu Leu Arg Gly Tyr
            100                 105                 110

Asp Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 93
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 93

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala

```
                35                  40                  45
Pro Trp Ile Glu Gln Glu Gly Pro Glu Tyr Trp Asp Arg Asn Thr Gln
 50                  55                  60

Ile Phe Lys Thr Asn Thr Gln Thr Tyr Arg Glu Ser Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 94
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 94

Met Arg Val Thr Ala Pro Arg Thr Leu Leu Leu Leu Trp Gly Ala
 1               5                  10                  15

Val Ala Leu Thr Glu Thr Trp Ala Gly Ser His Ser Met Arg Tyr Phe
                 20                  25                  30

His Thr Ser Val Ser Arg Pro Gly Arg Gly Glu Pro Arg Phe Ile Thr
             35                  40                  45

Val Gly Tyr Val Asp Asp Thr Leu Phe Val Arg Phe Asp Ser Asp Ala
         50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Ser Met Tyr Gly Cys Asp Val Gly
```

-continued

```
                115                 120                 125
Pro Asp Gly Arg Leu Leu Arg Gly His Asn Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Ser Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 95
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 95

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
```

```
                20                  25                  30
His Thr Ser Val Ser Arg Pro Gly Arg Gly Glu Pro Arg Phe Ile Thr
                35                  40                  45
Val Gly Tyr Val Asp Asp Thr Leu Phe Val Arg Phe Asp Ser Asp Ala
 50                  55                  60
Ala Ser Pro Arg Glu Glu Pro Arg Ala Pro Trp Ile Glu Gln Glu Gly
 65                  70                  75                  80
Pro Glu Tyr Trp Asp Arg Glu Thr Gln Ile Cys Lys Ala Lys Ala Gln
                85                  90                  95
Thr Asp Arg Glu Ser Leu Arg Thr Leu Leu Arg Tyr Tyr Asn Gln Ser
                100                 105                 110
Glu Ala Gly Ser His Thr Leu Gln Asn Met Tyr Gly Cys Asp Val Gly
                115                 120                 125
Pro Asp Gly Arg Leu Leu Arg Gly Tyr His Gln Asp Ala Tyr Asp Gly
                130                 135                 140
Lys Asp Tyr Ile Ala Leu Asn Glu Asp Leu Ser Ser Trp Thr Ala Ala
145                 150                 155                 160
Asp Thr Ala Ala Gln Ile Thr Gln Arg Lys Trp Glu Ala Ala Arg Glu
                165                 170                 175
Ala Glu Gln Trp Arg Ala Tyr Leu Glu Gly Leu Cys Val Glu Trp Leu
                180                 185                 190
Arg Arg Tyr Leu Glu Asn Gly Lys Glu Thr Leu Gln Arg Ala Asp Pro
                195                 200                 205
Pro Lys Thr His Val Thr His His Pro Ile Ser Asp His Glu Ala Thr
                210                 215                 220
Leu Arg Cys Trp Ala Leu Gly Phe Tyr Pro Gly Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Arg Thr Phe Gln Lys Trp Ala Ala Val Val
                260                 265                 270
Val Pro Ser Gly Glu Glu Gln Arg Tyr Thr Cys His Val Gln His Glu
                275                 280                 285
Gly Leu Pro Lys Pro Leu Thr Leu Arg Trp Glu Pro Ser Ser Gln Ser
                290                 295                 300
Thr Val Pro Ile Val Gly Ile Val Ala Gly Leu Ala Val Leu Ala Val
305                 310                 315                 320
Val Val Ile Gly Ala Val Val Ala Ala Val Met Cys Arg Arg Lys Ser
                325                 330                 335
Ser Gly Gly Lys Gly Gly Ser Tyr Ser Gln Ala Ala Cys Ser Asp Ser
                340                 345                 350
Ala Gln Gly Ser Asp Val Ser Leu Thr Ala
                355                 360

<210> SEQ ID NO 96
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
```

```
<400> SEQUENCE: 96

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Gln Ala Gln Thr Asp Arg Glu Ser Leu Arg Asn Leu
65                  70                  75                  80

Arg Gly Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 97
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 97

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
```

```
                130             135             140
Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 98
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 98

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Thr Cys Val Glu Trp Leu Arg Arg His Leu Glu Asn Gly Lys Glu
                165                 170                 175

Thr Leu Gln Arg Ala
            180

<210> SEQ ID NO 99
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 99
```

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Ser Lys Thr Asn Thr Gln Thr Tyr Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
            165                 170                 175

Thr Leu Gln Arg Ala
        180

<210> SEQ ID NO 100
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 100

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asn Leu Arg Ile Ala
65                  70                  75                  80

Leu Arg Tyr Tyr Asn Gln Ser Glu Ala Gly Ser His Ile Ile Gln Arg
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140
```

```
Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 101
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 101

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Gln Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 102
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
```

```
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 102

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Pro Arg Phe Ile Thr
        35                  40                  45

Val Gly Tyr Val Asp Asp Thr Leu Phe Val Arg Phe Asp Ser Asp Ala
    50                  55                      60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly Tyr His Gln Asp Ala Tyr Asp Gly
    130                 135                     140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                     220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                     300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360
```

```
<210> SEQ ID NO 103
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 103

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Asn Leu
65                  70                  75                  80

Arg Gly Tyr Tyr Asn Gln Ser Glu Ala Gly Ser His Thr Leu Gln Ser
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 104
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 104

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60
```

```
Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Ser
                 85                  90                  95

Met Tyr Gly Cys Asp Val Gly Pro Asp Gly Arg Leu Leu Arg Gly His
            100                 105                 110

Asp Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
            165                 170                 175

Thr Leu Gln Arg Ala
            180
```

```
<210> SEQ ID NO 105
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 105
```

```
Met Arg Val Thr Ala Pro Arg Thr Leu Leu Leu Leu Trp Gly Ala
 1               5                  10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
             35                  40                  45

Val Gly Tyr Val Asp Asp Thr Leu Phe Val Arg Phe Asp Ser Asp Ala
         50                  55                  60

Ala Ser Pro Arg Glu Glu Pro Arg Ala Pro Trp Ile Glu Gln Glu Gly
 65                  70                  75                  80

Pro Glu Tyr Trp Asp Arg Glu Thr Gln Ile Cys Lys Ala Lys Ala Gln
                 85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr Asn Gln Phe Ala Tyr Asp Gly
130                 135                 140
```

```
Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser
```

```
<210> SEQ ID NO 106
<211> LENGTH: 302
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(284)
<223> OTHER INFORMATION: alpha 3
<220> FEATURE:
<221> NAME/KEY: DOMAIN
<222> LOCATION: (285)..(302)
<223> OTHER INFORMATION: transmembrane and cytoplasmic tail

<400> SEQUENCE: 106
```

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
```

```
                    85                  90                  95
Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Arg Ser Trp Thr Ala Ala Asp Thr Ala Ala Gln Ile Ser Gln Arg
        130                 135                 140

Lys Leu Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Asp
                165                 170                 175

Lys Leu Glu Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp Glu Pro Ser Ser Gln Ser Thr Val Pro Ile Val Gly Ile Val Ala
        275                 280                 285

Gly Leu Ala Val Leu Ala Val Val Val Ile Gly Ala Val Val
290                 295                 300

<210> SEQ ID NO 107
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 107

Ser His Ser Met Arg Tyr Phe Tyr Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
```

```
            115                 120                 125
Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 108
<211> LENGTH: 309
<212> TYPE: PRT
<213> ORGANISM: Homo sapiens
<220> FEATURE:
<221> NAME/KEY: DOMAIN
<222> LOCATION: (1)..(19)
<223> OTHER INFORMATION: signal peptide
<220> FEATURE:
<221> NAME/KEY: DOMAIN
<222> LOCATION: (20)..(109)
<223> OTHER INFORMATION: alpha 1
<220> FEATURE:
<221> NAME/KEY: DOMAIN
<222> LOCATION: (110)..(201)
<223> OTHER INFORMATION: alpha 2
<220> FEATURE:
<221> NAME/KEY: DOMAIN
<222> LOCATION: (202)..(304)
<223> OTHER INFORMATION: alpha 3
<220> FEATURE:
<221> NAME/KEY: DOMAIN
<222> LOCATION: (305)..(309)
<223> OTHER INFORMATION: transmembrane

<400> SEQUENCE: 108

Pro Arg Thr Leu Leu Leu Leu Trp Gly Ala Val Ala Leu Thr Glu
1               5                   10                  15

Thr Trp Ala Gly Ser His Ser Met Arg Tyr Phe His Thr Ser Val Ser
                20                  25                  30

Arg Pro Gly Arg Gly Glu Pro Arg Phe Ile Thr Val Gly Tyr Val Asp
            35                  40                  45

Asp Thr Leu Phe Val Arg Phe Asp Ser Asp Ala Ala Ser Pro Arg Glu
        50                  55                  60

Glu Pro Arg Ala Pro Trp Ile Glu Gln Glu Gly Pro Glu Tyr Trp Asp
65                  70                  75                  80

Arg Glu Thr Gln Ile Cys Lys Ala Lys Ala Gln Thr Asp Arg Glu Asp
                85                  90                  95

Leu Arg Thr Leu Leu Arg Tyr Tyr Asn Gln Ser Glu Ala Gly Ser His
            100                 105                 110

Thr Leu Gln Asn Met Tyr Gly Cys Asp Val Gly Pro Asp Gly Arg Leu
        115                 120                 125

Leu Arg Gly Tyr His Gln Asp Ala Tyr Asp Gly Lys Asp Tyr Ile Ala
        130                 135                 140

Leu Asn Glu Asp Leu Ser Ser Trp Thr Ala Ala Asp Thr Ala Ala Gln
145                 150                 155                 160

Ile Thr Gln Arg Lys Trp Glu Ala Ala Arg Val Ala Glu Gln Leu Arg
                165                 170                 175

Ala Tyr Leu Glu Gly Leu Cys Val Glu Trp Leu Arg Arg Tyr Leu Glu
            180                 185                 190

Asn Gly Lys Glu Thr Leu Gln Arg Ala Asp Pro Pro Lys Thr His Val
```

```
                195                 200                 205
Thr His His Pro Ile Ser Asp His Glu Ala Thr Leu Arg Cys Trp Ala
    210                 215                 220

Leu Gly Phe Tyr Pro Ala Glu Ile Thr Leu Thr Trp Gln Arg Asp Gly
225                 230                 235                 240

Glu Asp Gln Thr Gln Asp Thr Glu Leu Val Glu Thr Arg Pro Ala Gly
                245                 250                 255

Asp Arg Thr Phe Gln Lys Trp Ala Ala Val Val Val Pro Ser Gly Glu
            260                 265                 270

Glu Gln Arg Tyr Thr Cys His Val Gln His Glu Gly Leu Pro Lys Pro
        275                 280                 285

Leu Thr Leu Arg Trp Glu Pro Ser Ser Gln Ser Thr Val Pro Ile Val
290                 295                 300

Gly Ile Val Ala Gly
305

<210> SEQ ID NO 109
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 109

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Leu Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 110
<211> LENGTH: 181
<212> TYPE: PRT
```

-continued

```
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 110

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Asn Leu
65                  70                  75                  80

Arg Gly Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 111
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 111

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80
```

```
Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 112
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 112

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Asn Leu
65                  70                  75                  80

Arg Gly Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 113
<211> LENGTH: 181
<212> TYPE: PRT
<213> ORGANISM: Homo sapiens
<220> FEATURE:
```

```
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 113

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Ser
                85                  90                  95

Met Tyr Gly Cys Asp Val Gly Ser Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 114
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 114

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Tyr Arg Glu Ser Leu Arg Asn Leu
65                  70                  75                  80

Arg Gly Tyr Tyr Asn Gln Ser Glu Ala Gly Ser His Thr Leu Gln Asn
                85                  90                  95
```

```
Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 115
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 115

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Arg Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Lys Thr His Val Thr His His Pro
        180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
```

```
                    210                 215                 220
Gln Asp Thr Glu Leu Val Glu Thr Arg Pro Ala Gly Asp Arg Thr Phe
225                 230                 235                 240

Gln Lys Trp Ala Ala Val Val Pro Ser Gly Glu Glu Arg Tyr
                245                 250                 255

Thr Cys His Val Gln His Glu Gly Leu Pro Lys Pro Leu Thr Leu Arg
                260                 265                 270

Trp

<210> SEQ ID NO 116
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 116

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 117
<211> LENGTH: 362
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
```

```
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 117

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Pro Arg Phe Ile Thr
            35                  40                  45

Val Gly Tyr Val Asp Asp Thr Leu Phe Val Arg Phe Asp Ser Asp Ala
50                  55                      60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
            85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Asp Arg Ala Tyr Leu Glu Gly Leu Cys Val Glu Ser Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Val Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350
```

Ala Gln Gly Ser Asp Val Ser Leu Thr Ala
        355                 360

<210> SEQ ID NO 118
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 118

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Arg Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 119
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 119

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala

```
            35                  40                  45
Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Phe Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 120
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 120

Ser His Ser Met Arg Tyr Phe His Thr Ser Val Ser Arg Pro Gly Arg
 1               5                  10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Ser Leu Arg Arg Tyr Leu Glu Asn Gly Lys Glu
                165                 170                 175

Thr Leu Gln Arg Ala
```

180

```
<210> SEQ ID NO 121
<211> LENGTH: 273
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 121
```

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Gln Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

```
<210> SEQ ID NO 122
<211> LENGTH: 362
<212> TYPE: PRT
```

```
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(362)
<223> OTHER INFORMATION: transmembrane and cytoplasmic tail

<400> SEQUENCE: 122
```

| | | | | | | | | | | | | | | |
|---|---|---|---|---|---|---|---|---|---|---|---|---|---|---|
| Met | Arg | Val | Thr | Ala | Pro | Arg | Thr | Leu | Leu | Leu | Leu | Trp | Gly | Ala |
| 1 | | | | 5 | | | | | 10 | | | | | 15 |
| Val | Ala | Leu | Thr | Glu | Thr | Trp | Ala | Gly | Ser | His | Ser | Met | Arg | Tyr | Phe |
| | | | 20 | | | | | 25 | | | | | 30 | | |
| His | Thr | Ser | Val | Ser | Arg | Pro | Gly | Arg | Gly | Glu | Pro | Arg | Phe | Ile | Thr |
| | | 35 | | | | | 40 | | | | | 45 | | | |
| Val | Gly | Tyr | Val | Asp | Asp | Thr | Leu | Phe | Val | Arg | Phe | Asp | Ser | Asp | Ala |
| 50 | | | | | 55 | | | | | 60 | | | | | |
| Ala | Ser | Pro | Arg | Thr | Glu | Pro | Arg | Ala | Pro | Trp | Ile | Glu | Gln | Glu | Gly |
| 65 | | | | | 70 | | | | | 75 | | | | | 80 |
| Pro | Glu | Tyr | Trp | Asp | Arg | Glu | Thr | Gln | Ile | Cys | Lys | Ala | Lys | Ala | Gln |
| | | | | 85 | | | | | 90 | | | | | 95 | |
| Thr | Asp | Arg | Glu | Asp | Leu | Arg | Thr | Leu | Leu | Arg | Tyr | Tyr | Asn | Gln | Ser |
| | | | 100 | | | | | 105 | | | | | 110 | | |
| Glu | Ala | Gly | Ser | His | Thr | Leu | Gln | Asn | Met | Tyr | Gly | Cys | Asp | Val | Gly |
| | | | | 115 | | | | | 120 | | | | | 125 | |
| Pro | Asp | Gly | Arg | Leu | Leu | Arg | Gly | Tyr | His | Gln | Asp | Ala | Tyr | Asp | Gly |
| | 130 | | | | | 135 | | | | | 140 | | | | |
| Lys | Asp | Tyr | Ile | Ala | Leu | Asn | Glu | Asp | Leu | Ser | Ser | Trp | Thr | Ala | Ala |
| 145 | | | | | 150 | | | | | 155 | | | | | 160 |
| Asp | Thr | Ala | Ala | Gln | Ile | Thr | Gln | Arg | Lys | Trp | Glu | Ala | Ala | Arg | Val |
| | | | | 165 | | | | | 170 | | | | | 175 | |
| Ala | Glu | Gln | Leu | Arg | Ala | Tyr | Leu | Glu | Gly | Glu | Cys | Val | Glu | Trp | Leu |
| | | | 180 | | | | | 185 | | | | | 190 | | |
| Arg | Arg | Tyr | Leu | Glu | Asn | Gly | Lys | Glu | Thr | Leu | Gln | Arg | Ala | Asp | Pro |
| | | | | 195 | | | | | 200 | | | | | 205 | |
| Pro | Lys | Thr | His | Val | Thr | His | His | Pro | Ile | Ser | Asp | His | Glu | Ala | Thr |
| | 210 | | | | | 215 | | | | | 220 | | | | |
| Leu | Arg | Cys | Trp | Ala | Leu | Gly | Phe | Tyr | Pro | Ala | Glu | Ile | Thr | Leu | Thr |
| 225 | | | | | 230 | | | | | 235 | | | | | 240 |
| Trp | Gln | Arg | Asp | Gly | Glu | Asp | Gln | Thr | Gln | Asp | Thr | Glu | Leu | Val | Glu |
| | | | | 245 | | | | | 250 | | | | | 255 | |
| Thr | Arg | Pro | Ala | Gly | Asp | Arg | Thr | Phe | Gln | Lys | Trp | Ala | Ala | Val | Val |
| | | | 260 | | | | | 265 | | | | | 270 | | |
| Val | Pro | Ser | Gly | Glu | Glu | Gln | Arg | Tyr | Thr | Cys | His | Val | Gln | His | Glu |
| | | 275 | | | | | 280 | | | | | 285 | | | |
| Gly | Leu | Pro | Lys | Pro | Leu | Thr | Leu | Arg | Trp | Glu | Pro | Ser | Ser | Gln | Ser |

```
                290                 295                 300
Thr Val Pro Ile Val Gly Ile Val Ala Gly Leu Ala Val Leu Ala Val
305                 310                 315                 320

Val Val Ile Gly Ala Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
                355                 360
```

<210> SEQ ID NO 123
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 123

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
                180
```

<210> SEQ ID NO 124
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 124

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Arg Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 125
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 125

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

```
Leu Ser Ser Trp Thr Ala Ala Asp Thr Val Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180
```

```
<210> SEQ ID NO 126
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 126
```

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Gly Thr Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180
```

```
<210> SEQ ID NO 127
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 127
```

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Arg Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asn Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
            165                 170                 175

Thr Leu Gln Arg Ala
            180

<210> SEQ ID NO 128
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 128

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

```
Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Cys Ala
            180

<210> SEQ ID NO 129
<211> LENGTH: 71
<212> TYPE: PRT
<213> ORGANISM: Homo sapiens
<220> FEATURE:
<221> NAME/KEY: DOMAIN
<222> LOCATION: (1)..(70)
<223> OTHER INFORMATION: alpha 1
<220> FEATURE:
<221> NAME/KEY: misc_feature
<222> LOCATION: (71)..(71)
<223> OTHER INFORMATION: Xaa can be any naturally occurring amino acid

<400> SEQUENCE: 129

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Xaa
65                  70

<210> SEQ ID NO 130
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 130

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
```

```
                115                 120                 125
Leu Ser Ser Trp Thr Ala Ala Asp Thr Ala Ala Gln Ile Thr Gln Gly
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 131
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 131

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 132
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
```

<400> SEQUENCE: 132

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asn Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Thr Cys Val Glu Trp Leu Arg Arg His Leu Glu Asn Gly Lys Glu
                165                 170                 175

Thr Leu Gln Arg Ala
            180
```

<210> SEQ ID NO 133
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 133

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125
```

```
Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180
```

<210> SEQ ID NO 134
<211> LENGTH: 127
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(126)
<223> OTHER INFORMATION: alpha 2
<220> FEATURE:
<221> NAME/KEY: misc_feature
<222> LOCATION: (127)..(127)
<223> OTHER INFORMATION: Xaa can be any naturally occurring amino acid

<400> SEQUENCE: 134

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Xaa
            115                 120                 125
```

<210> SEQ ID NO 135
<211> LENGTH: 53
<212> TYPE: PRT
<213> ORGANISM: Homo sapiens
<220> FEATURE:
<221> NAME/KEY: DOMAIN
<222> LOCATION: (1)..(52)
<223> OTHER INFORMATION: alpha 1
<220> FEATURE:
<221> NAME/KEY: misc_feature
<222> LOCATION: (53)..(53)
<223> OTHER INFORMATION: Xaa can be any naturally occurring amino acid

<400> SEQUENCE: 135

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
```

```
                    35                  40                  45
Pro Trp Ile Glu Xaa
    50

<210> SEQ ID NO 136
<211> LENGTH: 213
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(212)
<223> OTHER INFORMATION: alpha 3
<220> FEATURE:
<221> NAME/KEY: misc_feature
<222> LOCATION: (213)..(213)
<223> OTHER INFORMATION: Xaa can be any naturally occurring amino acid

<400> SEQUENCE: 136

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Thr Arg Ala Ser Ala Trp Ser Gly Ser
            180                 185                 190

Ala Asp Thr Trp Arg Thr Gly Arg Arg Cys Ser Ala Arg Thr Pro
        195                 200                 205

Gln Arg His Thr Xaa
    210

<210> SEQ ID NO 137
<211> LENGTH: 273
<212> TYPE: PRT
```

<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2
<220> FEATURE:
<221> NAME/KEY: DOMAIN
<222> LOCATION: (182)..(273)
<223> OTHER INFORMATION: alpha 3

<400> SEQUENCE: 137

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp
```

<210> SEQ ID NO 138
<211> LENGTH: 298
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:

```
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(298)
<223> OTHER INFORMATION: alpha 3

<400> SEQUENCE: 138
```

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65              70                  75                  80

Pro Glu Tyr Trp Asp Arg Glu Thr Gln Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp Leu Glu Ala Thr
    210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp
    290                 295

```
<210> SEQ ID NO 139
<211> LENGTH: 337
<212> TYPE: PRT
<213> ORGANISM: Homo sapiens
<220> FEATURE:
<221> NAME/KEY: DOMAIN
<222> LOCATION: (1)..(24)
```

```
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 139
```

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Ser Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Gly Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Leu Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

```
Val Val Ile Gly Ala Val Ala Ala Val Met Cys Arg Arg Lys Ser
            325                 330                 335

Ser

<210> SEQ ID NO 140
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 140

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Arg
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 141
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 141

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30
```

```
Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
             100                 105                 110

His Gln Asp Ala Tyr Asp Gly Lys Asp Tyr Ile Ala Leu Asn Glu Asp
             115                 120                 125

Leu Ser Ser Trp Thr Ala Ala Asp Thr Ala Ala Gln Ile Thr Gln Arg
 130                 135                 140

Lys Trp Glu Ala Ala Arg Val Ala Glu Gln Leu Arg Ala Tyr Leu Glu
145                 150                 155                 160

Gly Thr Cys Val Glu Trp Leu Arg Arg Tyr Leu Glu Asn Gly Lys Glu
                 165                 170                 175

Thr Leu Gln Arg Ala
         180

<210> SEQ ID NO 142
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 142

Ser His Ser Met Arg Tyr Phe His Thr Ser Val Ser Arg Pro Gly Arg
 1               5                  10                  15

Gly Glu Pro Arg Phe Ile Thr Val Gly Tyr Val Asp Asp Thr Leu Phe
             20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Asn Gly Cys Asp Val Gly Pro Asp Gly Arg Leu Leu Arg Gly Tyr
             100                 105                 110

His Gln Asp Ala Tyr Asp Gly Lys Asp Tyr Ile Ala Leu Asn Glu Asp
             115                 120                 125

Leu Ser Ser Trp Thr Ala Ala Asp Thr Ala Ala Gln Ile Thr Gln Arg
 130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                 165                 170                 175
```

Thr Leu Gln Arg Ala
        180

<210> SEQ ID NO 143
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 143

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser Gln Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 144
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 144

Ser His Ser Met Arg Tyr Phe His Thr Phe Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala

```
                35                  40                  45
Pro Trp Ile Glu Gln Glu Gly Pro Glu Tyr Trp Asp Arg Glu Thr Gln
 50                  55                  60
Ile Cys Lys Ala Lys Ala Gln Thr Asp Arg Glu Asp Leu Arg Thr Leu
 65                  70                  75                  80
Leu Arg Tyr Tyr Asn Gln Ser Glu Ala Gly Ser His Thr Leu Gln Asn
                 85                  90                  95
Met Tyr Gly Cys Asp Val Gly Pro Asp Gly Arg Leu Leu Arg Gly Tyr
                100                 105                 110
His Gln Asp Ala Tyr Asp Gly Lys Asp Tyr Ile Ala Leu Asn Glu Asp
                115                 120                 125
Leu Ser Ser Trp Thr Ala Ala Asp Thr Ala Ala Gln Ile Thr Gln Arg
                130                 135                 140
Lys Trp Glu Ala Ala Arg Val Ala Glu Gln Leu Arg Ala Tyr Leu Glu
145                 150                 155                 160
Gly Glu Cys Val Glu Trp Leu Arg Arg Tyr Leu Glu Asn Gly Lys Glu
                165                 170                 175
Thr Leu Gln Arg Ala
                180

<210> SEQ ID NO 145
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 145

Ser His Ser Met Arg Tyr Phe His Thr Ser Val Ser Arg Pro Gly Arg
  1               5                  10                  15
Gly Glu Pro Arg Phe Ile Ser Val Gly Tyr Val Asp Asp Thr Gln Phe
                 20                  25                  30
Val Arg Phe Asp Ser Asp Ala Ala Ser Pro Arg Glu Glu Pro Arg Ala
                 35                  40                  45
Pro Trp Ile Glu Gln Glu Gly Pro Glu Tyr Trp Asp Arg Glu Thr Gln
 50                  55                  60
Ile Cys Lys Ala Lys Ala Gln Thr Asp Arg Glu Asn Leu Arg Ile Ala
 65                  70                  75                  80
Leu Arg Tyr Tyr Asn Gln Ser Glu Ala Gly Ser His Thr Leu Gln Asn
                 85                  90                  95
Met Tyr Gly Cys Asp Val Gly Pro Asp Gly Arg Leu Leu Arg Gly Tyr
                100                 105                 110
His Gln Asp Ala Tyr Asp Gly Lys Asp Tyr Ile Ala Leu Asn Glu Asp
                115                 120                 125
Leu Ser Ser Trp Thr Ala Ala Asp Thr Ala Ala Gln Ile Thr Gln Arg
                130                 135                 140
Lys Trp Glu Ala Ala Arg Val Ala Glu Gln Leu Arg Ala Tyr Leu Glu
145                 150                 155                 160
Gly Glu Cys Val Glu Trp Leu Arg Arg Tyr Leu Glu Asn Gly Lys Glu
                165                 170                 175
Thr Leu Gln Arg Ala
```

<210> SEQ ID NO 146
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 146

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 147
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 147

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

```
Pro Trp Ile Glu Gln Glu Gly Pro Glu Tyr Trp Asp Arg Glu Thr Gln
    50                  55                  60

Ile Cys Lys Ala Asn Thr Gln Thr Asp Arg Glu Asn Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 148
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 148

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180
```

```
<210> SEQ ID NO 149
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 149

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Val Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 150
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 150

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60
```

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser Arg Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 151
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 151

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Trp Gln Thr
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 152

```
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 152

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Val Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 153
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 153

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asn Leu Arg Ile Ala
```

```
                65                  70                  75                  80
Leu Arg Tyr Tyr Asn Gln Ser Glu Ala Gly Ser His Thr Leu Gln Asn
                    85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
                130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Asp
                165                 170                 175

Thr Leu Glu Arg Ala
                180

<210> SEQ ID NO 154
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 154

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
                35                  40                  45

Pro Trp Ile Glu Gln Glu Gly Pro Glu Tyr Trp Asp Arg Glu Thr Gln
50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                    85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Gln Asn Glu Asp
                115                 120                 125

Leu Ser Ser Trp Thr Ala Ala Asp Thr Ala Ala Gln Ile Thr Gln Arg
                130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
                180

<210> SEQ ID NO 155
<211> LENGTH: 181
<212> TYPE: PRT
```

```
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 155

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Gln Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 156
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 156

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80
```

-continued

```
Leu Arg Tyr Tyr Asn Gln Ser Glu Ala Gly Ser His Thr Leu Gln Asn
                85                  90                  95
Met Tyr Gly Cys Asp Val Gly Pro Asp Gly Arg Leu Leu Arg Gly Tyr
            100                 105                 110
His Gln Asp Ala Tyr Asp Gly Lys Asp Tyr Ile Ala Leu Asn Glu Asp
        115                 120                 125
Leu Ser Ser Trp Thr Ala Ala Asp Thr Ala Gln Ile Thr Gln Arg
    130                 135                 140
Lys Trp Glu Ala Ala Arg Glu Ala Glu Gln Leu Arg Ala Tyr Leu Glu
145                 150                 155                 160
Gly Glu Cys Val Glu Trp Leu Arg Arg Tyr Leu Glu Asn Gly Lys Gly
                165                 170                 175
Thr Leu Gln Arg Ala
            180

<210> SEQ ID NO 157
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 157

Ser His Ser Met Arg Tyr Phe His Thr Ser Val Ser Arg Pro Gly Arg
1               5                   10                  15
Gly Glu Pro Arg Phe Ile Thr Val Gly Tyr Val Asp Asp Thr Leu Phe
            20                  25                  30
Val Arg Phe Asp Ser Asp Ala Ala Ser Pro Arg Glu Glu Pro Trp Ala
        35                  40                  45
Pro Trp Ile Glu Gln Glu Gly Pro Glu Tyr Trp Asp Arg Glu Thr Gln
    50                  55                  60
Ile Cys Lys Ala Lys Ala Gln Thr Asp Arg Glu Asp Leu Arg Thr Leu
65                  70                  75                  80
Leu Arg Tyr Tyr Asn Gln Ser Glu Ala Gly Ser His Thr Leu Gln Asn
                85                  90                  95
Met Tyr Gly Cys Asp Val Gly Pro Asp Gly Arg Leu Leu Arg Gly Tyr
            100                 105                 110
His Gln Asp Ala Tyr Asp Gly Lys Asp Tyr Ile Ala Leu Asn Glu Asp
        115                 120                 125
Leu Ser Ser Trp Thr Ala Ala Asp Thr Ala Ala Gln Ile Thr Gln Arg
    130                 135                 140
Lys Trp Glu Ala Ala Arg Val Ala Glu Gln Leu Arg Ala Tyr Leu Glu
145                 150                 155                 160
Gly Glu Cys Val Glu Trp Leu Arg Arg Tyr Leu Glu Asn Gly Lys Glu
                165                 170                 175
Thr Leu Gln Arg Ala
            180

<210> SEQ ID NO 158
<211> LENGTH: 181
<212> TYPE: PRT
<213> ORGANISM: Homo sapiens
<220> FEATURE:
```

```
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 158

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Ile Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 159
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 159

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asn Leu Arg Asn Leu
65                  70                  75                  80

Arg Gly Tyr Tyr Asn Gln Ser Glu Ala Gly Ser His Thr Leu Gln Asn
                85                  90                  95
```

```
Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 160
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 160

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 161
<211> LENGTH: 181
<212> TYPE: PRT
<213> ORGANISM: Homo sapiens
<220> FEATURE:
<221> NAME/KEY: DOMAIN
<222> LOCATION: (1)..(89)
```

<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 161

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 162
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 162

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr

```
                    100                 105                 110

His Gln Asp Ala Tyr Asp Gly Lys Asp Tyr Ile Ala Leu Asn Glu Asp
                115                 120                 125

Leu Arg Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 163
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 163

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Tyr Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Ser Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
                100                 105                 110

Asp Gln Tyr Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
            130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 164
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
```

```
<221> NAME/KEY: DOMAIN
<222> LOCATION: (90)..(181)
<223> OTHER INFORMATION: alpha 2

<400> SEQUENCE: 164
```

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Asn Thr Gln
    50                  55                  60

Ile Cys Lys Thr Asn Thr Gln Thr Tyr Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

```
<210> SEQ ID NO 165
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 165
```

Ser His Ser Met Arg Tyr Phe His Thr Ser Val Ser Arg Pro Gly Arg
1               5                   10                  15

Gly Glu Pro Arg Phe Ile Thr Val Gly Tyr Ala Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

```
His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 166
<211> LENGTH: 58
<212> TYPE: PRT
<213> ORGANISM: Homo sapiens
<220> FEATURE:
<221> NAME/KEY: DOMAIN
<222> LOCATION: (1)..(58)
<223> OTHER INFORMATION: alpha 1

<400> SEQUENCE: 166

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr
        50                  55

<210> SEQ ID NO 167
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 167

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
        50                  55                  60

Ile Cys Lys Ala Lys Ala Gln Thr Asp Arg Glu Asn Leu Arg Ile Ala
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125
```

```
Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180
```

<210> SEQ ID NO 168
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 168

```
Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Ala Ser Pro Arg Glu Glu Pro Arg Ala
            35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Arg Pro Asp Gly Arg Leu Leu Arg Gly Tyr
                100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180
```

<210> SEQ ID NO 169
<211> LENGTH: 337
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: signal peptide
<220> FEATURE:
<221> NAME/KEY: DOMAIN
<222> LOCATION: (25)..(114)
<223> OTHER INFORMATION: alpha 1
<220> FEATURE:
<221> NAME/KEY: DOMAIN
<222> LOCATION: (115)..(206)
<223> OTHER INFORMATION: alpha 2
<220> FEATURE:
<221> NAME/KEY: DOMAIN
<222> LOCATION: (207)..(309)
<223> OTHER INFORMATION: alpha 3
<220> FEATURE:
<221> NAME/KEY: DOMAIN
<222> LOCATION: (310)..(337)
<223> OTHER INFORMATION: transmembrane and cytoplasmic tail

<400> SEQUENCE: 169

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Arg
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

```
<210> SEQ ID NO 170
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 170

Ser His Cys Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60

Ile Cys Lys Ala Lys Ala Gln Thr Asp Arg Glu Asp Leu Arg Thr Leu
65                  70                  75                  80

Leu Arg Tyr Tyr Asn Gln Ser Glu Ala Gly Ser His Thr Leu Gln Asn
                85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
        180

<210> SEQ ID NO 171
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 171

Ser His Ser Met Arg Tyr Phe His Thr Ser Val Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Ala Ser Pro Arg Glu Glu Pro Arg Ala
        35                  40                  45

Pro Trp Ile Glu Gln Glu Gly Pro Glu Tyr Trp Asp Arg Glu Thr Gln
    50                  55                  60
```

```
Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Leu
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 172
<211> LENGTH: 181
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: alpha 1
<220> FEATURE:
<221> NAME/KEY: DOMAIN
<222> LOCATION: (90)..(181)
<223> OTHER INFORMATION: alpha 2

<400> SEQUENCE: 172

Ser His Ser Met Arg Tyr Phe His Thr Ser Val Ser Arg Pro Gly Arg
  1               5                  10                  15

Gly Glu Pro Arg Phe Ile Thr Val Gly Tyr Val Asp Asp Thr Leu Phe
             20                  25                  30

Val Arg Phe Asp Ser Asp Ala Ala Ser Pro Arg Glu Glu Pro Arg Ala
         35                  40                  45

Pro Trp Ile Glu Gln Glu Gly Pro Glu Tyr Trp Asp Arg Glu Thr Gln
 50                  55                  60

Ile Cys Lys Ala Lys Ala Gln Thr Asp Arg Glu Asp Leu Arg Thr Leu
 65                  70                  75                  80

Leu Arg Tyr Tyr Asn Gln Ser Glu Ala Gly Ser His Thr Leu Gln Asn
                 85                  90                  95

Met Tyr Gly Cys Asp Val Gly Pro Asp Gly Arg Leu Leu Arg Gly Tyr
            100                 105                 110

His Gln Asp Ala Tyr Asp Gly Lys Asp Tyr Ile Ala Leu Asn Glu Asp
            115                 120                 125

Leu Ser Ser Trp Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 173
<211> LENGTH: 10
```

```
<212> TYPE: PRT
<213> ORGANISM: Artificial Sequence
<220> FEATURE:
<223> OTHER INFORMATION: Synthetic polypeptide

<400> SEQUENCE: 173

Gly Gly Gly Gly Ser Gly Gly Gly Gly Ser
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 174

Ser Arg Tyr Trp Ala Ile Arg Thr Arg
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 175

Arg Arg Ile Tyr Asp Leu Ile Glu Leu
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 176

Thr Pro Arg Thr Gly Gly Gly Ala Met
1               5
```